(12) United States Patent
Yamaguchi et al.

(10) Patent No.: US 8,044,236 B2
(45) Date of Patent: Oct. 25, 2011

(54) CARBOXILIC ACID DERIVATIVES

(75) Inventors: Youichi Yamaguchi, Kawasaki (JP);
Takeshi Yanase, Tokyo (JP); Susumu Muto, Machida (JP); Akiko Itai, Tokyo (JP)

(73) Assignee: Institute of Medicinal Molecular Design, Inc., Tokyo (JP)

( * ) Notice: Subject to any disclaimer, the term of this patent is extended or adjusted under 35 U.S.C. 154(b) by 766 days.

(21) Appl. No.: 11/870,718

(22) Filed: Oct. 11, 2007

(65) Prior Publication Data

US 2008/0275116 A1 Nov. 6, 2008

Related U.S. Application Data

(60) Provisional application No. 60/851,300, filed on Oct. 13, 2006.

(30) Foreign Application Priority Data

Oct. 12, 2006 (JP) .................................. 2006-278528

(51) Int. Cl.
*C07C 65/00* (2006.01)
*C07C 59/40* (2006.01)

(52) U.S. Cl. ........................................ 562/469; 562/465

(58) Field of Classification Search .................. None
See application file for complete search history.

(56) References Cited

U.S. PATENT DOCUMENTS

| | | | |
|---|---|---|---|
| 5,324,743 A | 6/1994 | Dillard et al. | |
| 5,462,954 A | 10/1995 | Baker et al. | |
| 5,552,441 A | 9/1996 | Dillard et al. | |
| 5,750,530 A | 5/1998 | Bryans et al. | |
| 5,817,684 A | 10/1998 | Fleisch et al. | |
| 5,891,877 A | 4/1999 | Brocchini et al. | |
| 5,910,505 A | 6/1999 | Fleisch et al. | |
| 5,914,340 A | 6/1999 | Fleisch et al. | |
| 5,998,454 A | 12/1999 | Fleisch et al. | |
| 6,589,970 B2 | 7/2003 | Commons et al. | |
| 6,599,925 B2 | 7/2003 | Elokdah et al. | |
| 6,800,654 B2 | 10/2004 | Mayers et al. | |
| 7,056,943 B2 | 6/2006 | Elokdah et al. | |
| 7,074,817 B2 | 7/2006 | Elokdah et al. | |
| 7,074,836 B1 | 7/2006 | Kawada et al. | |
| 7,101,903 B2 | 9/2006 | Elokdah et al. | |
| 7,101,915 B1 | 9/2006 | Kawada et al. | |
| 7,220,783 B2 | 5/2007 | Kawada et al. | |
| 7,265,148 B2 | 9/2007 | Hu | |
| 7,291,639 B2 | 11/2007 | Elokdah et al. | |
| 7,491,748 B2 | 2/2009 | Tani et al. | |
| 7,786,161 B2 | 8/2010 | Tani et al. | |
| 2004/0053962 A1 | 3/2004 | Adrian | |
| 2004/0058965 A1 | 3/2004 | Momose et al. | |
| 2005/0070584 A1 | 3/2005 | Havran et al. | |
| 2005/0070585 A1 | 3/2005 | Elokdah et al. | |
| 2005/0096377 A1 | 5/2005 | Hu | |
| 2005/0119327 A1 | 6/2005 | Hu | |
| 2005/0124664 A1 | 6/2005 | Sartori et al. | |
| 2005/0124667 A1 | 6/2005 | Sartori et al. | |
| 2005/0143384 A1 | 6/2005 | Sartori et al. | |
| 2006/0020003 A1 | 1/2006 | Commons et al. | |
| 2006/0173058 A1 | 8/2006 | Brown et al. | |
| 2007/0207175 A1 | 9/2007 | Clary et al. | |
| 2007/0213336 A1 | 9/2007 | Clary et al. | |
| 2007/0276011 A1 | 11/2007 | Muto et al. | |

FOREIGN PATENT DOCUMENTS

| | | |
|---|---|---|
| EP | 1357115 A1 | 10/2003 |
| EP | 1666469 A1 | 6/2006 |
| GB | 2372740 A | 9/2002 |
| JP | 2006-523196 A | 10/2006 |
| WO | 95/21832 A1 | 8/1995 |
| WO | 95/32190 A2 | 11/1995 |
| WO | 96/36347 | 11/1996 |
| WO | 98/25600 | 6/1998 |
| WO | 98/25616 | 6/1998 |
| WO | 98/42334 | 10/1998 |

(Continued)

OTHER PUBLICATIONS

Silverman, "Bioisosteres" in The Organic Chemistry of Drug Design and Drug Action, Academic Press, Inc., 1992, pp. 19-23.*
Franz et al., Synlett (2003), (4), 522-526.*
Silverman, "Prodrugs" in The Organic Chemistry of Drug Design and Drug Action, ,Academic Press, Inc., 1992, pp. 353-355.*
F.F. Paintner et al., "A New Convergent Approach to Biphenomycin Antibiotics", Synlett, 2003, vol. 4, pp. 522-526.
J. Schneiderman et al., "Increased type 1 plasminogen activator inhibitor gene expression in atherosclerotic human arteries", Proc. Natl. Acad. Sci. U.S.A., 1992, vol. 89, No. 15, pp. 6998-7002.
L.A. Erickson et al., "Development of venous occlusions in mice transgenic for the plasminogen activator inhibitor-1 gene", Nature, 1990, vol. 346, pp. 74-76.

(Continued)

*Primary Examiner* — Karl J Puttlitz
(74) *Attorney, Agent, or Firm* — Greenblum & Bernstein, PLC

(57) ABSTRACT

A compound represented by the following general formula (I) or a salt thereof, or a hydrate thereof or a solvate thereof having an inhibitory action against plasminogen activator inhibitor-1 (PAI-1):

wherein $R^1$ represents a $C_{6-10}$ aryl group; or a substituted $C_{6-10}$ aryl group, $R^2$ represents a $C_{6-10}$ aryl group; or a $C_{6-10}$ aryl group substituted with a group or groups selected from the group consisting of a halogen atom, nitro group, a $C_{1-6}$ alkyl group, a halogenated $C_{1-6}$ alkyl group, a $C_{1-6}$ alkoxy group, a halogenated $C_{1-6}$ alkoxy group, a phenyl group and carboxy group, X represents —$CH_2$—, —$CH_2CH_2$—, —CH=CH— or —N($R^3$)—C(=O)—, Y represents carboxy group or a bioisostere of carboxy group, $R^3$ represents hydrogen atom, a $C_{1-4}$ alkyl group or a $C_{7-12}$ aralkyl group, m represents 0 or 1.

4 Claims, No Drawings

FOREIGN PATENT DOCUMENTS

| WO | 98/42335 | 10/1998 |
| --- | --- | --- |
| WO | 98/42336 | 10/1998 |
| WO | 98/42345 | 10/1998 |
| WO | 98/42346 | 10/1998 |
| WO | 98/42650 | 10/1998 |
| WO | 01/34135 | 5/2001 |
| WO | 01/34137 | 5/2001 |
| WO | 01/34197 | 5/2001 |
| WO | 01/34198 | 5/2001 |
| WO | 02/053547 A1 | 7/2002 |
| WO | 03/000253 A1 | 1/2003 |
| WO | 03/000258 A1 | 1/2003 |
| WO | 03/000649 A1 | 1/2003 |
| WO | 03/000671 A1 | 1/2003 |
| WO | 03/000684 A1 | 1/2003 |
| WO | 2004/024939 | 3/2004 |
| WO | 2004/052856 A1 | 6/2004 |
| WO | 2004/052893 A2 | 6/2004 |
| WO | 2005/030192 A1 | 4/2005 |
| WO | 2005/030204 A1 | 4/2005 |
| WO | 2005/030702 A1 | 4/2005 |
| WO | 2005/030715 A1 | 4/2005 |
| WO | 2005/030716 A1 | 4/2005 |
| WO | 2005/030756 A1 | 4/2005 |

OTHER PUBLICATIONS

F. Samad et al., "Tissue Distribution and Regulation of Plasminogen Activator Inhibitor-1 in Obese Mice", Molecular Medicine, 1996, vol. 2, No. 5, pp. 568-582.

K. Schaefer et al., "Disruption of the plasminogen activator inhibitor 1 gene reduces the adiposity and improves the metabolic profile of genetically obese and diabetic ob/ob mice", FASAB J., 2001, vol. 15, No. 10, pp. 1840-1842.

H. Tsuchiya et al., "The Antibody to Plasminogen Activator Inhibitor-1 Suppresses Pulmonary Metastases of Human Fibrosarcoma in Athymic Mice", Gen. Diagn. Pathol., 1995, vol. 141, No. 1, pp. 41-48.

K. Bajou et al., "Absence of host plasminogen activator inhibitor 1 prevents cancer invasion and vascularization", Nature Medicine, 1998, vol. 4, No. 8, pp. 923-928.

S. H. Cho et al., "Production of Plasminogen Activator Inhibitor-1 by Human Mast Cells and Its Possible Role in Asthma", The Journal of Immunology, 2000, vol. 165, No. 6, pp. 3154-3161.

K. O. Chad et al., "PAI-1 promotes extracellular matrix deposition in the airways of a murine asthma model", Biochemical and Biophysical Research Communications, 2002, vol. 294, No. 5, pp. 1155-1160.

P. Bjoerquist et al., "Identification of the Binding Site for a Low-Molecular-Weight Inhibitor of Plasminogen Activator Inhibitor Type 1 by Site-Directed Mutagenesis", Biochemistry, 1998, vol. 37, No. 5, pp. 1227-1234.

H. Elokdah et al., "Tiplaxtinin, a Novel, Orally Efficacious Inhibitor of Plasminogen Activator Inhibitor-1: Design, Synthesis, and Preclinical Characterization", J. Med. Chem., 2004, vol. 47, No. 14, pp. 3491-3494.

C. A. Lipinski, "Bioisosterism in Drug Design", Annual Reports in Medicinal Chemistry, 1986, vol. 21, pp. 283-291.

G. A. Patani et al., "Bioisosterism: A rational Approach to Drug Design", Chem. Rev., 1996, vol. 96, pp. 3147-3176.

U.S. Appl. No. 11/870,741 (Yamaguchi et al.), filed Oct. 11, 2007, and entitled "N-Phenyloxamide Derivatives".

Sawyer et al, "Structural analogues of LY292728, a highly potent xanthone dicarboxylic acid leukotriene B4 receptor antagonist spatial positioning of the secondary acid group", Bioorg. Med. Chem. Lett., 4,, 1994, pp. 2077-2082.

Jackson et al, "Comparison of antagonist and agonist binding to the leukotriene B4 receptor on intact human polymorphonuclear neutrophils (PMN)", J. Pharm. Exp. Ther., 262, 1992, pp. 80-89.

* cited by examiner

CARBOXILIC ACID DERIVATIVES

FIELD OF INVENTION

The present invention relates to carboxylic acid derivatives which are useful as inhibitors against plasminogen activator inhibitor-1 (hereinafter referred to as "PAI-1").

BACKGROUND ART

Blood coagulation system consists of a cascade reaction which comprises numbers of combinations of various kinds of proteases and precursors (substrates) thereof, and is regulated mainly depending upon blood endothelial cells. When the blood endothelial cells are disordered to collapse cascade regulation of the blood coagulation, a thrombotic tendency is increased to lead to stenosis or occlusion of blood vessels. The thrombus consists of blood components coagulated intravascularly, which components include fibrin, platelet, erythrocyte, leukocyte and the like.

Fibrinolytic system is a rather simple system as compared with the blood coagulation system. However, factors related to the fibrinolytic system are deeply involved not only in an intravascular dissolution of thrombus but also in various reactions occurring in tissues, such as movement or migration of cell; ovulation; cell proliferation; angiogenesis; reconstruction (remodeling) of tissue; inflammatory response and the like. The fibrinolytic system is driven by serine proteases. The plasminogen is converted into plasmin by a plasminogen activator (hereinafter referred to as "PA"); a tissue-type plasminogen activator (hereinafter referred to as "tPA"); or a urokinase-type plasminogen activator (hereinafter referred to as "uPA"), and the resulting plasmin degrades a fibrin thrombus and tissue protein. The fibrinolytic reaction is regulated and modulated by a plasminogen activator inhibitor-1 (PAI1), a specific inhibitory protein against plasminogen activator existing in vivo. PAI-1 forms a complex with PA in a ratio of one to one to inhibit actions thereof. PAI-1 released from an activated platelet binds to fibrin so as to exist around the fibrin in a concentrated form, especially at the site of thrombogenesis, and inhibits an activity of tPA effectively. Furthermore, PAI-1 accelerates hyperplasia of vascular wall to promote progress of cardiovascular lesion by inhibiting degradation of extracellular matrix by a protease. An activity of the fibrinolytic system is regulated by a balance between PA and PAI-1. Therefore, an increase or a decrease of production of PAI-1 in cells or fluctuation in the activity of PAI-1 molecule is reflected immediately in the activity of the fibrinolytic system in blood. Accordingly, a therapeutic effect for thrombotic diseases is expected by inhibiting PAI-1 activity followed by promoting the activation of PA.

PAI-1 binds to vitronectin, which is a cell adhesion molecule, to inhibit adhesion of cells to the extracellular matrix. Therefore, a therapeutic effect for diseases caused by movement or migration of cell is also expected. Furthermore, plasmin which is indirectly activated by an inhibition of PAI-1 is involved in an activation of transforming growth factor as a cell proliferation inhibitory cytokine or in an activation of collagenase. Therefore, a therapeutic effect for diseases caused by cell proliferation, angiogenesis, and remodeling of tissue is also expected.

It has been reported that an expression of PAI-1 is increased at the lesion of arteriosclerosis to increase risks of thrombotic diseases such as myocardial infarction, deep vein thrombosis (DVT) and disseminated intravascular coagulation (DIC) associated with sepsis (see, Non-Patent Document 1), and a PAI-1 transgenic mouse shows a thrombogenic tendency (see, Non-Patent Document 2).

It has also been reported that a mouse model of obesity shows a significantly higher blood level of PAI-1, and further reported that PAI-1 is synthesized not only in endothelial tissues and hepatic tissues but also in adipose tissues, and an amount of synthesized PAI-1 is rapidly increased, especially in visceral fat (see, Non-Patent Document 3). Furthermore, it has been reported that a PAI-1 gene knock out mouse model of obesity shows a decrease in body weight, and a lowering of blood levels of glucose and insulin (see, Non-Patent Document 4), suggesting a possibility that PAI-1 aggravates various symptoms caused by an accumulation of fats. It has been reported that PAI-1 exists specifically in cancerous tissues to be involved in regulation of physiological function of cancer cells, and that a PAI-1 antibody inhibits metastasis of cancer in a cancer model (see, Non-Patent Document 5). It has also been reported that, when a transplantation of malignant keratinocytes into PAI-1 knock out mouse is carried out, invasion of cancer and angiogenesis are inhibited (see, Non-Patent Document 6).

Furthermore, it has been reported that PAI-1 is secreted from mast cell (see, Non-Patent Document 7), and an accumulation of extracellular matrix in an airway of a mouse model of asthma is alleviated by PAI-1 knockout (see, Non-Patent Document 8).

An arterial lesion as an acute or a chronic rejection after cardiac or renal transplantation is considered to be caused by progressions such as progression of fibrogenesis of tissue, progression of thrombogenesis, progression of proliferation and remodeling of arterial endothelial cell. In experiments of murine cardiac transplantation, when the compound having inhibitory action against PAI-1 was administered, take of a graft was significantly prolonged and an incidence of vascular intimal thickening was reduced to about one third as compared with control group (see, Patent Document 1). Accordingly, the compounds that can inhibit PAI-1 are considered to have inhibitory effects against acute rejections and arterial lesions after organ transplantation such as cardiac transplantation, renal transplantation or the like.

Therefore, compounds having specific inhibitory action against PAI-1 are expected to be agents useful for diseases caused by thrombogenesis, fibrogenesis, accumulation of visceral fat, cell proliferation, angiogenesis, deposition and remodeling of extracellular matrix, and cell movement and migration.

As for compounds having inhibitory action against PAI-1, the compounds disclosed in Patent Documents 1 to 19 and Non-Patent Documents 9 to 10 are known. However, the structural feature of the compounds of the present invention described below is clearly distinguishable from those of the compounds disclosed in the aforementioned documents.

As for {2-aralkyloxy-5-(aryl)phenyl}acetic acid derivatives, 2-[2-[4-[(5-methyl-2-phenyl-4-oxazolyl)methoxy]benzyloxy]-5-phenylphenyl]acetic acid is disclosed in Example 22 of Patent Document 20. However, no result of pharmacological test of the aforementioned compounds is disclosed in the aforementioned patent document. Furthermore, the aforementioned patent document fails to teach nor suggest that {2-aralkyloxy-5-(aryl)phenyl}acetic acid derivatives have inhibitory action against PAI-1.

Non-Patent Document 1: Proc. Natl. Acad. Sci. U.S.A., Vol. 89, No. 15, pp. 6998-7002 (1992).

Non-Patent Document 2: Nature, Vol. 346, No. 6279, pp. 74-76 (1990).

Non-Patent Document 3: Mol. Med., Vol. 2, No. 5, pp. 568-582 (1996).

Non-Patent Document 4: FASEB J., Vol. 15, No. 10, pp. 1840-1842 (2001).
Non-Patent Document 5: Gen. Diagn. Pathol., Vol. 141, No. 1, pp. 41-48 (1995).
Non-Patent Document 6: Nat. Med., Vol. 4, No. 8, pp. 923-928 (1998).
Non-Patent Document 7: J. Immunol., Vol. 165, No. 6, pp. 3154-3161 (2000).
Non-Patent Document 8: Biochem. Biophys. Res. Commun., Vol. 294, No. 5, pp. 1155-1160 (2002).
Non-Patent Document 9: Biochemistry, Vol. 37, No. 5, pp. 1227-1234 (1998).
Non-Patent Document 10: J. Med. Chem., vol. 47, No. 14, pp. 3491-3494 (2004).
Patent Document 1: European Patent Application Publication No. EP 1666469
Patent Document 2: The pamphlet of International Publication No. WO95/32190
Patent Document 3: The pamphlet of International Publication No. WO95/21832
Patent Document 4: U. K. Patent Application Publication No. GB 2372740
Patent Document 5: The pamphlet of International Publication No. WO03/000253
Patent Document 6: The pamphlet of International Publication No. WO03/000258
Patent Document 7: The pamphlet of International Publication No. WO03/000649
Patent Document 8: The pamphlet of International Publication No. WO03/000671
Patent Document 9: The pamphlet of International Publication No. WO03/000684
Patent Document 10: The pamphlet of International Publication No. WO2004/052856
Patent Document 11: The pamphlet of International Publication No. WO2004/052893
Patent Document 12: The pamphlet of International Publication No. WO2005/030192
Patent Document 13: The pamphlet of International Publication No. WO2005/030204
Patent Document 14: The pamphlet of International Publication No. WO2005/030715
Patent Document 15: The pamphlet of International Publication No. WO2005/030716
Patent Document 16: The pamphlet of International Publication No. WO2005/030756
Patent Document 17: U.S. Patent Application Publication No. US 2005/0124664
Patent Document 18: U.S. Patent Application Publication No. US 2005/0124667
Patent Document 19: U.S. Patent Application Publication No. US 2005/0143384
Patent Document 20: European Patent Publication No. EP 1357115

DISCLOSURE OF THE INVENTION

Problems to be Solved by the Invention

An object of the present invention is to provide a low molecular compound which is useful for preventive and/or therapeutic treatment of diseases with stenosis or occlusion caused by thrombus.

Another object of the present invention is to provide an antithrombotic compound with few hemorrhagic diatheses by selective inhibition of PAI-1 which is highly expressed in local lesions and a following indirect activation of PA. Further object of the present invention is to provide a medicament which is provided in the form of injections as well as in a form of preparation depending on a target disease and a purpose of application by using the low molecular compound which inhibits PAI-1.

Still further object of the present invention is to provide low molecular compounds which are useful for preventive and/or therapeutic treatment of other diseases caused by an expression of PAI-1, an enhancement of PAI-1 activity, or a lowering of plasmin activity, for example, diseases caused by fibrogenesis, accumulation of visceral fat, cell proliferation, angiogenesis, deposition or remodeling of extracellular matrix, and cell movement and migration.

Means to Solve the Problems

The inventors of the present invention conducted various studies to solve the aforementioned objects. As a result, they found that {2-aryloxy-5-(aryl)phenyl}acetic acid derivatives, {2-aralkyloxy-5-(aryl)phenyl}acetic acid derivatives, 3-{2-aryloxy-5-(aryl)phenyl}propanoic acid derivatives, 3-{2-aralkyloxy-5-(aryl)phenyl}propanoic acid derivatives, 3-{2-aryloxy-5-(aryl)phenyl}propenoic acid derivatives, 3-{2-aralkyloxy-5-(aryl)phenyl}propenoic acid derivatives, N-{2-aryloxy-5 (aryl)phenyl}oxamic acid derivatives, and N-{2-aralkyloxy-5-(aryl)phenyl}oxamic acid derivatives have strong inhibitory action against PAI-1 and achieved the present invention.

The present invention thus provides:
(1) a compound represented by the following general formula (I) or a salt thereof, or a hydrate thereof or a solvate thereof:

[Chemical formula 1]

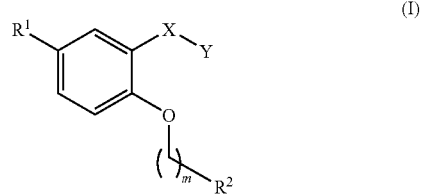

(I)

wherein $R^1$ represents a $C_{6-10}$ aryl group; or a substituted $C_{6-10}$ aryl group,
$R^2$ represents a $C_{6-10}$ aryl group; or a $C_{6-10}$ aryl group substituted with a group or groups selected from the group consisting of a halogen atom, nitro group, a $C_{1-6}$ alkyl group, a halogenated $C_{1-6}$ alkyl group, a $C_{1-6}$ alkoxy group, a halogenated $C_{1-6}$ alkoxy group, a phenyl group and carboxy group,
X represents —$CH_2$—, —$CH_2CH_2$—, —CH=CH— or —N($R^3$)—C(=O)— wherein the nitrogen atom binds to the benzene ring and the carbon atom binds to Y,
Y represents carboxy group or a bioisostere of carboxy group,
$R^3$ represents hydrogen atom, a $C_{1-4}$ alkyl group or a $C_{7-12}$ aralkyl group,
m represents 0 or 1.
According to preferred embodiments of the present invention, provided are:
(2) the compound according to the aforementioned (1) or a salt thereof, or a hydrate thereof or a solvate thereof, wherein $R^1$ is a $C_{6-10}$ aryl group; a $C_{6-10}$ aryl group substituted with a group or groups selected from the group consisting of a halogen atom, nitro group, a $C_{1-6}$ alkyl group, a halogenated $C_{1-6}$ alkyl group, a $C_{1-6}$ alkoxy group, a halogenated $C_{1-6}$ alkoxy group, a $C_{1-6}$ alkylenedioxy group, a $C_{1-6}$ alkylsulfanyl group, carboxy group and amino group, $R^2$ is a $C_{6-10}$ aryl group; or a $C_{6-10}$ aryl group substituted with a group or groups selected from the group consisting of a halogen atom, nitro group, a $C_{1-6}$ alkyl group, a halogenated $C_{1-6}$ alkyl group, a $C_{1-6}$ alkoxy group, a halogenated $C_{1-6}$ alkoxy group, a phenyl group and carboxy group, X is —$CH_2$—, —$CH_2CH_2$—, —CH=CH— or —N($R^3$)—C(=O)— wherein the nitrogen atom binds to the benzene ring and the carbon atom binds to Y.

Y is carboxy group or 1H-tetrazol-5-yl group; and (3) the compound according to the aforementioned (2) or a salt thereof, or a hydrate thereof or a solvate thereof, wherein X is —$CH_2$—, —$CH_2CH_2$— or —N($R^3$)—C(=O)— wherein the nitrogen atom binds to the benzene ring and the carbon atom binds to Y, Y is carboxy group.

From another aspect, the present invention provides:

(4) a medicament for preventive and/or therapeutic treatment of diseases caused by an expression of PAI-1 or an enhancement of PAI-1 activity, which comprises as an active ingredient a substance selected from the group consisting of a compound according to any one of the aforementioned (1) to (3) and a pharmacologically acceptable salt thereof, and a hydrate thereof and a solvate thereof;

(5) a PAI-1 inhibitor which comprises as an active ingredient a substance selected from the group consisting of a compound according to any one of the aforementioned (1) to (3) and a pharmacologically acceptable salt thereof, and a hydrate thereof and a solvate thereof;

(6) use of a substance selected from the group consisting of a compound according to any one of the aforementioned (1) to (3) and a pharmacologically acceptable salt thereof, and a hydrate thereof and a solvate thereof for the manufacture of a PAI-1 inhibitor; and (7) use of a substance selected from the group consisting of a compound according to any one of the aforementioned (1) to (3) and a pharmacologically acceptable salt thereof, and a hydrate thereof and a solvate thereof for the manufacture of a medicament for preventive and/or therapeutic treatment of diseases caused by an expression of PAI-1 or an enhancement of PAI-1 activity.

From further another aspect, the present invention provides a method of inhibiting PAI-1 in a mammal including a human, which comprises the step of administering a substance selected from the group consisting of a compound represented by the aforementioned general formula (I) and a pharmacologically acceptable salt thereof, and a hydrate thereof and a solvate thereof at a dose sufficient to inhibit PAI-1; a method of inhibiting PAI-1, which comprises the step of allowing a substance selected from the group consisting of a compound according to the aforementioned (1) and a pharmacologically acceptable salt thereof, and a hydrate thereof and a solvate thereof to act on PAI-1; and a method for preventive and/or therapeutic treatment of diseases caused by an expression of PAI-1 or an enhancement of PAI-1 activity in a mammal including a human, which comprises the step of administering a substance selected from the group consisting of a compound represented by the aforementioned general formula (I) and a pharmacologically acceptable salt thereof, and a hydrate thereof and a solvate thereof at a dose preventively and/or therapeutically sufficient to treat said diseases.

In the present specification, "allow to act on" means to allow a substance selected from the group consisting of a compound represented by the general formula (I) and a pharmacologically acceptable salt thereof, and a hydrate thereof and a solvate thereof to exhibit an inhibitory action against activation of PAI-1 by addition or administration thereof. The action may target PAI-1 or a cultured cell that produces PAI-1 or a cell within an individual. The aforementioned individual may be a human or other mammals.

BEST MODE FOR CARRYING OUT THE INVENTION

This application claims the benefit of priority to Japan Patent Application No. 2006-278528, filed on Oct. 12, 2006, and U.S. Provisional Application No. 60/851,300, filed on Oct. 13, 2006. All of the disclosures of the specifications of these applications are herein incorporated by reference.

The terms used in the present specification have the following meanings.

As the halogen atom, any of fluorine atom, chlorine atom, bromine atom or iodine atom may be used unless otherwise specifically referred to.

The "alkyl group" or an alkyl moiety of the substituents containing the alkyl moiety may be straight chain, branched chain, cyclic, or combination of these.

Examples of the "$C_{1-6}$ alkyl group" include, for example, n-pentyl group, isopentyl group, neopentyl group, tert-pentyl group, 1-ethylpropyl group, n-hexyl group, cyclopentyl group and cyclohexyl group, besides $C_{1-4}$ alkyl groups such as methyl group, ethyl group, n-propyl group, isopropyl group, n-butyl group, isobutyl group, sec-butyl group, tert-butyl group, cyclopropyl group, cyclobutyl group and (cyclopropyl)methyl group.

Examples of the "halogenated $C_{1-6}$ alkyl group" include, for example, perfluoropentyl group and perfluorohexyl group, besides halogenated $C_{1-4}$ alkyl groups such as chloromethyl group, bromomethyl group, fluoromethyl group, dichloromethyl group, dibromomethyl group, difluoromethyl group, trichloromethyl group, tribromomethyl group, trifluoromethyl group, 2,2,2-trifluoroethyl group pentafluoroethyl group, heptafluoropropyl group, and nonafluorobutyl group.

Examples of the "$C_{1-6}$ alkoxy group" include, for example, n-pentyloxy group, isopentyloxy group, neopentyloxy group, tert-pentyloxy group, 1-ethylpropoxy group, n-hexyloxy group, cyclopentyloxy group and cyclohexyloxy group, besides $C_{1-4}$ alkoxy groups such as methoxy group, ethoxy group, n-propoxy group, isopropoxy group, n-butoxy group, isobutoxyl group, sec-butoxy group, tert-butoxy group, cyclopropoxy group, cyclobutoxy group and (cyclopropyl)methoxy group.

Examples of the "halogenated $C_{1-6}$ alkoxy group" include, for example, perfluoropentyloxy group and perfluorohexyloxy group, besides halogenated $C_{1-4}$ alkoxy groups such as chloromethoxy group, bromomethoxy group, fluoromethoxy group, dichloromethoxy group, dibromomethoxy group, difluoromethoxy group, trichloromethoxy group, tribromomethoxy group, trifluoromethoxy group, 2,2,2-trifluoroethoxy group pentafluoroethoxy group, heptafluoropropoxy group, and nonafluorobutoxy group.

Examples of the "$C_{6-10}$ aryl group" include, for example, phenyl group, 1-naphthyl group and 2-naphthyl group.

Examples of the "$C_{1-6}$ alkylsulfanyl group" include, for example, n-pentylsulfanyl group, isopentylsulfanyl group, neopentylsulfanyl group, tert-pentylsulfanyl group, 1-ethylpropylsulfanyl group, n-hexylsulfanyl group, cyclopentylsulfanyl group and cyclohexylsulfanyl group, besides $C_{1-4}$ alkylsulfanyl groups such as methylsulfanyl group, ethylsulfanyl group, n-propylsulfanyl group, isopropylsulfanyl group, n-butylsulfanyl group, isobutylsulfanyl group, sec-butylsulfanyl group, tert-butylsulfanyl group, cyclopropylsulfanyl group, cyclobutylsulfanyl group and (cyclopropyl)methylsulfanyl group.

Examples of the "$C_{1-6}$ alkylenedioxy group" include, for example, 1,5-pentylenedioxy group, 1,6-hexylenedioxy group and 1,1,2,2-tetramethylethylenedioxy group, besides $C_{1-4}$ alkylenedioxy groups such as methylenedioxy group, 1,2-ethylenedioxy group, 1,3-propylenedioxy group, 1,4-butylenedioxy group and 1,1-dimethylmethylenedioxy group.

Examples of the "$C_{7-12}$ aralkyl group" include, for example, benzyl group, 1-phenethyl group, 2-phenethyl group, (naphthalen-1-yl)methyl group, (naphthalen-2-yl)methyl group, 1-(naphthalen-1-yl)ethyl group, 2-(naphthalen-1-yl)ethyl group, 1-(naphthalen-2-yl)ethyl group and 2-(naphthalen-2-yl)ethyl group.

$R^1$ represents a $C_{6-10}$ aryl group or a substituted $C_{6-10}$ aryl group.

In the present specification, when a certain functional group is defined as "substituted", kinds, numbers, and positions of substituents existing in the functional groups are not particularly limited unless otherwise specifically referred to, and when the number of the substituents is two or more, their substituents may be the same or different. Examples of these substituents include, for example, halogen atoms, cyano group, nitro group, hydroxy group, sulfanyl group, a $C_{1-6}$ alkyl group, a $C_{3-7}$ cycloalkyl group (for example, cyclopropyl group), a $C_{1-6}$ alkylene group (for example, methylene group and ethylene group), a $C_{2-6}$ alkenyl group (for example, vinyl group and allyl group), a $C_{2-6}$ alkynyl group (for example, ethynyl group and propargyl group), a $C_{6-10}$ aryl group, a $C_{7-12}$ aralkyl group (for example, benzyl group and naphthylmethyl group), a $C_{1-6}$ alkoxy group, a $C_{3-7}$ cycloalkoxy group (for example, cyclopropyloxy group), a $C_{1-6}$ alkylenedioxy group (for example, methylenedioxy group and ethylenedioxy group), a $C_{2-6}$ alkenyloxy group (for example, allyloxy group), a $C_{2-6}$ alkynyloxy group (for example, propargyloxy group), a $C_{6-10}$ aryloxy group (for example, phenoxy group and naphthyloxy group), a $C_{7-12}$ aralkyloxy group (for example, benzyloxy group), formyl group, a $C_{2-7}$ alkanoyl group (for example, acetyl group, propionyl group and pivaloyl group), a $C_{7-11}$ aroyl group (for example, benzoyl group and naphthoyl group), carboxy group, a $C_{2-7}$ alkoxycarbonyl group (for example, methoxycarbonyl group and ethoxycarbonyl group), carbamoyl group, a $C_{1-6}$ alkylsulfanyl group (for example, methylsulfanyl group), a $C_{6-10}$ arylsulfanyl group (for example, phenylsulfanyl group), a $C_{7-12}$ aralkylsulfanyl group (for example, benzylsulfanyl group), sulfo group, a $C_{1-6}$ alkylsulfonyl group (for example, methanesulfonyl group), a $C_{6-10}$ arylsulfonyl group (for example, benzenesulfonyl group), sulfamoyl group, amino group, a $C_{1-6}$ alkylamino group (for example, methylamino group), a di-$C_{1-6}$ alkylamino group (for example, dimethylamino group), formylamino group, a $C_{2-7}$ alkanoylamino group (for example, acetylamino group), a $C_{7-11}$ aroylamino group (for example, benzoylamino group), a $C_{2-7}$ alkoxycarbonylamino group (for example, methoxycarbonylamino group), a $C_{1-6}$ alkylsulfonylamino group (for example, methanesulfonylamino group), a $C_{6-10}$ arylsulfonylamino group (for example, benzenesulfonylamino group), amidino group, guanidino group, oxo group, thioxo group, a 3 to 14-membered heterocyclic group (for example, a 5 to 14-membered heteroaryl group such as furyl group, thienyl group, pyrrolyl group, isoxazolyl group, isothiazolyl group, pyrazolyl group, oxazolyl group, thiazolyl group, imidazolyl group, pyridyl group, pyrimidinyl group, pyrazinyl group, pyridazinyl group, benzo[b]furyl group, benzo[b]thienyl group, indolizinyl group, indolyl group, isoindolyl group, indazolyl group, purinyl group, quinolyl group, isoquinolyl group, naphthyridinyl group, quinoxalinyl group, quinazolinyl group, cinnolinyl group, pteridinyl group, carbazolyl group, β-carbolinyl group, phenoxazinyl group and phenothiazinyl group; a 5 to 10-membered partly saturated heterocyclic group such as pyrrolinyl group, imidazolinyl group, pyrazolinyl group, chromanyl group, isochromanyl group, indolinyl group, isoindolinyl group, tetrahydroquinolyl group and tetrahydroisoquinolyl group; and a 3 to 7-membered completely saturated heterocyclic group such as aziridinyl group, azetidinyl group, pyrrolidinyl group, imidazolidinyl group, pyrazolidinyl group, oxazolidinyl group, thiazolidinyl group, piperidinyl group, piperazinyl group, morpholinyl group, thiomorpholinyl group, azepanyl group, 1,4-diazepanyl group, 1,4-oxazepanyl group, 1,4-thiazepanyl group, tetrahydrofuranyl group, tetrahydrothiophenyl group, tetrahydropyranyl group and tetrahydrothiopyranyl group). These substituents may further be substituted with the aforementioned substituents. Examples of these substituents include, for example, a halogenated $C_{1-6}$ alkyl group, a halogenated $C_{1-6}$ alkoxy group, a $C_{3-7}$ cycloalkyl substituted $C_{1-6}$ alkyl group (for example, cyclopropylmethyl group), a hydroxy substituted $C_{1-6}$ alkyl group (for example, hydroxymethyl group), a carboxy substituted $C_{1-6}$ alkyl group (for example, carboxymethyl group).

$R^1$ is preferably a $C_{6-10}$ aryl group; a $C_{6-10}$ aryl group substituted with a group or groups selected from the group consisting of a halogen atom, nitro group, a $C_{1-6}$ alkyl group, a halogenated $C_{1-6}$ alkyl group, a $C_{1-6}$ alkoxy group, a halogenated $C_{1-6}$ alkoxy group, a $C_{1-6}$ alkylenedioxy group, a $C_{1-6}$ alkylsulfanyl group, carboxy group and amino group.

When $R^1$ is a $C_{6-10}$ aryl group substituted with a group selected from a group or groups selected from the group consisting of a halogen atom, nitro group, a $C_{1-6}$ alkyl group, a halogenated $C_{1-6}$ alkyl group, a $C_{1-6}$ alkoxy group, a halogenated $C_{1-6}$ alkoxy group, a $C_{1-6}$ alkylenedioxy group, a $C_{1-6}$ alkylsulfanyl group, carboxy group and amino group, the number of the said substituents may be one to five. Furthermore, when the number of the said substituents is two or more, their substituents may be the same or different.

$R^1$ is preferably a group represented by the following formula (II):

[Chemical formula 2]

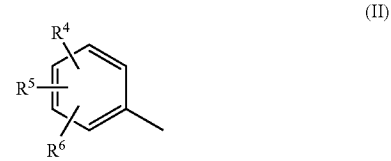

(II)

wherein $R^4$, $R^5$ and $R^6$ independently represent hydrogen atom, a halogen atom, nitro group, a $C_{1-4}$ alkyl group, a halogenated $C_{1-4}$ alkyl group, a $C_{1-4}$ alkoxy group, a halogenated $C_{1-4}$ alkoxy group, a $C_{1-4}$ alkylsulfanyl group, carboxy group or amino group, or $R^4$ binds to $R^5$ to represent a $C_{1-4}$ alkylenedioxy group.

$R^4$, $R^5$ and $R^6$ are preferably the following (a) or (b).
(a) $R^4$ is hydrogen atom, a halogen atom, nitro group, a $C_{1-4}$ alkyl group, a halogenated $C_{1-4}$ alkyl group, a $C_{1-4}$ alkoxy group, a halogenated $C_{1-4}$ alkoxy group, a $C_{1-4}$ alkylsulfanyl group, carboxy group or amino group, and $R^5$ and $R^6$ are hydrogen atoms.
(b) $R^4$ binds to $R^5$ to be a $C_{1-4}$ alkylenedioxy group, and $R^6$ is hydrogen atom.

$R^1$ is preferably any one of the following groups.

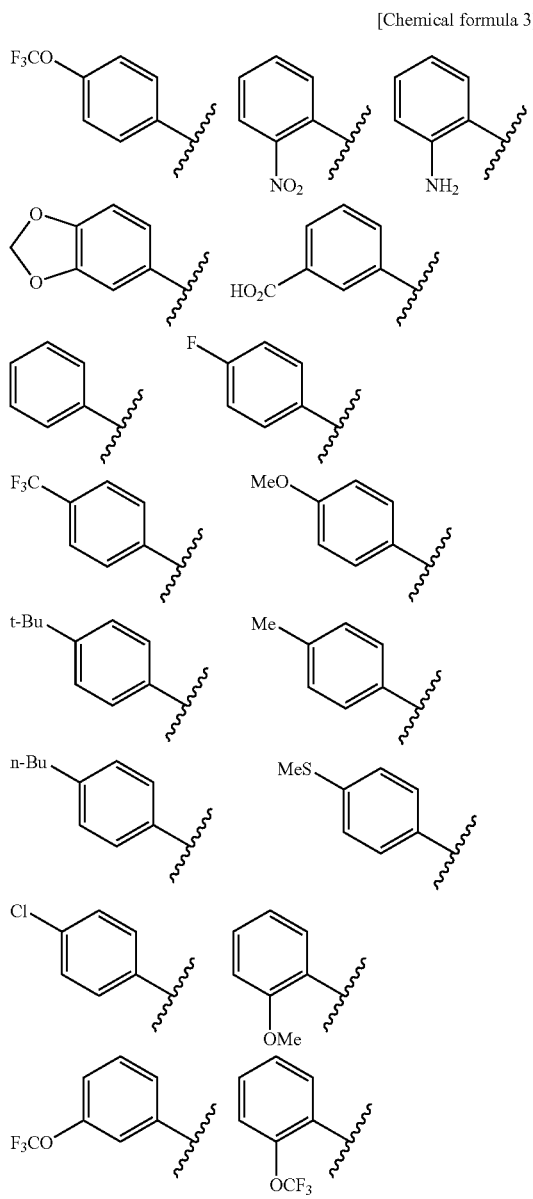

$R^2$ represents a $C_{6-10}$ aryl group or a substituted $C_{6-10}$ aryl group.

$R^2$ is preferably a $C_{6-10}$ aryl group; or a $C_{6-10}$ aryl group substituted with a group or groups selected from the group consisting of a halogen atom, nitro group, a $C_{1-6}$ alkyl group, a halogenated $C_{1-6}$ alkyl group, a $C_{1-6}$ alkoxy group, a halogenated $C_{1-6}$ alkoxy group, a phenyl group and carboxy group.

When $R^2$ is a $C_{6-10}$ aryl group substituted with a group or groups selected from the group consisting of a halogen atom, nitro group, a $C_{1-6}$ alkyl group, a halogenated $C_{1-6}$ alkyl group, a $C_{1-6}$ alkoxy group, a halogenated $C_{1-6}$ alkoxy group, a phenyl group and carboxy group, the number of the said substituents may be one to five. Furthermore, when the number of the said substituents is two or more, their substituents may be the same or different.

$R^2$ is preferably a group represented by the following formula (III):

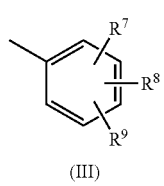

wherein $R^7$, $R^8$ and $R^9$ independently represent hydrogen atom, a halogen atom, nitro group, a $C_{1-4}$ alkyl group, a halogenated $C_{1-4}$ alkyl group, a $C_{1-4}$ alkoxy group, a halogenated $C_{1-4}$ alkoxy group, a phenyl group or carboxy group.

$R^7$, $R^8$ and $R^9$ are preferably the following (a).

(a) $R^7$ and $R^8$ are independently hydrogen atom, a halogen atom, nitro group, a $C_{1-4}$ alkyl group, a halogenated $C_{1-4}$ alkyl group, a $C_{1-4}$ alkoxy group, a halogenated $C_{1-4}$ alkoxy group, a $C_{6-10}$ aryl group or carboxy group, and $R^9$ is hydrogen atom.

$R^2$ is preferably any one of the following groups.

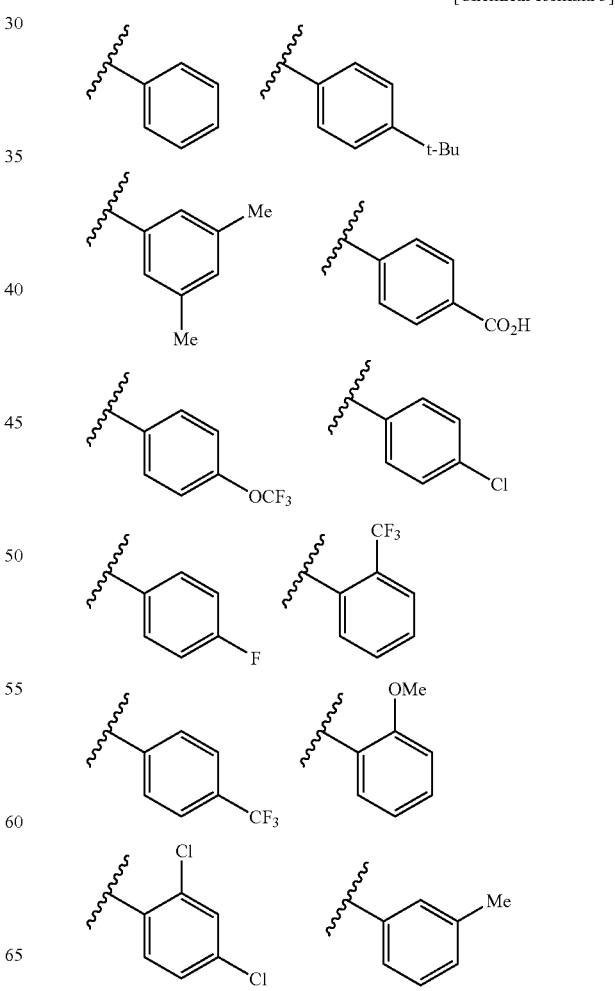

-continued

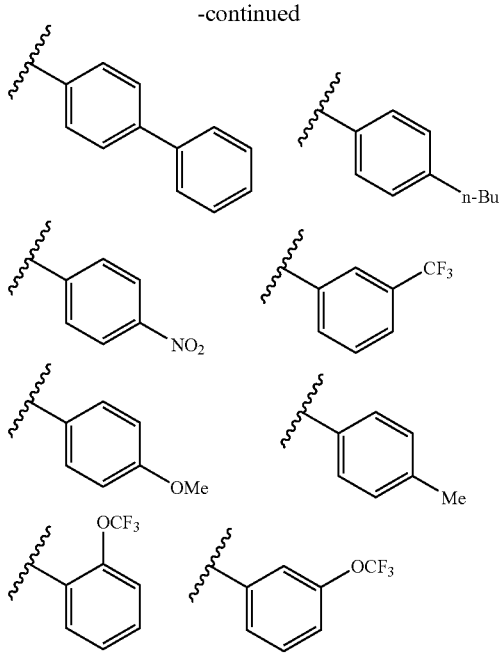

X represents —CH$_2$—, —CH$_2$CH$_2$—, —CH═CH— or —N(R$^3$)—C(═O)— wherein the nitrogen atom binds to the benzene ring and the carbon atom binds to Y.

X is preferably —CH$_2$—, —CH$_2$CH$_2$— or —N(R$^3$)—C(═O)— wherein the nitrogen atom binds to the benzene ring and the carbon atom binds to Y.

X is preferably —CH$_2$CH$_2$—.

Y represents carboxy group or a bioisostere of carboxy group.

The term "bioisostere" means compounds or groups that possess near equal molecular shapes and volumes, approximately the same distribution of electrons, and which exhibit similar physical and biological properties. As the bioisostere of carboxy group, specific groups are described, for example, in the following documents.

Ann. Rep. Med. Chem., vol. 21, pp. 283-291 (1986).

Chem. Rev., vol. 96, pp. 3147-3176 (1996).

When Y is a bioisostere of carboxy group, the said bioisostere of carboxy group is preferably 1H-tetrazol-5-yl group.

Y is preferably carboxy group.

R$^3$ represents hydrogen atom, a C$_{1-4}$ alkyl group or a C$_{7-12}$ aralkyl group.

R$^3$ is preferably hydrogen atom, a C$_{1-4}$ alkyl group or a benzyl group.

m represents 0 or 1.

The compounds represented by the aforementioned formula (I) may form salts. Examples of pharmacologically acceptable salts include, when acidic groups exist, metal salts such as lithium salt, sodium salt, potassium salt, magnesium salt, calcium salts, or ammonium salts such as ammonium salt, methylammonium salt, dimethylammonium salt, trimethylammonium salt, dicyclohexylammonium salt, and when basic groups exist, mineral acid salts such as hydrochloride, hydrobromide (salt of hydrobromic acid), hydrosulfate, nitrate, phosphate, or organic acid salts such as methane sulfonate, benzene sulfonate, para-toluene sulfonate, acetate, propionate, tartrate, fumarate, maleate, malate, oxalate, succinate, citrate, benzoate, mandelate, cinnamate, lactate. Salts may sometimes be formed with amino acids such as glycine. As active ingredients of the medicament of the present invention, pharmacologically acceptable salts may also be suitably used.

The compounds or salts thereof represented by the aforementioned formula (I) may exist as hydrates or solvates. As active ingredients of the medicament of the present invention, any of the aforementioned substances may be used. Furthermore, the compounds represented by the aforementioned formula (I) may sometimes have one or more asymmetric carbons, and may exist as steric isomers such as optically active substance and diastereomer. As active ingredients of the medicament of the present invention, pure forms of stereoisomers, arbitrary mixture of enantiomers or diastereomers, and racemates may be used.

Furthermore, when the compounds represented by the aforementioned formula (I) may exist as a tautomer. As active ingredients of the medicament of the present invention, pure forms of tautomers or a mixture thereof may be used. When the compounds represented by the aforementioned formula (I) have olefinic double bonds, the configuration may be in either E or Z, and as active ingredients of the medicament of the present invention, geometrical isomer in either of the configurations or a mixture thereof may be used.

Examples of the preferred compounds as active ingredients of the medicaments of the present invention are shown below. However, the active ingredients of the medicaments of the present invention are not limited to the following compounds. The abbreviations used in the following tables have the following meanings. Me: methyl group, n-Bu: n-butyl group, t-Bu: tert-butyl group, OMe: methoxy group, SMe: methylsulfanyl group.

TABLE 1

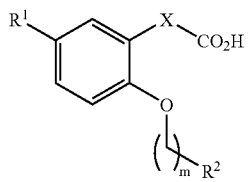

| Compound Number | R$^1$ | R$^2$ | X | m |
|---|---|---|---|---|
| 1 | F$_3$CO-(phenyl)- | -(phenyl) | —CH$_2$— | 1 |

TABLE 1-continued

| Compound Number | R¹ | R² | X | m |
|---|---|---|---|---|
| 2 | 4-F₃CO-C₆H₄- | C₆H₅- | —CH=CH— (E form) | 1 |
| 3 | 4-F₃CO-C₆H₄- | C₆H₅- | —CH₂CH₂— | 1 |
| 4 | 4-F₃CO-C₆H₄- | 4-t-Bu-C₆H₄- | —CH=CH— (E form) | 1 |
| 5 | 4-F₃CO-C₆H₄- | 4-t-Bu-C₆H₄- | —CH₂CH₂— | 1 |
| 6 | 4-F₃CO-C₆H₄- | 4-t-Bu-C₆H₄- | —NH—C(=O)—CH₂— | 1 |
| 7 | 2-NO₂-C₆H₄- | C₆H₅- | —CH=CH— (E form) | 1 |
| 8 | 2-NH₂-C₆H₄- | C₆H₅- | —CH₂CH₂— | 1 |
| 9 | 4-F₃CO-C₆H₄- | 4-t-Bu-C₆H₄- | —CH₂— | 1 |
| 10 | 3,4-methylenedioxyphenyl | 4-t-Bu-C₆H₄- | —CH₂— | 1 |
| 11 | 4-F₃CO-C₆H₄- | 3,5-di-Me-C₆H₃- | —CH₂— | 1 |

TABLE 1-continued
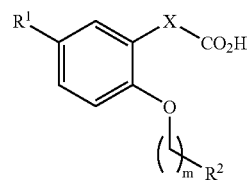
| Compound Number | R¹ | R² | X | m |
|---|---|---|---|---|
| 12 | F₃CO-C₆H₄- | 4-t-Bu-C₆H₄- | —CH=CH— (Z form) | 0 |
| 13 | F₃CO-C₆H₄- | 4-t-Bu-C₆H₄- | —CH₂CH₂— | 0 |
| 14 | F₃CO-C₆H₄- | 4-CO₂H-C₆H₄- | —CH=CH— (Z form) | 0 |
| 15 | F₃CO-C₆H₄- | 4-CO₂H-C₆H₄- | —CH₂CH₂— | 0 |
| 16 | F₃CO-C₆H₄- | 4-OCF₃-C₆H₄- | —CH=CH— (E form) | 0 |
| 17 | F₃CO-C₆H₄- | 4-OCF₃-C₆H₄- | —CH₂CH₂— | 0 |
| 18 | F₃CO-C₆H₄- | 4-t-Bu-C₆H₄- | —N(Me)C(=O)CH₂— | 1 |
| 19 | F₃CO-C₆H₄- | 4-Cl-C₆H₄- | —CH=CH— (E form) | 1 |
| 20 | F₃CO-C₆H₄- | 4-Cl-C₆H₄- | —CH₂CH₂— | 1 |
| 21 | F₃CO-C₆H₄- | 4-F-C₆H₄- | —CH=CH— (E form) | 1 |
| 22 | F₃CO-C₆H₄- | 4-F-C₆H₄- | —CH₂CH₂— | 1 |

TABLE 1-continued

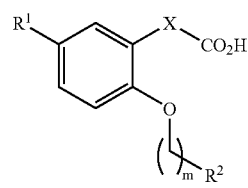

| Compound Number | R¹ | R² | X | m |
|---|---|---|---|---|
| 23 | F₃CO-（p-phenyl） | 2-CF₃-phenyl | —CH=CH— (E form) | 1 |
| 24 | F₃CO-（p-phenyl） | 2-CF₃-phenyl | —CH₂CH₂— | 1 |
| 25 | F₃CO-（p-phenyl） | 4-CF₃-phenyl | —CH=CH— (E form) | 1 |
| 26 | F₃CO-（p-phenyl） | 4-CF₃-phenyl | —CH₂CH₂— | 1 |
| 27 | F₃CO-（p-phenyl） | 2-OMe-phenyl | —CH=CH— (E form) | 1 |
| 28 | F₃CO-（p-phenyl） | 2-OMe-phenyl | —CH₂CH₂— | 1 |
| 29 | F₃CO-（p-phenyl） | phenyl | —CH=CH— (Z form) | 1 |
| 30 | F₃CO-（p-phenyl） | 4-t-Bu-phenyl | —CH=CH— (Z form) | 1 |
| 31 | 3-HO₂C-phenyl | 4-t-Bu-phenyl | —CH₂CH₂— | 1 |
| 32 | F₃CO-（p-phenyl） | 2,4-diCl-phenyl | —CH₂CH₂— | 1 |

TABLE 1-continued
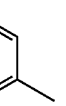
| Compound Number | R¹ | R² | X | m |
|---|---|---|---|---|
| 33 | 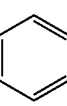 F₃CO | 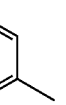 Me | —CH₂CH₂— | 1 |
| 34 | 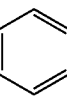 F₃CO | 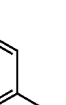 | —CH₂CH₂— | 1 |
| 35 | 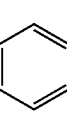 F₃CO |  n-Bu | —CH₂CH₂— | 1 |
| 36 | 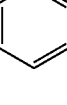 |  t-Bu | —CH=CH— (E form) | 1 |
| 37 | 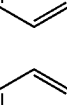 |  t-Bu | —CH₂CH₂— | 1 |
| 38 | 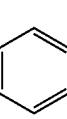 F | 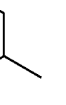 t-Bu | —CH=CH— (E form) | 1 |
| 39 | 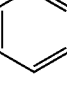 F | 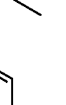 t-Bu | —CH₂CH₂— | 1 |
| 40 | 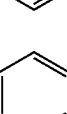 F₃C | 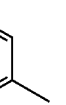 t-Bu | —CH=CH— (E form) | 1 |
| 41 | 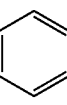 F₃C | 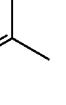 t-Bu | —CH₂CH₂— | 1 |
| 42 | 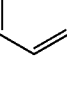 MeO |  t-Bu | —CH=CH— (E form) | 1 |
| 43 | MeO  | t-Bu | —CH₂CH₂— | 1 |

TABLE 1-continued
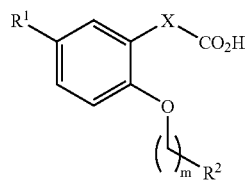
| Compound Number | R¹ | R² | X | m |
|---|---|---|---|---|
| 44 | t-Bu–C₆H₄– | –C₆H₄–t-Bu | —CH=CH— (E form) | 1 |
| 45 | t-Bu–C₆H₄– | –C₆H₄–t-Bu | —CH₂CH₂— | 1 |
| 46 | Me–C₆H₄– | –C₆H₄–t-Bu | —CH=CH— (E form) | 1 |
| 47 | Me–C₆H₄– | –C₆H₄–t-Bu | —CH₂CH₂— | 1 |
| 48 | n-Bu–C₆H₄– | –C₆H₄–t-Bu | —CH₂CH₂— | 1 |
| 49 | MeS–C₆H₄– | –C₆H₄–t-Bu | —CH=CH— (E form) | 1 |
| 50 | C₆H₅– | –C₆H₅ | —CH=CH— (E form) | 1 |
| 51 | C₆H₅– | –C₆H₅ | —CH₂CH₂— | 1 |
| 52 | t-Bu–C₆H₄– | –C₆H₅ | —CH=CH— (E form) | 1 |
| 53 | t-Bu–C₆H₄– | –C₆H₅ | —CH₂CH₂— | 1 |
| 54 | Cl–C₆H₄– | –C₆H₄–t-Bu | —CH=CH— (E form) | 1 |
| 55 | Cl–C₆H₄– | –C₆H₄–t-Bu | —CH₂CH₂— | 1 |

TABLE 1-continued

| Compound Number | R¹ | R² | X | m |
|---|---|---|---|---|
| 56 | 4-t-Bu-phenyl | 4-OCF₃-phenyl | —CH=CH— (E form) | 1 |
| 57 | 4-t-Bu-phenyl | 4-OCF₃-phenyl | —CH₂CH₂— | 1 |
| 58 | phenyl | 4-OCF₃-phenyl | —CH₂CH₂— | 1 |
| 59 | 4-F₃CO-phenyl | 4-t-Bu-phenyl | —N(CH₂Ph)C(=O)— | 1 |
| 60 | 4-F₃CO-phenyl | 4-NO₂-phenyl | —CH₂CH₂— | 1 |
| 61 | 2-OMe-phenyl | 4-t-Bu-phenyl | —CH=CH— (E form) | 1 |
| 62 | 2-OMe-phenyl | 4-t-Bu-phenyl | —CH₂CH₂— | 1 |
| 63 | 4-F₃CO-phenyl | 3-CF₃-phenyl | —CH=CH— (E form) | 1 |
| 64 | 4-F₃CO-phenyl | 3-CF₃-phenyl | —CH₂CH₂— | 1 |
| 65 | 4-F₃CO-phenyl | 3,5-diMe-phenyl | —CH₂CH₂— | 1 |

TABLE 1-continued
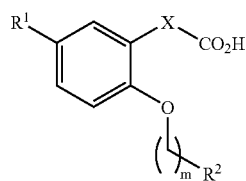
| Compound Number | R¹ | R² | X | m |
|---|---|---|---|---|
| 66 | 4-F₃CO-C₆H₄- | 4-MeO-C₆H₄- | —CH₂CH₂— | 1 |
| 67 | 4-F₃CO-C₆H₄- | 4-Me-C₆H₄- | —CH₂CH₂— | 1 |
| 68 | 4-F₃CO-C₆H₄- | 4-F₃CO-C₆H₄- | —CH₂CH₂— | 1 |
| 70 | 3-F₃CO-C₆H₄- | 4-t-Bu-C₆H₄- | —CH=CH— (E form) | 1 |
| 71 | 3-F₃CO-C₆H₄- | 4-t-Bu-C₆H₄- | —CH₂CH₂— | 1 |
| 72 | 2-F₃CO-C₆H₄- | 4-t-Bu-C₆H₄- | —CH=CH— (E form) | 1 |
| 73 | 2-F₃CO-C₆H₄- | 4-t-Bu-C₆H₄- | —CH₂CH₂— | 1 |
| 74 | 4-t-Bu-C₆H₄- | 2-F₃CO-C₆H₄- | —CH₂CH₂— | 1 |
| 75 | 4-t-Bu-C₆H₄- | 3-F₃CO-C₆H₄- | —CH₂CH₂— | 1 |
| 76 | 4-t-Bu-C₆H₄- | 4-Cl-C₆H₄- | —CH₂CH₂— | 1 |

TABLE 1-continued

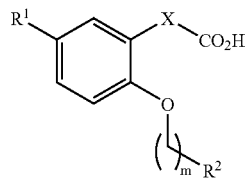

| Compound Number | R¹ | R² | X | m |
|---|---|---|---|---|
| 77 | t-Bu-C₆H₄- | 4-CF₃-C₆H₄- | —CH₂CH₂— | 1 |
| 78 | t-Bu-C₆H₄- | 4-n-Bu-C₆H₄- | —CH₂CH₂— | 1 |

※ Compound No. 6: sodium salt

TABLE 2

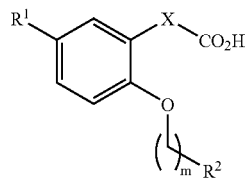

| Compound Number | R¹ | R² | —X—Y | m |
|---|---|---|---|---|
| 69 | F₃CO-C₆H₄- | 4-t-Bu-C₆H₄- | —CH₂CH₂-(1H-tetrazol-5-yl) | 1 |

The compounds represented by the general formula (I) can be prepared, for example, by methods shown below.

The compounds represented by the general formula (I), wherein X is —CH₂—, m is 1, can be prepared, for example, by a method shown below.

<Scheme 1>

[Chemical formula 6]

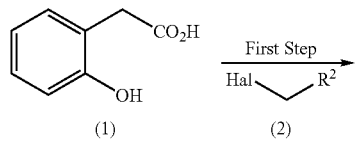

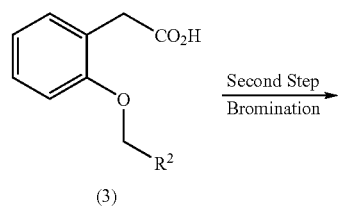

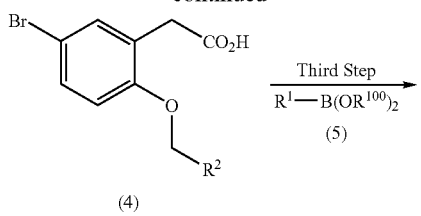

wherein Hal represents a halogen atom; $R^{100}$ represents hydrogen atom, a $C_{1-4}$ alkyl group or the like; each of $R^1$ and $R^2$ has the same meanings as that described above.

<First Step>

The 2-(aralkyloxy)phenyl acetic acid derivative (3) can be prepared by reacting the 2-hydroxyphenylacetic acid (1) with the aralkyl halide derivative (2). This reaction is carried out in a solvent, in the presence of a base, at a reaction temperature of from 0° C. to 180° C., preferably at a temperature of from 0° C. to the boiling point of the solvent.

As the base, examples include inorganic bases such as sodium hydride, potassium hydride, potassium carbonate, sodium carbonate and sodium hydrogencarbonate; and organic bases such as triethylamine and diisopropylethylamine. Excessive amounts of base may preferably be used.

As the solvent, any solvent can be used as long as it does not inhibit the reaction, and examples include, for example, halogenated solvents such as dichloromethane, dichloroethane and chloroform; ethers such as tetrahydrofuran, 1,2-dimethoxyethane and 1,4-dioxane; amides such as dimethylformamide and N-methylpyrrolidone; aromatic solvents such as benzene and toluene; ketones such as acetone and 2-butanone; or a mixed solvent thereof.

<Second Step>

The 2-aralkyloxy-5-bromophenyl acetic acid derivative (4) can be prepared by brominating the 2-(aralkyloxy)phenyl acetic acid derivative (3) obtained in the first step. This reaction is carried out in a solvent, in the presence of a brominating agent, at a reaction temperature of from 0° C. to 180° C., preferably at a temperature of from 0° C. to the boiling point of the solvent.

As the brominating agent, examples include, for example, N-bromosuccinimide and the like.

As the solvent, any solvent can be used as long as it does not inhibit the reaction, and examples include, for example, halogenated solvents such as dichloromethane, dichloroethane and chloroform; or a mixed solvent thereof.

<Third Step>

The final target compound (6) can be prepared by reacting the 2-aralkyloxy-5-bromophenyl acetic acid derivatives (4) obtained in the second step with the arylboronic acid derivative (5). This reaction is carried out in a solvent, in the presence of a catalytic amount of a transition metal complex, in the presence or absence of a base, at a reaction temperature of from 0° C. to 180° C., preferably at a temperature of from 0° C. to the boiling point of the solvent.

As the transition metal complex, examples include, for example, [1,1-bis(diphenylphosphino)ferrocene]dichloropalladium (II), tetrakis(triphenylphosphine)palladium and the like.

As the base, examples include inorganic bases such as potassium carbonate, sodium carbonate and sodium hydrogencarbonate; and organic bases such as triethylamine and diisopropylethylamine.

As the solvent, any solvent can be used as long as it does not inhibit the reaction, and examples include, for example, ethers such as tetrahydrofuran, 1,2-dimethoxyethane and 1,4-dioxane; amides such as dimethylformamide and N-methylpyrrolidone; aromatic solvents such as benzene and toluene; alcohols such as methanol and ethanol; water; or a mixed solvent thereof.

In the compounds represented by the general formula (I), the compounds wherein X is —CH$_2$— and m is 0 can be prepared, for example, by using the aryl halide derivative (Hal-R$^2$) instead of the aralkyl halide derivative (2) in scheme 1.

The compounds represented by the general formula (I), wherein X is —CH=CH—, m is 1, can be prepared, for example, by a method shown below.

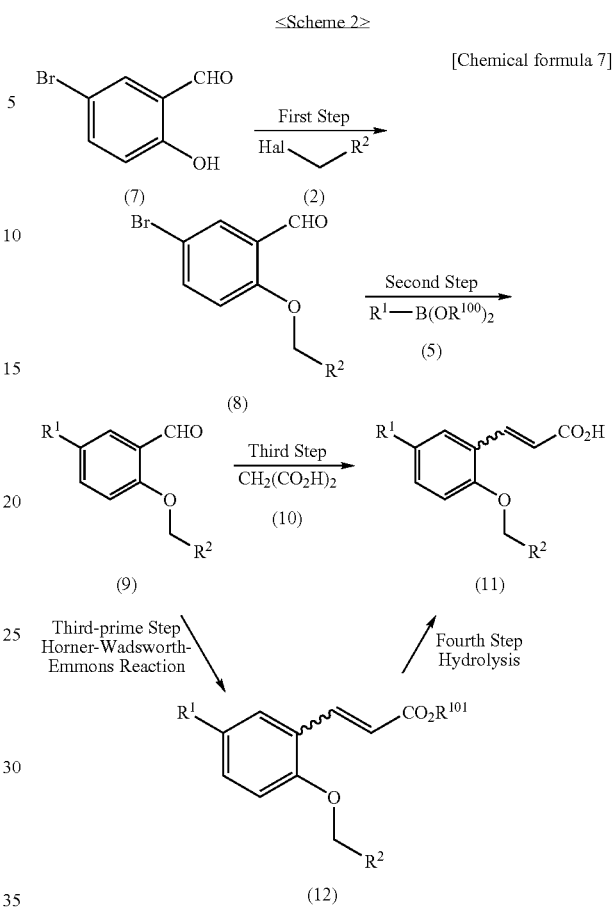

<Scheme 2>

[Chemical formula 7]

wherein Hal represents a halogen atom; R$^{100}$ represents hydrogen atom, a C$_{1-4}$ alkyl group or the like; R$^{101}$ represents a C$_{1-4}$ alkyl group or the like; each of R$^1$ and R$^2$ has the same meanings as that described above.

<First Step>

The 2-aralkyloxy-5-bromobenzaldehyde derivative (8) can be prepared by reacting the 5-bromosalicylaldehyde (7) with the aralkyl halide derivative (2). This reaction is carried out in a solvent, in the presence of a base, at a reaction temperature of from 0° C. to 180° C., preferably at a temperature of from 0° C. to the boiling point of the solvent.

As the base, examples include inorganic bases such as sodium hydride, potassium hydride, potassium carbonate, sodium carbonate and sodium hydrogencarbonate; and organic bases such as triethylamine and diisopropylethylamine.

As the solvent, any solvent can be used as long as it does not inhibit the reaction, and examples include, for example, halogenated solvents such as dichloromethane, dichloroethane and chloroform; ethers such as tetrahydrofuran, 1,2-dimethoxyethane and 1,4-dioxane; amides such as dimethylformamide and N-methylpyrrolidone; aromatic solvents such as benzene and toluene; ketones such as acetone and 2-butanone; or a mixed solvent thereof.

<Second Step>

The 5-aryl-2-(aralkyloxy)benzaldehyde derivative (9) can be prepared by reacting the 2-aralkyloxy-5-bromobenzaldehyde derivative (8) obtained in the first step with the arylboronic acid derivative (5). This reaction is carried out in a solvent, in the presence of a catalytic amount of a transition metal complex, in the presence or absence of a base, at a reaction temperature of from 0° C. to 180° C., preferably at a temperature of from 0° C. to the boiling point of the solvent.

As the transition metal complex, examples include, for example, [1,1-bis(diphenylphosphino)ferrocene]dichloropalladium (II), tetrakis(triphenylphosphine)palladium and the like.

As the base, examples include inorganic bases such as potassium carbonate, sodium carbonate and sodium hydrogencarbonate; and organic bases such as triethylamine and diisopropylethylamine.

As the solvent, any solvent can be used as long as it does not inhibit the reaction, and examples include, for example, ethers such as tetrahydrofuran, 1,2-dimethoxyethane and 1,4-dioxane; amides such as dimethylformamide and N-methylpyrrolidone; aromatic solvents such as benzene and toluene; alcohols such as methanol and ethanol; water; or a mixed solvent thereof.

<Third Step>

The final target compound (11) can be prepared by reacting the 5-aryl-2-(aralkyloxy)benzaldehyde derivative (9) obtained in the second step with malonic acid (10). This reaction is carried out without solvent or in a solvent, in the presence of a catalytic amount of an amine, in the presence or absence of a base, at a reaction temperature of from 0° C. to 180° C., preferably at a temperature of from 0° C. to the boiling point of the solvent.

As the amine, examples include, for example, piperidine and the like.

As the base, examples include, for example, organic bases such as pyridine, triethylamine and diisopropylethylamine.

As the solvent, any solvent can be used as long as it does not inhibit the reaction, and examples include, for example, alcohols such as methanol and ethanol; or a mixed solvent thereof.

<Third-prime Step>

The 3-[5-aryl-2-(aralkyloxy)phenyl]propenoic acid ester derivative (12) can be prepared by reacting the 5-aryl-2-(aralkyloxy)benzaldehyde derivative (9) obtained in the second step with the triester of phosphonoacetic acid. This reaction is known as the "Horner-Wadsworth-Emmons Reaction" and carried out in a solvent, in the presence of a base, at a reaction temperature of from 0° C. to 180° C., preferably at a temperature of from 0° C. to the boiling point of the solvent. Crown ethers such as 18-crown-6 may be added.

As the triester of phosphonoacetic acid, examples include, for example, triethyl phosphonoacetate, bis(2,2,2-trifluoroethyl) (methoxycarbonylmethyl)phosphonate and the like.

As the base, examples include inorganic bases such as sodium hydride, potassium hydride, potassium carbonate, sodium carbonate and sodium hydrogencarbonate; organic bases such as triethylamine and diisopropylethylamine; potassium bis(trimethylsilyl)amide, lithium bis(trimethylsilyl)amide, lithium diisopropylamide and the like.

As the solvent, any solvent can be used as long as it does not inhibit the reaction, and examples include, for example, ethers such as tetrahydrofuran, 1,2-dimethoxyethane and 1,4-dioxane; aromatic solvents such as benzene and toluene; or a mixed solvent thereof.

When selective preparation of the Z form of the ester derivative of 3-phenylpropenoic acid is carried out, bis(2,2,2-trifluoroethyl) (methoxycarbonylmethyl)phosphonate, potassium bis(trimethylsilyl)amide and 18-crown-6 are preferably used.

<Fourth Step>

The final target compound (II) can be prepared by the hydrolysis of the 3-[5-aryl-2-(aralkyloxy)phenyl]propenoic acid ester derivative (12) obtained in the third-prime step. This reaction is carried out in a solvent, in the presence of a base, at a reaction temperature of from 0° C. to 180° C., preferably at a temperature of from 0° C. to the boiling point of the solvent.

As the base, examples include, for example, inorganic bases such as sodium hydroxide, potassium hydroxide, potassium carbonate and sodium carbonate.

As the solvent, any solvent can be used as long as it does not inhibit the reaction, and examples include, for example, ethers such as tetrahydrofuran, 1,2-dimethoxyethane and 1,4-dioxane; alcohols such as methanol and ethanol; water; or a mixed solvent thereof.

The compounds represented by the general formula (I), wherein X is —CH=CH—, m is 0, can be prepared, for example, by a method shown below.

<Scheme 3>

[Chemical formula 8]

wherein $R^{100}$ represents hydrogen atom, a $C_{1-4}$ alkyl group or the like; $R^{101}$ represents a $C_{1-4}$ alkyl group or the like; each of $R^1$ and $R^2$ has the same meanings as that described above.

<First Step>

The 5-aryl-2-fluorobenzaldehyde derivative (14) can be prepared by reacting the 5-bromo-2-fluorobenzaldehyde (13) with the arylboronic acid derivative (5). This reaction is carried out in a solvent, in the presence of a catalytic amount of a transition metal complex, in the presence or absence of a base, at a reaction temperature of from 0° C. to 180° C., preferably at a temperature of from 0° C. to the boiling point of the solvent.

As the transition metal complex, examples include, for example, [1,1-bis(diphenylphosphino)ferrocene]dichloropalladium (II), tetrakis(triphenylphosphine)palladium and the like.

As the base, examples include inorganic bases such as potassium carbonate, sodium carbonate and sodium hydrogencarbonate; and organic bases such as triethylamine and diisopropylethylamine.

As the solvent, any solvent can be used as long as it does not inhibit the reaction, and examples include, for example, ethers such as tetrahydrofuran, 1,2-dimethoxyethane and 1,4-dioxane; amides such as dimethylformamide and N-methylpyrrolidone; aromatic solvents such as benzene and toluene; alcohols such as methanol and ethanol; water; or a mixed solvent thereof.

<Second Step>

The 5-aryl-2-(aryloxy)benzaldehyde derivative (16) can be prepared by reacting the 5-aryl-2-fluorobenzaldehyde derivative (14) obtained in the first step with the hydroxyaryl derivative (15). This reaction is carried out in a solvent, in the presence of a base, at a reaction temperature of from 0° C. to 180° C., preferably at a temperature of from 0° C. to the boiling point of the solvent.

As the base, examples include inorganic bases such as sodium hydride, potassium hydride, potassium carbonate, sodium carbonate and sodium hydrogencarbonate; and organic bases such as triethylamine and diisopropylethylamine.

As the solvent, any solvent can be used as long as it does not inhibit the reaction, and examples include, for example, ethers such as tetrahydrofuran, 1,2-dimethoxyethane and 1,4-dioxane; amides such as dimethylformamide and N-methylpyrrolidone; aromatic solvents such as benzene and toluene; or a mixed solvent thereof.

<Third Step>

The final target compound (17) can be prepared by reacting the 5-aryl-2-(aryloxy)benzaldehyde derivative (16) obtained in the second step with malonic acid (10). This reaction is carried out without solvent or in a solvent, in the presence of a catalytic amount of an amine, in the presence or absence of a base, at a reaction temperature of from 0° C. to 180° C., preferably at a temperature of from 0° C. to the boiling point of the solvent.

As the amine, examples include, for example, piperidine and the like.

As the base, examples include, for example, organic bases such as pyridine, triethylamine and diisopropylethylamine.

As the solvent, any solvent can be used as long as it does not inhibit the reaction, and examples include, for example, alcohols such as methanol and ethanol; or a mixed solvent thereof.

<Third-Prime Step>

The 3-[5-aryl-2-(aryloxy)phenyl]propenoic acid ester derivative (18) can be prepared by reacting the 5-aryl-2-(aryloxy)benzaldehyde derivative (16) obtained in the second step with the triester of phosphonoacetic acid. This reaction is known as the "Horner-Wadsworth-Emmons Reaction" and carried out in a solvent, in the presence of a base, at a reaction temperature of from −100° C. to 180° C., preferably at a temperature of from −100° C. to the boiling point of the solvent. Crown ethers such as 18-crown-6 may be added.

As the triester of phosphonoacetic acid, examples include, for example, triethyl phosphonoacetate, bis(2,2,2-trifluoroethyl) (methoxycarbonylmethyl)phosphonate and the like.

As the base, examples include inorganic bases such as sodium hydride, potassium hydride, potassium carbonate, sodium carbonate and sodium hydrogencarbonate; organic bases such as triethylamine and diisopropylethylamine; potassium bis(trimethylsilyl)amide, lithium bis(trimethylsilyl)amide, lithium diisopropylamide and the like.

As the solvent, any solvent can be used as long as it does not inhibit the reaction, and examples include, for example, ethers such as tetrahydrofuran, 1,2-dimethoxyethane and 1,4-dioxane; aromatic solvents such as benzene and toluene; or a mixed solvent thereof.

When selective preparation of the Z form of the ester derivative of 3-phenylpropenoic acid is carried out, bis(2,2,2-trifluoroethyl) (methoxycarbonylmethyl)phosphonate, potassium bis(trimethylsilyl)amide and 18-crown-6 are preferably used.

<Fourth Step>

The final target compound (17) can be prepared by the hydrolysis of the 3-[5-aryl-2-(aryloxy)phenyl]propenoic acid ester derivative (18) obtained in the third-prime step. This reaction is carried out in a solvent, in the presence of a base, at a reaction temperature of from 0° C. to 180° C., preferably at a temperature of from 0° C. to the boiling point of the solvent.

As the base, examples include, for example, inorganic bases such as sodium hydroxide, potassium hydroxide, potassium carbonate and sodium carbonate.

As the solvent, any solvent can be used as long as it does not inhibit the reaction, and examples include, for example, ethers such as tetrahydrofuran, 1,2-dimethoxyethane and 1,4-dioxane; alcohols such as methanol and ethanol; water; or a mixed solvent thereof.

When the aftertreatment is carried out under acidic condition, the free form of the carboxylic acid can be obtained. When the aftertreatment is carried out under basic condition, the salt of the carboxylic acid can be obtained.

The compounds represented by the general formula (I), wherein X is —CH=CH—, can be prepared, for example, by a method shown below.

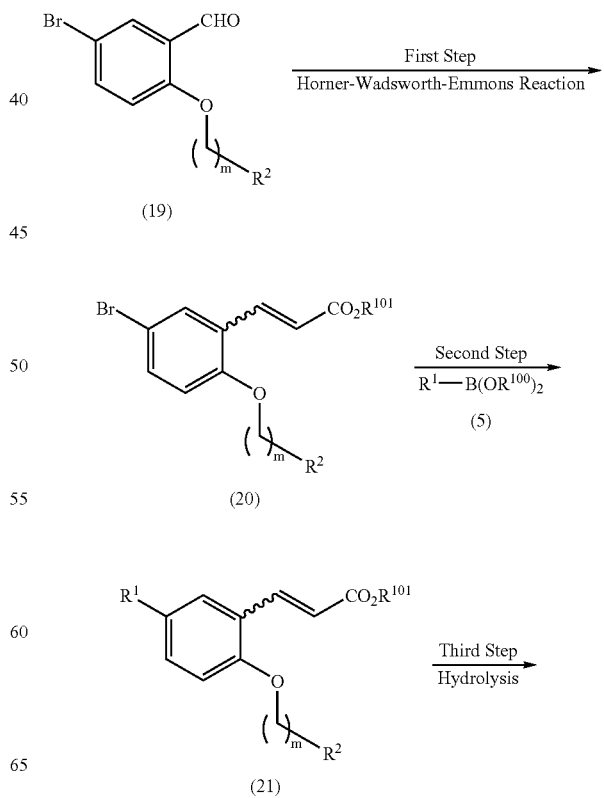

-continued

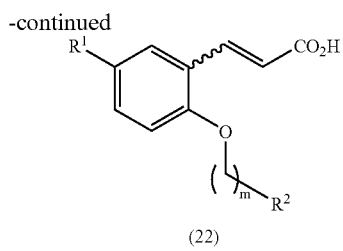

(22)

wherein $R^{100}$ represents hydrogen atom, a $C_{1-4}$ alkyl group or the like; $R^{101}$ represents a $C_{1-4}$ alkyl group or the like; each of $R^1$, $R^2$ and m has the same meanings as that described above.

<First Step>

The 3-(5-bromophenyl)propenoic acid ester derivative (20) can be prepared by reacting the 5-bromobenzaldehyde derivative (19) with the triester of phosphonoacetic acid. This reaction is known as the "Horner-Wadsworth-Emmons Reaction" and carried out in a solvent, in the presence of a base, at a reaction temperature of from −100° C. to 180° C., preferably at a temperature of from −100° C. to the boiling point of the solvent. Crown ethers such as 18-crown-6 may be added.

As the triester of phosphonoacetic acid, examples include, for example, triethyl phosphonoacetate, bis(2,2,2-trifluoroethyl) (methoxycarbonylmethyl)phosphonate and the like.

As the base, examples include inorganic bases such as sodium hydride, potassium hydride, potassium carbonate, sodium carbonate and sodium hydrogencarbonate; organic bases such as triethylamine and diisopropylethylamine; potassium bis(trimethylsilyl)amide, lithium bis(trimethylsilyl)amide, lithium diisopropylamide and the like.

As the solvent, any solvent can be used as long as it does not inhibit the reaction, and examples include, for example, ethers such as tetrahydrofuran, 1,2-dimethoxyethane and 1,4-dioxane; aromatic solvents such as benzene and toluene; or a mixed solvent thereof.

When selective preparation of the Z form of the ester derivative of 3-phenylpropenoic acid is carried out, bis(2,2,2-trifluoroethyl) (methoxycarbonylmethyl)phosphonate, potassium bis(trimethylsilyl)amide and 18-crown-6 are preferably used.

<Second Step>

The 3-(5-arylphenyl)propenoic acid ester derivative (21) can be prepared by reacting the 3-(5-bromophenyl)propenoic acid ester derivative (20) obtained in the first step with the arylboronic acid derivative (5). This reaction is carried out in a solvent, in the presence of a catalytic amount of a transition metal complex, in the presence or absence of a base, at a reaction temperature of from 0° C. to 180° C., preferably at a temperature of from 0° C. to the boiling point of the solvent.

As the transition metal complex, examples include, for example, [1,1-bis(diphenylphosphino)ferrocene]dichloropalladium (II), tetrakis(triphenylphosphine)palladium and the like.

As the base, examples include inorganic bases such as potassium carbonate, sodium carbonate and sodium hydrogencarbonate; and organic bases such as triethylamine and diisopropylethylamine.

As the solvent, any solvent can be used as long as it does not inhibit the reaction, and examples include, for example, ethers such as tetrahydrofuran, 1,2-dimethoxyethane and 1,4-dioxane; amides such as dimethylformamide and N-methylpyrrolidone; aromatic solvents such as benzene and toluene; alcohols such as methanol and ethanol; water; or a mixed solvent thereof.

<Third Step>

The final target compound (22) can be prepared by the hydrolysis of the 3-(5-arylphenyl)propenoic acid ester derivative (21) obtained in the second step. This reaction is carried out in a solvent, in the presence of a base, at a reaction temperature of from 0° C. to 180° C., preferably at a temperature of from 0° C. to the boiling point of the solvent.

As the base, examples include, for example, inorganic bases such as sodium hydroxide, potassium hydroxide, potassium carbonate and sodium carbonate.

As the solvent, any solvent can be used as long as it does not inhibit the reaction, and examples include, for example, ethers such as tetrahydrofuran, 1,2-dimethoxyethane and 1,4-dioxane; alcohols such as methanol and ethanol; water; or a mixed solvent thereof.

When the aftertreatment is carried out under acidic condition, the free form of the carboxylic acid can be obtained. When the aftertreatment is carried out under basic condition, the salt of the carboxylic acid can be obtained.

The compounds represented by the general formula (I), wherein X is —$CH_2CH_2$—, can be prepared, for example, by a method shown below.

<Scheme 5>

[Chemical formula 10]

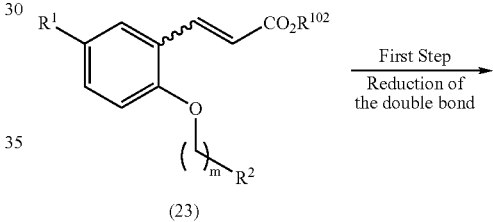

(23)

First Step
Reduction of the double bond

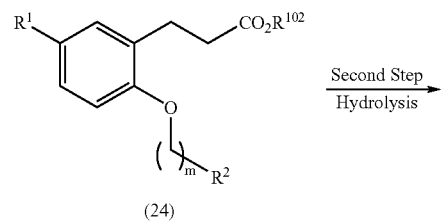

(24)

Second Step
Hydrolysis

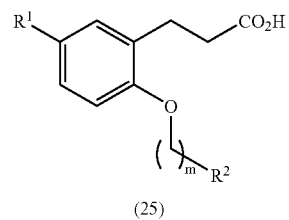

(25)

wherein $R^{102}$ represents a $C_{1-4}$ alkyl group or the like; each of $R^1$, $R^2$ and m has the same meanings as that described above.

<First Step>

The 3-(5-arylphenyl)propanoic acid ester derivative (24) can be prepared by the reduction of the double bond of the 3-(5-arylphenyl)propenoic acid ester derivative (23). This reaction is carried out in a solvent under hydrogen atmosphere, in the presence of a catalytic amount of a transition metal, at a reaction temperature of from 0° C. to 180° C., preferably at a temperature of from 0° C. to the boiling point of the solvent.

As the transition metal, examples include, for example, palladium-activated charcoal, platinum oxide and the like. When m is 1, platinum oxide is preferably used.

As the solvent, any solvent can be used as long as it does not inhibit the reaction, and examples include, for example, ethers such as tetrahydrofuran, 1,2-dimethoxyethane and 1,4-dioxane; alcohols such as methanol and ethanol; water; or a mixed solvent thereof.

<Second Step>

The final target compound (25) can be prepared by the hydrolysis of the 3-(5-arylphenyl)propanoic acid ester derivative (24) obtained in the first step. This reaction is carried out in a solvent, in the presence of a base, at a reaction temperature of from 0° C. to 180° C., preferably at a temperature of from 0° C. to the boiling point of the solvent.

As the base, examples include, for example, inorganic bases such as sodium hydroxide, potassium hydroxide, potassium carbonate and sodium carbonate.

As the solvent, any solvent can be used as long as it does not inhibit the reaction, and examples include, for example, ethers such as tetrahydrofuran, 1,2-dimethoxyethane and 1,4-dioxane; alcohols such as methanol and ethanol; water; or a mixed solvent thereof.

When the aftertreatment is carried out under acidic condition, the free form of the carboxylic acid can be obtained. When the aftertreatment is carried out under basic condition, the salt of the carboxylic acid can be obtained.

The compounds represented by the general formula (I), wherein X is —$CH_2CH_2$—, can be prepared, for example, by a method shown below.

<Scheme 6>

[Chemical formula 11]

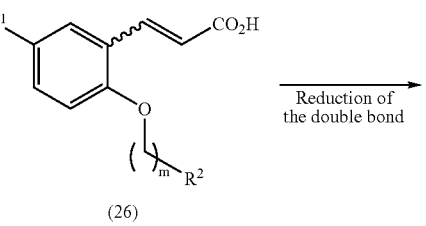

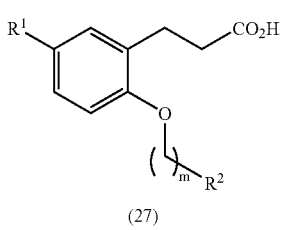

wherein each of $R^1$, $R^2$ and m has the same meanings as that described above.

The final target compound (27) can be prepared by the reduction of the double bond of the 3-(5-arylphenyl)propenoic acid derivative (26). This reaction is carried out in a solvent under hydrogen atmosphere, in the presence of a catalytic amount of a transition metal, at a reaction temperature of from 0° C. to 180° C., preferably at a temperature of from 0° C. to the boiling point of the solvent.

As the transition metal, examples include, for example, palladium-activated charcoal, platinum oxide and the like. When m is 1, platinum oxide is preferably used.

As the solvent, any solvent can be used as long as it does not inhibit the reaction, and examples include, for example, ethers such as tetrahydrofuran, 1,2-dimethoxyethane and 1,4-dioxane; alcohols such as methanol and ethanol; water; or a mixed solvent thereof.

As it is obvious from the present preparation method, the compounds represented by the general formula (I), wherein X is —CH=CH—, are useful as the synthetic intermediates for the compounds wherein X is —$CH_2CH_2$—.

The compounds represented by the general formula (I), wherein X is —$N(R^3)$—C(=O)—, m is 1, can be prepared, for example, by a method shown below.

<Scheme 7>

[Chemical formula 12]

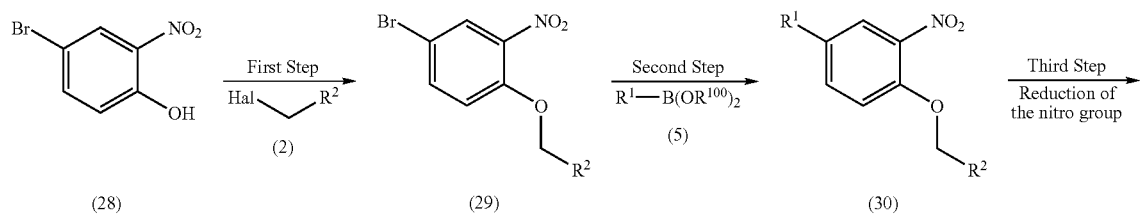

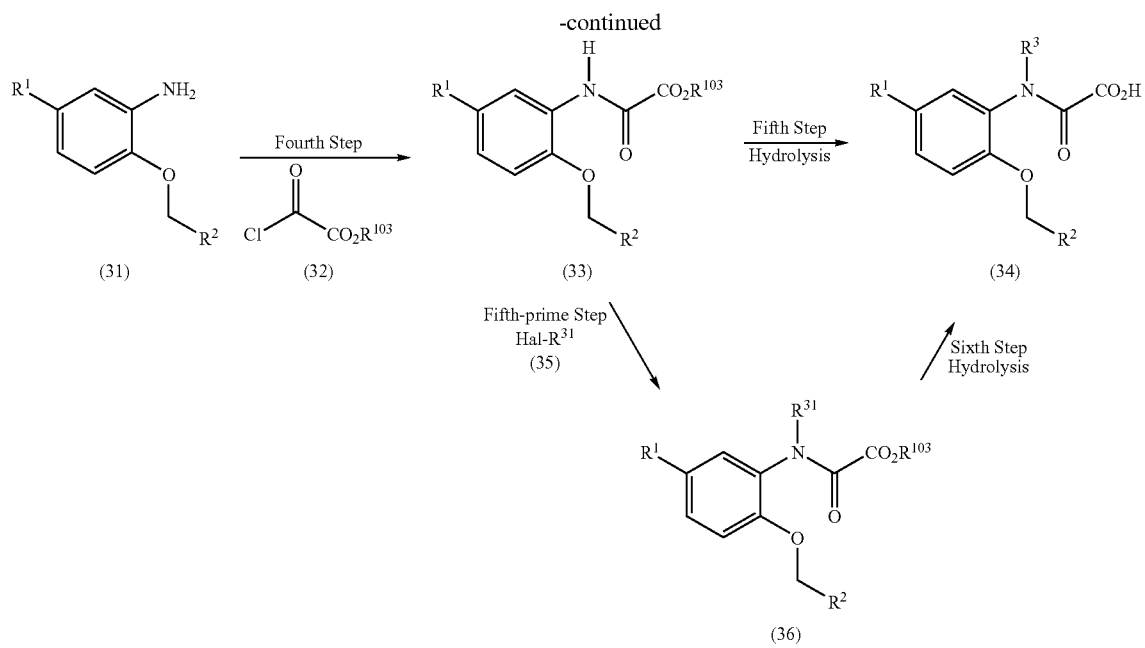

wherein Hal represents a halogen atom; $R^{100}$ represents hydrogen atom, a $C_{1-4}$ alkyl group or the like; $R^{103}$ represents a $C_{1-4}$ alkyl group or the like; $R^{31}$ represents a $C_{1-4}$ alkyl group; each of $R^1$, $R^2$ and $R^3$ has the same meanings as that described above.

<First Step>

The 1-aralkyloxy-4-bromo-2-nitrobenzene derivative (29) can be prepared by reacting the 4-bromo-2-nitrophenol (28) with the aralkyl halide derivative (2). This reaction is carried out in a solvent, in the presence of a base, at a reaction temperature of from 0° C. to 180° C., preferably at a temperature of from 0° C. to the boiling point of the solvent.

As the base, examples include inorganic bases such as sodium hydride, potassium hydride, potassium carbonate, sodium carbonate and sodium hydrogencarbonate; and organic bases such as triethylamine and diisopropylethylamine.

As the solvent, any solvent can be used as long as it does not inhibit the reaction, and examples include, for example, halogenated solvents such as dichloromethane, dichloroethane and chloroform; ethers such as tetrahydrofuran, 1,2-dimethoxyethane and 1,4-dioxane; amides such as dimethylformamide and N-methylpyrrolidone; aromatic solvents such as benzene and toluene; ketones such as acetone and 2-butanone; or a mixed solvent thereof.

<Second Step>

The 1-aralkyloxy-4-aryl-2-nitrobenzene derivative (30) can be prepared by reacting the 1-aralkyloxy-4-bromo-2-nitrobenzene derivative (29) obtained in the first step with the arylboronic acid derivative (5). This reaction is carried out in a solvent, in the presence of a catalytic amount of a transition metal complex, in the presence or absence of a base, at a reaction temperature of from 0° C. to 180° C., preferably at a temperature of from 0° C. to the boiling point of the solvent.

As the transition metal complex, examples include, for example, [1,1 bis(diphenylphosphino)ferrocene]dichloropalladium (II), tetrakis(triphenylphosphine)palladium and the like.

As the base, examples include inorganic bases such as potassium carbonate, sodium carbonate and sodium hydrogencarbonate; and organic bases such as triethylamine and diisopropylethylamine.

As the solvent, any solvent can be used as long as it does not inhibit the reaction, and examples include, for example, ethers such as tetrahydrofuran, 1,2-dimethoxyethane and 1,4-dioxane; amides such as dimethylformamide and N-methylpyrrolidone; aromatic solvents such as benzene and toluene; alcohols such as methanol and ethanol; water; or a mixed solvent thereof.

<Third Step>

The 2-amino-1-aralkyloxy-4-arylbenzene derivative (31) can be prepared by the reduction of the nitro group of the 1-aralkyloxy-4-aryl-2-nitrobenzene derivative (30) obtained in the second step. This reaction is carried out in a solvent under hydrogen atmosphere, in the presence of a catalytic amount of a transition metal, at a reaction temperature of from 0° C. to 180° C., preferably at a temperature of from 0° C. to the boiling point of the solvent.

As the transition metal, examples include, for example, palladium-activated charcoal, platinum oxide and the like. When m is 1, platinum oxide is preferably used.

As the solvent, any solvent can be used as long as it does not inhibit the reaction, and examples include, for example, ethers such as tetrahydrofuran, 1,2-dimethoxyethane and 1,4-dioxane; alcohols such as methanol and ethanol; water; or a mixed solvent thereof.

<Fourth Step>

The N-phenyloxamic acid ester derivative (33) can be prepared by reacting the 2-amino-1-aralkyloxy-4-arylbenzene derivative (31) obtained in the third step with the chloroglyoxylic acid ester (32). This reaction is carried out in a solvent, in the presence of a base, at a reaction temperature of from 0° C. to 180° C., preferably at a temperature of from 0° C. to the boiling point of the solvent.

As the base, examples include inorganic bases such as potassium carbonate, sodium carbonate and sodium hydrogencarbonate; and organic bases such as triethylamine and diisopropylethylamine.

As the solvent, any solvent can be used as long as it does not inhibit the reaction, and examples include, for example, halogenated solvents such as dichloromethane, dichloroethane and chloroform; ethers such as tetrahydrofuran, 1,2-dimethoxyethane and 1,4-dioxane; or a mixed solvent thereof.

<Fifth Step>

The final target compound (34) can be prepared by the hydrolysis of the N-phenyloxamic acid ester derivative (33) obtained in the fourth step. This reaction is carried out in a solvent, in the presence of a base, at a reaction temperature of from 0° C. to 180° C., preferably at a temperature of from 0° C. to the boiling point of the solvent.

As the base, examples include, for example, inorganic bases such as sodium hydroxide, potassium hydroxide, potassium carbonate and sodium carbonate.

As the solvent, any solvent can be used as long as it does not inhibit the reaction, and examples include, for example, ethers such as tetrahydrofuran, 1,2-dimethoxyethane and 1,4-dioxane; alcohols such as methanol and ethanol; water; or a mixed solvent thereof.

When the aftertreatment is carried out under acidic condition, the free form of the oxamic acid can be obtained. When the aftertreatment is carried out under basic condition, the salt of the oxamic acid can be obtained.

<Fifth-prime Step>

The N-methyl-N-phenyloxamic acid ester derivative (36) can be prepared by reacting the N-phenyloxamic acid ester derivative (33) obtained in the fourth step with the alkyl halide (35). This reaction is carried out in a solvent, in the presence of a base, at a reaction temperature of from 0° C. to 180° C., preferably at a temperature of from 0° C. to the boiling point of the solvent.

As the base, examples include inorganic bases such as sodium hydride, potassium hydride, potassium carbonate, sodium carbonate and sodium hydrogencarbonate; and organic bases such as triethylamine and diisopropylethylamine.

As the solvent, any solvent can be used as long as it does not inhibit the reaction, and examples include, for example, halogenated solvents such as dichloromethane, dichloroethane and chloroform; ethers such as tetrahydrofuran, 1,2-dimethoxyethane and 1,4-dioxane; or a mixed solvent thereof.

<Sixth Step>

The final target compound (34) can be prepared by the hydrolysis of the N-methyl-N-phenyloxamic acid ester derivative (36) obtained in the fifth-prime step. This reaction is carried out in a solvent, in the presence of a base, at a reaction temperature of from 0° C. to 180° C., preferably at a temperature of from 0° C. to the boiling point of the solvent.

As the base, examples include, for example, inorganic bases such as sodium hydroxide, potassium hydroxide, potassium carbonate and sodium carbonate.

As the solvent, any solvent can be used as long as it does not inhibit the reaction, and examples include, for example, ethers such as tetrahydrofuran, 1,2-dimethoxyethane and 1,4-dioxane; alcohols such as methanol and ethanol; water; or a mixed solvent thereof.

When the aftertreatment is carried out under acidic condition, the free form of the oxamic acid can be obtained. When the aftertreatment is carried out under basic condition, the salt of the oxamic acid can be obtained.

In the compounds represented by the general formula (I), the compounds wherein X is —N($R^3$)—C(=O)— and m is 0 can be prepared, for example, by using the aryl halide derivative (Hal-$R^2$) instead of the aralkyl halide derivative (2) in scheme 7.

In the examples of the specification, preparation methods of typical compounds included in the general formula (I) are explained in details. Therefore, those skilled in the art can prepare any compound included in the general formula (I) by referring to the explanations of the aforementioned general preparation methods and of specific preparation methods of the examples, selecting appropriate reaction raw materials, reaction reagents, and reaction conditions, and by adding appropriate modification and alteration of these methods, if necessary.

The medicament of the present invention can be used for prophylactic and/or therapeutic treatment of diseases caused by an expression of PAI-1 or an enhancement of PAI-1 activity. The term "therapeutic treatment" used in the present specification includes prevention of progression of diseases and the term "prophylactic treatment" includes the prevention of reoccurrence. The medicament of the present invention can be used, for example, for prophylactic and/or therapeutic treatment of diseases caused by thrombogenesis, fibrogenesis, accumulation of visceral fat, angiogenesis, deposition and remodeling of extracellular matrix, proliferation, movement, infiltration, and migration of cell (for example, tumor cell and vascular endothelial cell), and tissue remodeling (for example, cardiac remodeling and vascular remodeling).

More specifically, the medicament of the present invention can be used for prophylactic and/or therapeutic treatment of one or more diseases selected from ischemic cerebrovascular diseases such as cerebral thrombosis, cerebral embolism, cerebral infarction, transient ischemic attack, cerebral stroke and vascular dementia; ischemic heart diseases such as angina, myocardial infarction, intraatrial thrombosis caused by atrial fibrillation, and heart failure; thrombotic pulmonary diseases such as pulmonary thrombosis and pulmonary embolism; venous occlusive diseases such as deep vein thrombosis (DVT) and thrombophlebitis; peripheral arterial occlusive diseases such as acute arterial occlusion and chronic arterial occlusion; thrombus after bypass vascular transplantation; disseminated intravascular coagulation (DIC); acute coronary occlusion and restenosis after percutaneous transluminal coronary angioplasty (PTCA); angiopathy and thromboses caused by immune disorder such as antiphospholipid syndrome; angiopathy and thromboses caused by congenital thrombotic tendency such as genetic abnormality; thrombotic renal diseases such as renal thrombosis and renal embolism; nephropathy caused by metabolic diseases; arteriosclerosis; thrombotic diseases, thrombosis, fibrotic diseases, blood coagulation, ischemic diseases, heart attack, deep-seated thrombosis, pulmonary thromboembolism, venous thromboembolism, nephrosclerosis, metabolic syndrome, aldosterone tissue disorder, organ failure, economy-class syndrome, endotoxic shock, allergic diseases, vascular events such as cerebrovascular event and cardiovascular event, angiitis, nonbacterial thrombotic endocarditis; severe infectious diseases such as sepsis; fibrin-dependent pain in arthritis; diabetic complications such as retinopathy, nephropathy, neurosis, peripheral circulatory disturbance; hypertension; diabetes; hyperinsulinemia; hypercholesteremia; insulin resistant disorder; hyperlipidemia; obesity; tumors including solid cancers such as lung cancer, pancreatic cancer, colon cancer, gastric cancer, prostate cancer, breast cancer, cervical cancer and ovarian cancer; tumor invasion; tumor metastasis; asthma; tissue fibrosis such as hepatic cirrhosis, pulmonary fibrosis, renal fibrosis and interstitial cystitis; acute rejections and arterial lesions after organ transplantation such as cardiac transplantation and renal transplantation. Moreover, the medicament of the present invention is effective in healing of wounds and bedsores because the medicament of the present invention can prevent and improve thrombus formation.

As the active ingredient of the medicament on the present invention, 1 or more kinds of substances selected from the group consisting of the compound represented by the general formula (I) and a pharmacologically acceptable salt thereof, and a hydrate thereof and a solvate thereof may be used. The aforementioned substance, per se, may be administered as the medicament of the present invention, however, preferably, the medicament of the present invention is provided in the form of a pharmaceutical composition comprising the aforementioned substance which is an active ingredient together with one or more pharmacologically acceptable pharmaceutical additives. In the aforementioned pharmaceutical compositions, a ratio of the active ingredient to the pharmaceutical additives is 1 weight % to 90 weight %.

The pharmaceutical compositions of the present invention may be administered as pharmaceutical compositions for oral administration, for example, granules, subtilized granules, powders, hard capsules, soft capsules, syrup, emulsion, suspension, or solution, or may be administered as pharmaceutical compositions for parenteral administration, for example, injections for intravenous administration, intramuscular administration, or subcutaneous administration, drops, suppositories, percutaneous absorbent, transmucosal absorption preparations, nasal drops, ear drops, instillation, and inhalants. Preparations made as pharmaceutical compositions in a form of powder may be dissolved when necessary and used as injections or drip infusions.

For preparation of pharmaceutical compositions, solid or liquid pharmaceutical additives may be used. Pharmaceutical additives may either be organic or inorganic. When an oral solid preparation is prepared, an excipient is added to the active ingredient, and further binders, disintegrator, lubricant, colorant, corrigent are added, if necessary, preparations in the forms of tablets, coating tablets, granules, powders, capsules and the like may be manufactured by common procedures. Examples of the excipient include lactose, sucrose, saccharose, glucose, corn starch, starch, talc, sorbit, crystal cellulose, dextrin, kaolin, calcium carbonate, and silicon dioxide. Examples of the binder include, for example, polyvinyl alcohol, polyvinyl ether, ethyl cellulose, methyl cellulose, gum Arabic, tragacanth, gelatine, shellac, hydroxypropyl cellulose, hydroxypropyl methyl cellulose, calcium citrate, dextrin, and pectin. Examples of the lubricant include, for example, magnesium stearate, talc, polyethylene glycol, silica, and hydrogenated vegetable oil. As the coloring agent, any material can be used which are approved to be added to ordinary pharmaceuticals. As the corrigent, cocoa powder, menthol, aromatic acid, peppermint oil, d-borneol, cinnamon powder and the like can be used. These tables and granules may be applied with sugarcoating, gelatine coating, or an appropriate coating, if necessary. Preservatives, antioxidant and the like may be added, if required.

For liquid preparations for oral administration such as emulsions, syrups, suspensions, and solutions, ordinary used inactive diluents, for example, water or vegetable oil may be used. For these preparations, besides inactive diluents, adjuvants such as wetting agents, suspending aids, sweating agents, flavoring agents, coloring agents or preservatives may be blended. After a liquid preparation is manufactured, the preparation may be filled in capsules made of a absorbable substance such as gelatin. Examples of solvents or suspending agents used for the preparations of parenteral administration such as injections or suppositories include, for example, water, propylene glycol, polyethylene glycol, benzyl alcohol, ethyl oleate, and lecithin. Examples of base materials used for preparation of suppositories include, for example, cacao butter, emulsified cacao butter, lauric fat, and witepsol. Methods for preparation of the aforementioned preparations are not limited, and any method ordinarily used in the art may be used.

When the composition are prepared in the form of injections, carriers such as, for example, diluents including water, ethanol, macrogol, propyleneglycol, citric acid, acetic acid, phosphoric acid, lactic acid, sodium lactate, sulfuric acid and sodium hydroxide, pH modifiers and buffer solutions including sodium citrate, sodium acetate and sodium phosphate, stabilizers such as sodium pyrosulfite, ethylenediaminetetraacetic acid, thioglycolic acid and thiolactate may be used. For the preparation, a sufficient amount of a salt, glucose, mannitol or glycerin may be blended in the preparation to manufacture an isotonic solution, and an ordinary solubilizer, a soothing agent, or a topical anesthetic may be used.

When the preparation in the form of an ointment such as a paste, a cream, and a gel is manufactured, an ordinarily used base material, a stabilizer, a wetting agent, and a preservative may be blended, if necessary, and may be prepared by mixing the components by a common method. As the base material, for example, white petrolatum, polyethylene, paraffin, glycerin, cellulose derivatives, polyethylene glycol, silicon, and bentonite may be used. As the preservative, paraoxy methyl benzoate, paraoxy ethyl benzoate, paraoxy propyl benzoate and the like may be used. When the preparation in the form of a patch is manufactured, the aforementioned ointment, cream gel, or paste and the like may be applied by a common method to an ordinary support. As the support, fabric made of cotton, span rayon, and synthetic fibersor or nonwoven fabric, and a film or a foam sheet such as made of soft vinyl chloride, polyethylene, and polyurethane and the like may be preferably used.

A dose of the medicament of the present invention is not particularly limited. For oral administration, a dose may generally be 0.01 to 5,000 mg per day for an adult as the weight of the compound of the present invention. It is preferred to increase or decrease the above dose appropriately depending on the age, pathological conditions, and symptoms of a patient. The above dose may be administered once a day or 2 to 3 times a day as divided portions with proper intervals, or intermittent administration for every several days may be acceptable. When the medicament is used as an injection, the dose may be 0.001 to 100 mg per day for an adult as the weight of the compound of the present invention.

Oral or parenteral administration of the medicament of the present invention may be carried out preoperatively, when the medicament of the present invention is used for prophylactic and/or therapeutic treatment of intravascular lesions after vascular transplantation or organ transplantation, or after blood circulation restoration, whose examples include, for example, thrombus after bypass vascular transplantation, acute coronary occlusion and restenosis after PTCA, arterial lesions after organ transplantation such as cardiac transplantation and renal transplantation and the like. Furthermore, oral or parenteral administration of the medicament of the present invention may be carried out intraoperatively and/or postoperatively in addition to the aforementioned preoperative administration, if necessary.

EXAMPLES

The present invention will be explained more specifically with reference to the following examples. However the scope of the present invention is not limited to the following examples. In the present examples, when a carboxy group is selected as the Y of the compound represented by the general formula (I), compounds wherein the groups and numeric values shown on Table 1 are selected as $R^1$, $R^2$ and m are prepared. Furthermore, when the groups shown on Table 2 are selected as —X—Y of the compound represented by the general formula (I), compounds wherein the groups and numeric values shown on Table 2 are selected as $R^1$, $R^2$ and m are prepared.

In the following, the structure of the intermediate prepared in each example is shown, respectively.

TABLE 3

| Example | Structure |
| --- | --- |
| 1 (1) | 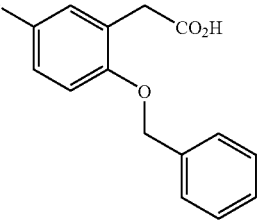 |
| 2 (1) | 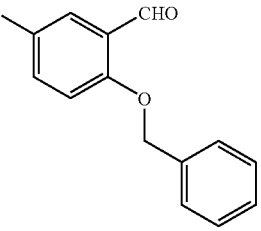 |
| 2 (2) | 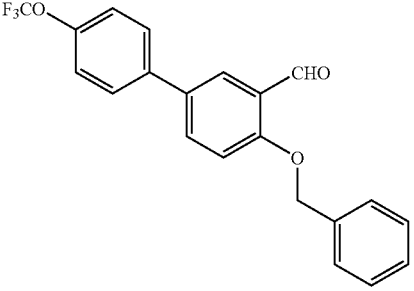 |
| 4 (1) | 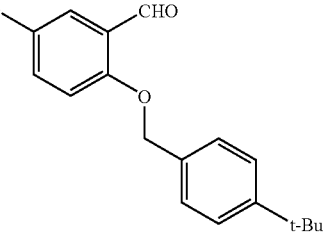 |
| 4 (2) | 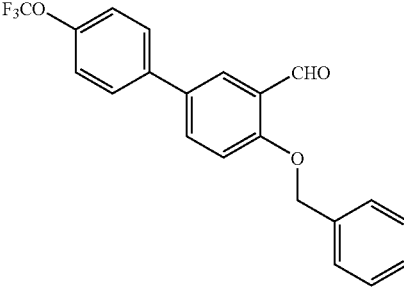 |

TABLE 3-continued
| Example | Structure |
|---|---|
| 6 (1) | 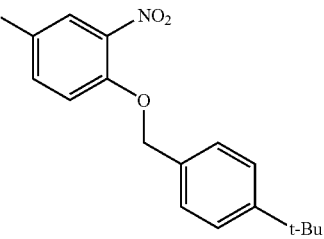 |
| 6 (2) | 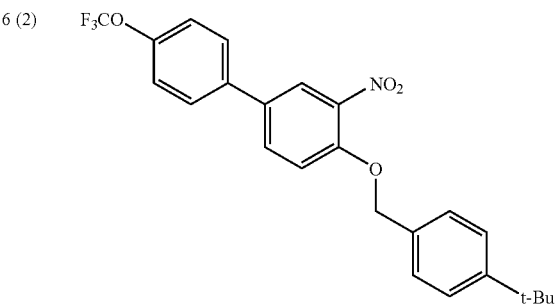 |
| 6 (3) | 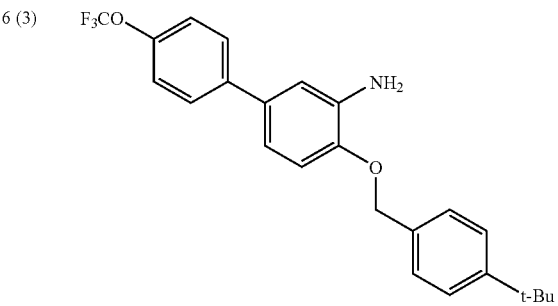 |
| 6 (4) | 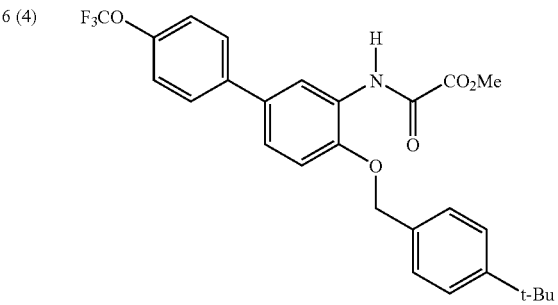 |
| 7 (1) | 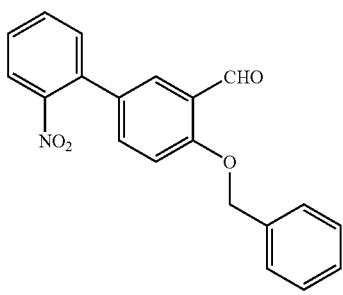 |

TABLE 3-continued
| Example | Structure |
|---|---|
| 9 (1) | 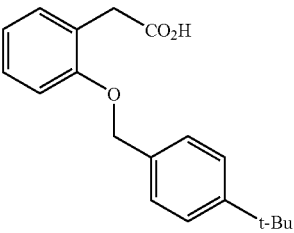 |
| 9 (2) | 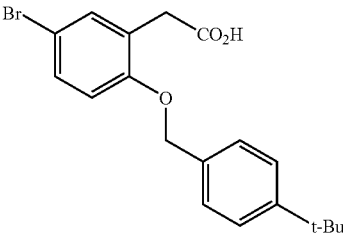 |
| 11 (1) | 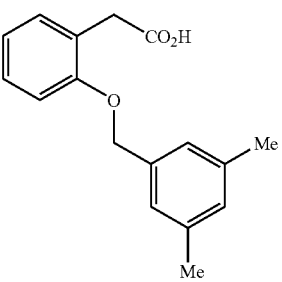 |
| 11 (2) | 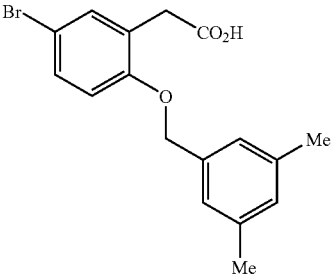 |
| 12 (1) | 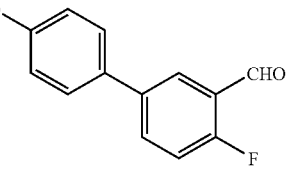 |
| 12 (2) | 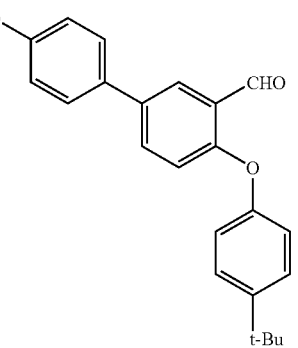 |

TABLE 3-continued
| Example | Structure |
|---|---|
| 12 (3) | 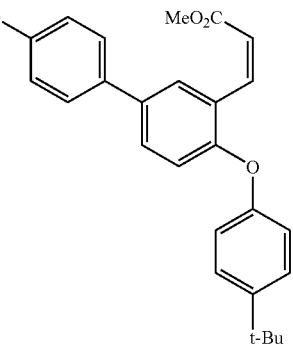 |
| 14 (1) | 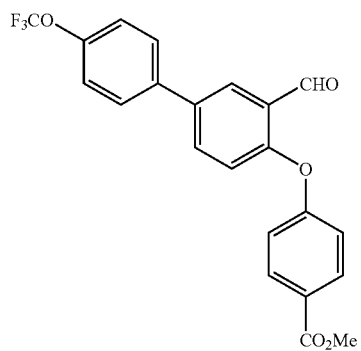 |
| 14 (2) | 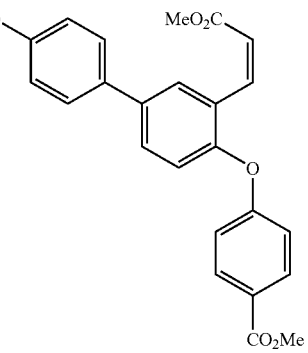 |
| 16 (1) | 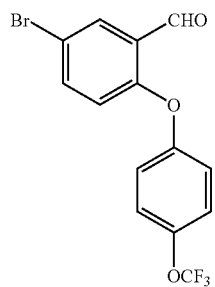 |

TABLE 3-continued

| Example | Structure |
| --- | --- |
| 16 (2) | 4'-(trifluoromethoxy)-4-(4-(trifluoromethoxy)phenoxy)-[1,1'-biphenyl]-3-carbaldehyde |
| 18 (1) | methyl 2-(4-((4-(tert-butyl)benzyl)oxy)-4'-(trifluoromethoxy)-[1,1'-biphenyl]-3-yl)(methyl)amino)-2-oxoacetate |
| 19 (1) | 4-hydroxy-4'-(trifluoromethoxy)-[1,1'-biphenyl]-3-carbaldehyde |
| 19 (2) | 4-((4-chlorobenzyl)oxy)-4'-(trifluoromethoxy)-[1,1'-biphenyl]-3-carbaldehyde |
| 21 (1) | 4-((4-fluorobenzyl)oxy)-4'-(trifluoromethoxy)-[1,1'-biphenyl]-3-carbaldehyde |

TABLE 3-continued
| Example | Structure |
|---|---|
| 23 (1) | 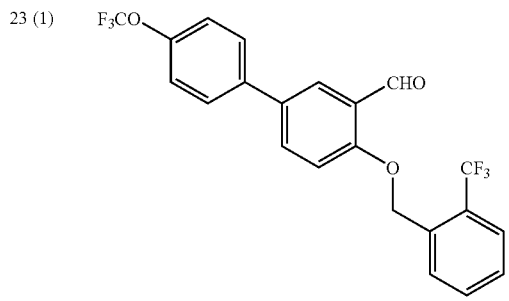 |
| 25 (1) | 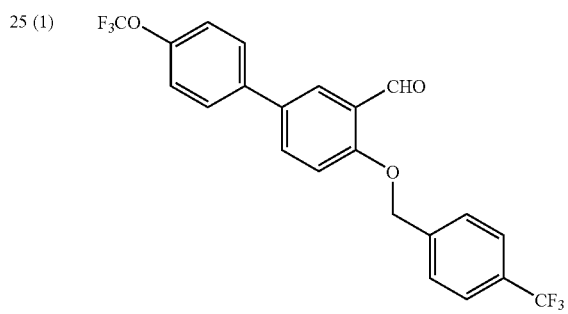 |
| 27 (1) | 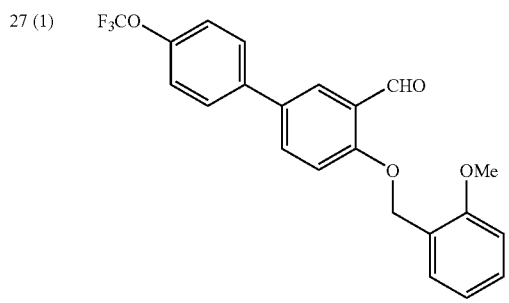 |
| 29 (1) | 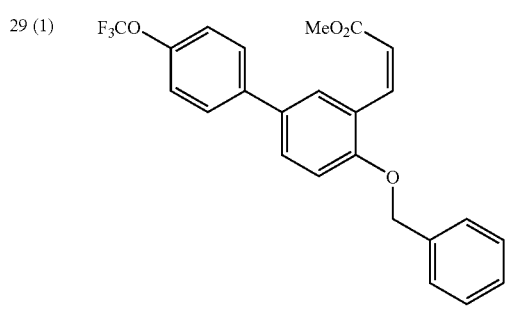 |
| 30 (1) | 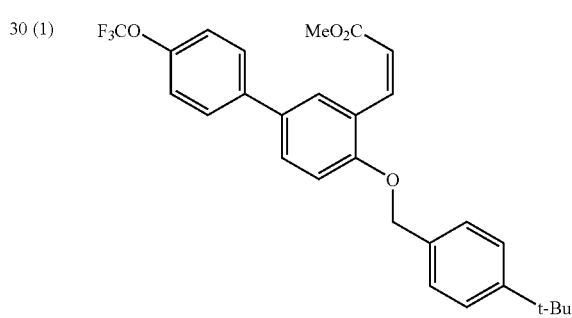 |

TABLE 3-continued
| Example | Structure |
|---|---|
| 31 (1) | 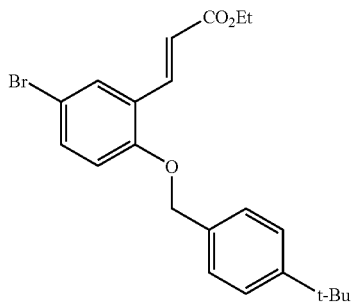 |
| 31 (2) | 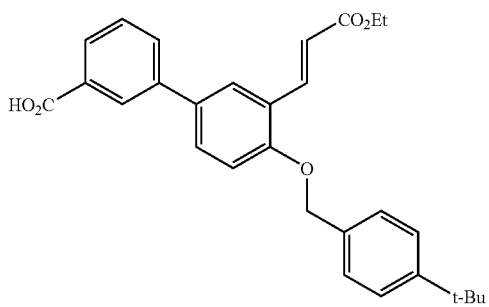 |
| 31 (3) | 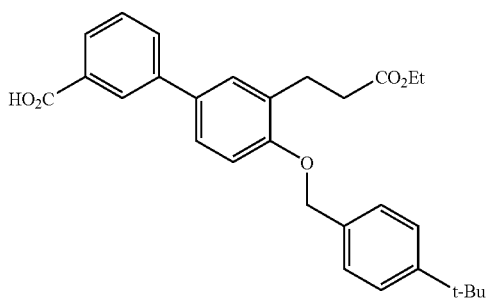 |
| 32 (1) | 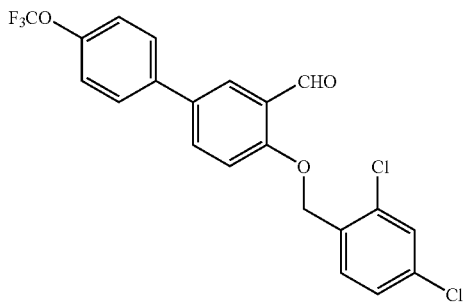 |
| 32 (2) | 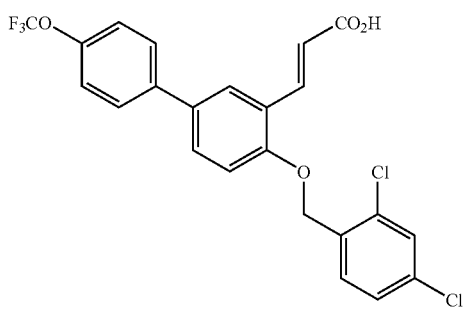 |

TABLE 3-continued

| Example | Structure |
| --- | --- |
| 33 (1) | 4'-(trifluoromethoxy)-4-[(3-methylbenzyl)oxy]biphenyl-3-carbaldehyde |
| 33 (2) | (2E)-3-{4'-(trifluoromethoxy)-4-[(3-methylbenzyl)oxy]biphenyl-3-yl}acrylic acid |
| 34 (1) | 4'-(trifluoromethoxy)-4-(biphenyl-4-ylmethoxy)biphenyl-3-carbaldehyde |
| 34 (2) | (2E)-3-{4'-(trifluoromethoxy)-4-(biphenyl-4-ylmethoxy)biphenyl-3-yl}acrylic acid |
| 35 (1) | 1-(chloromethyl)-4-n-butylbenzene |

TABLE 3-continued
| Example | Structure |
|---|---|
| 35 (2) | 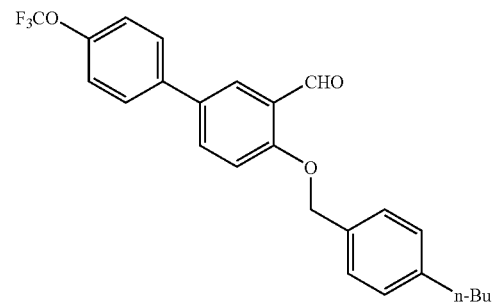 |
| 35 (3) | 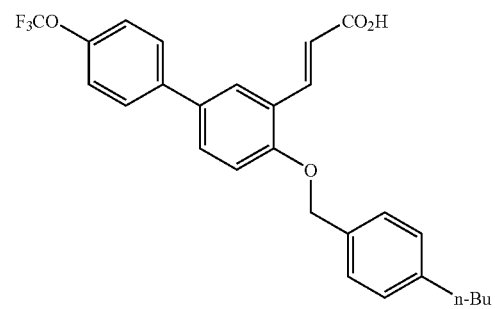 |
| 36 (1) | 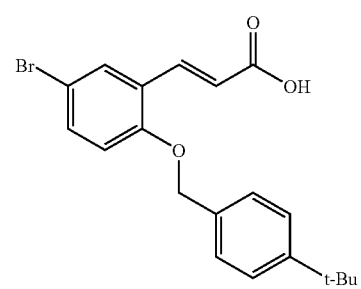 |
| 48 (1) | 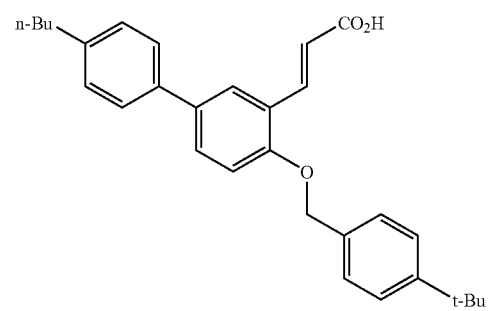 |
| 50 (1) | 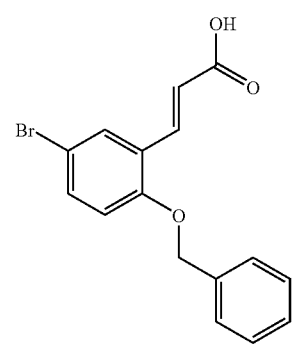 |

TABLE 3-continued
| Example | Structure |
|---|---|
| 51 (1) | 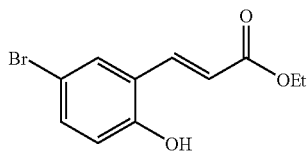 |
| 51 (2) | 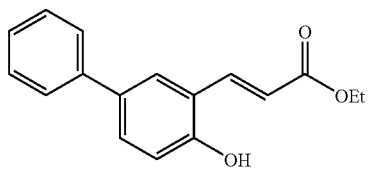 |
| 51 (3) | 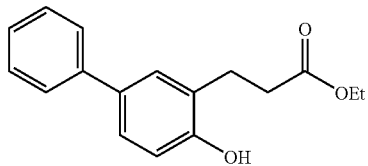 |
| 51 (4) | 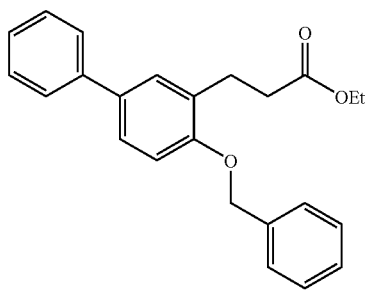 |
| 56 (1) | 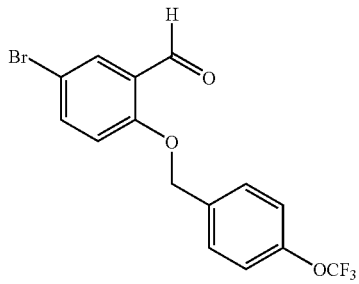 |
| 56 (2) | 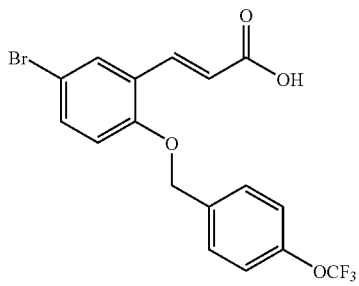 |

TABLE 3-continued
| Example | Structure |
| --- | --- |
| 58 (1) | 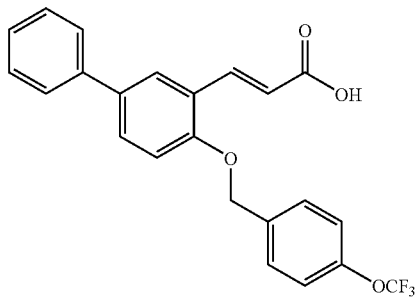 |
| 59 (1) | 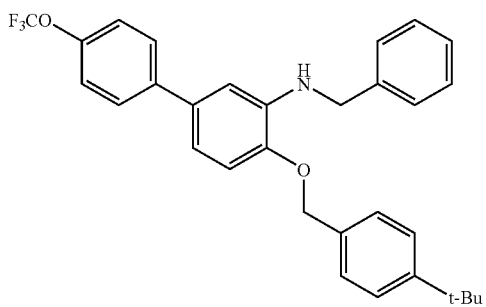 |
| 59 (2) | 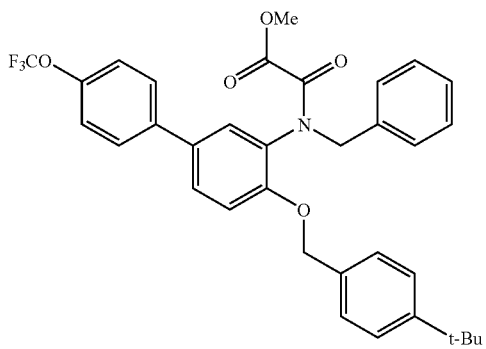 |
| 60 (1) | 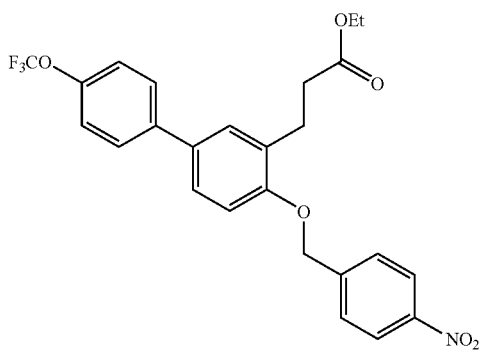 |

TABLE 3-continued

| Example | Structure |
|---|---|
| 63 (1) | 4'-(trifluoromethoxy)-4-((3-(trifluoromethyl)benzyl)oxy)-[1,1'-biphenyl]-3-carbaldehyde |
| 65 (1) | 4-((3,5-dimethylbenzyl)oxy)-4'-(trifluoromethoxy)-[1,1'-biphenyl]-3-carbaldehyde |
| 65 (2) | (E)-3-(4-((3,5-dimethylbenzyl)oxy)-4'-(trifluoromethoxy)-[1,1'-biphenyl]-3-yl)acrylic acid |
| 66 (1) | 4-((4-methoxybenzyl)oxy)-4'-(trifluoromethoxy)-[1,1'-biphenyl]-3-carbaldehyde |

TABLE 3-continued

| Example | Structure |
|---|---|
| 66 (2) | 4'-(trifluoromethoxy)-4-((4-methoxybenzyl)oxy)-[1,1'-biphenyl]-3-yl acrylic acid |
| 67 (1) | 4'-(trifluoromethoxy)-4-((4-methylbenzyl)oxy)-[1,1'-biphenyl]-3-carbaldehyde |
| 67 (2) | 4'-(trifluoromethoxy)-4-((4-methylbenzyl)oxy)-[1,1'-biphenyl]-3-yl acrylic acid |
| 68 (1) | 4'-(trifluoromethoxy)-4-((4-(trifluoromethoxy)benzyl)oxy)-[1,1'-biphenyl]-3-carbaldehyde |
| 68 (2) | 4'-(trifluoromethoxy)-4-((4-(trifluoromethoxy)benzyl)oxy)-[1,1'-biphenyl]-3-yl acrylic acid |

TABLE 3-continued
| Example | Structure |
|---|---|
| 69 (1) | 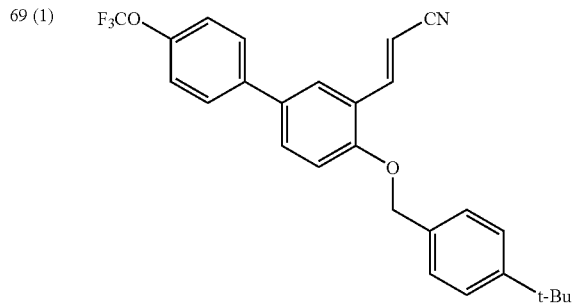 |
| 69 (2) | 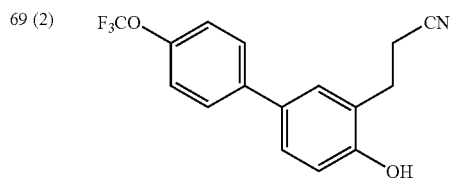 |
| 69 (3) | 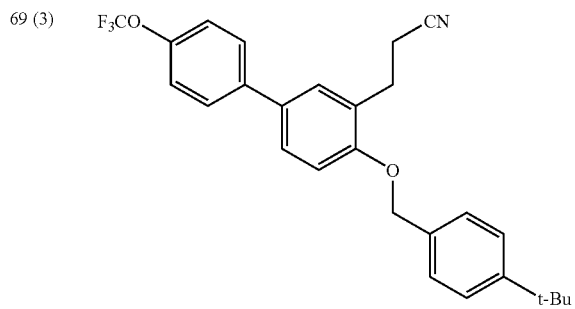 |
| 74 (1) | 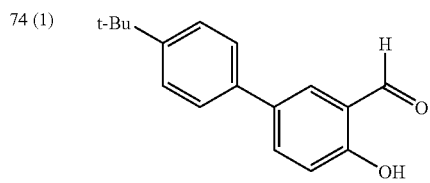 |
| 74 (2) | 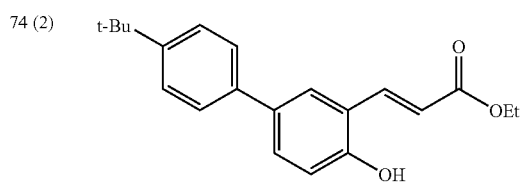 |
| 74 (3) | 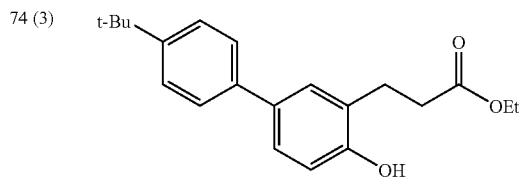 |

TABLE 3-continued
| Example | Structure |
|---|---|
| 74 (4) | 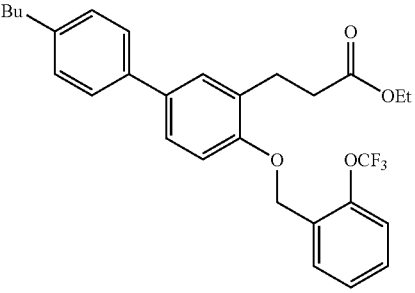 |
| 75 (1) | 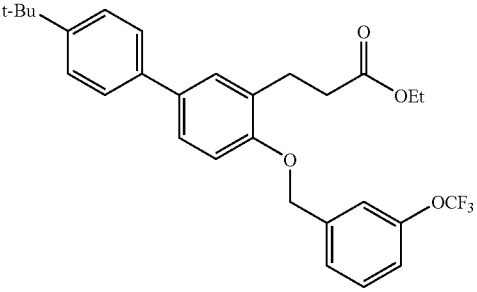 |
| 76 (1) | 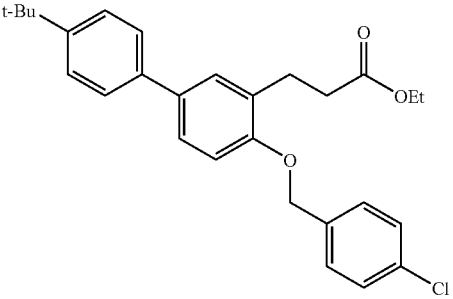 |
| 77 (1) | 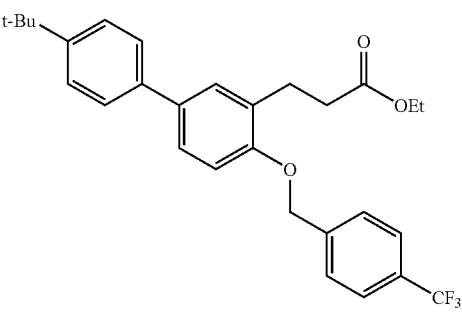 |
| 78 (1) | 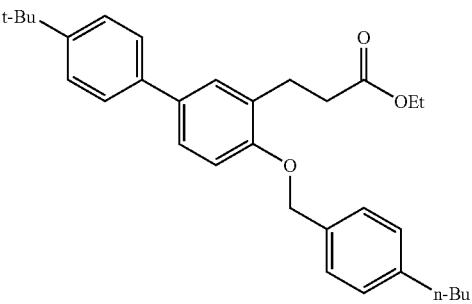 |

Example 1

Preparation of [4-benzyloxy-4'-(trifluoromethoxy)biphenyl 3-yl]acetic acid (compound No. 1)

(1) Preparation of 2-benzyloxy-5-bromophenylacetic acid

A mixture of 2-benzyloxyphenylacetic acid (242 mg, 11.0 mmol), N-bromosuccinimide (178 mg, 1.9 mmol) and dichloromethane (4 ml) was stirred overnight at room temperature under argon atmosphere. The reaction mixture was diluted with ethyl acetate, washed with saturated brine, and dried over anhydrous sodium sulfate. The solvent was evaporated to give the title compound (280 mg, 87.2%) as a white solid.
$^1$H-NMR (CDCl$_3$) δ: 3.67 (2H, s), 5.04 (2H, s), 6.78 (1H, d, J=9.6 Hz), 7.25-7.37 (7H, m).

(2) Preparation of [4-benzyloxy-4'-(trifluoromethoxy)biphenyl-3-yl]acetic acid (compound No. 1)

A mixture of 2-benzyloxy-5-bromophenylacetic acid (261 mg, 0.813 mmol), 4-(trifluoromethoxy)phenyl boronic acid (218 mg, 1.056 mmol), [1,1'-bis(diphenylphosphino)ferrocene]dichloropalladium(II) (43 mg, 0.057 mmol), potassium carbonate (169 mg, 1.22 mmol), dioxane (4 ml) and water (0.5 ml) was stirred at 80° C. for 2 hours. The reaction mixture was cooled to room temperature, and the solvent was evaporated under reduced pressure. Ethyl acetate was added to the residue, and the solution was filtered through celite. The residue obtained by concentration of the filtrate under reduced pressure was purified by column chromatography on silica gel (n-hexane:ethyl acetate=3:2) to give the title compound (160 mg, 48.9%) as a white solid.
$^1$H-NMR (CDCl$_3$) δ: 3.78 (2H, s), 5.11 (2H, s), 6.99 (1H, d, J=8.1 Hz), 7.23-7.45 (9H, m), 7.53 (2H, d, J=9.0 Hz).

Example 2

Preparation of (E)-3-[4-benzyloxy-4'-(trifluoromethoxy)biphenyl-3-yl]propenoic acid (compound No 2)

(1) Preparation of 2-benzyloxy-5-bromobenzaldehyde

A mixture of benzyl bromide (2.04 g, 11.926 mmol), 5-bromosalicylaldehyde (1.844 g, 9.174 mmol), potassium carbonate (5.07 g, 36.696 mmol) and dimethylformamide (15 ml) was stirred at 50° C. for 2 hours under argon atmosphere. The reaction mixture was cooled to room temperature, diluted with water, and extracted with ethyl acetate. The organic layer was washed with water and saturated brine, and dried over anhydrous sodium sulfate. The residue obtained by evaporation of the solvent under reduced pressure was washed with methanol to give the title compound (1.2 g, 44.9%) as a white solid.
$^1$H-NMR (CDCl$_3$) δ: 5.10 (2H, s), 6.80 (1H, d, J=9.0 Hz), 7.28-7.44 (6H, m), 7.69 (1H, d, J=2.4 Hz), 10.46 (1H, s).

(2) Preparation of 4-benzyloxy-4'-(trifluoromethoxy)biphenyl-3-carbaldehyde The title compound was obtained in the same manner as the Example 1 (2) using the following raw materials.
Raw materials: 2-benzyloxy-5-bromobenzaldehyde and 4 (trifluoromethoxy)phenylboronic acid.
Yield: 63.0% (pale yellow solid).
$^1$H-NMR (DMSO-d$_6$) δ: 5.37 (2H, s), 7.32-7.57 (8H, m), 7.75-7.85 (2H, m), 7.96-8.03 (2H, m), 10.47 (1H, s).

(3) Preparation of (E)-3-[4-benzyloxy-4'-(trifluoromethoxy)biphenyl-3-yl]propenoic acid (compound No. 2).

A mixture of 4-benzyloxy-4'-(trifluoromethoxy)biphenyl-3-carbaldehyde (4.0 g, 9.336 mmol), malonic acid (2.137 g, 20.539 mmol), pyridine (4.3 ml) and piperidine (184 µl, 1.867 mmol) was refluxed for 1 hour under argon atmosphere. The reaction mixture was cooled to room temperature, adjusted to pH 1 by addition of 2N hydrochloric acid, and extracted with ethyl acetate. The organic layer was washed with saturated brine, and dried over anhydrous sodium sulfate. The residue obtained by evaporation of the solvent under reduced pressure was purified by column chromatography on silica gel (n-hexane:ethyl acetate=1:1) to give the title compound (4.26 g, 97.0%) as a white solid.
$^1$H-NMR (DMSO-d$_6$) δ: 5.24 (2H, s), 6.63 (1H, d, J=16.2 Hz), 7.04 (1H, d, J=8.7 Hz), 7.23-7.58 (10H, m), 7.73 (1H, d, J=6.9 Hz), 8.20 (1H, d, J=16.2 Hz).

Example 3

Preparation of 3-[4-benzyloxy-4'-(trifluoromethoxy) biphenyl-3-yl]propanoic acid (compound No. 3)

A mixture of (E)-3-[4-benzyloxy-4'-(trifluoromethoxy)biphenyl-3-yl]propenoic acid (compound No. 2; 100 mg, 0.241 mmol), platinum oxide (5 mg) and ethanol (10 ml) was stirred for 1 hour under hydrogen atmosphere. The reaction mixture was filtered through celite. The residue obtained by concentration of the filtrate under reduced pressure was washed with methanol under suspension to give the title compound (78 mg, 78.0%) as a white solid.
$^1$H-NMR (CDCl$_3$) δ: 2.74 (2H, t, J=7.5 Hz), 3.06 (2H, t, J=7.8 Hz), 5.14 (2H, s), 6.96 (2H, d, J=8.4 Hz), 7.22-7.54 (11H, m).

Example 4

Preparation of (E)-3-{4-[4-(tert-butyl)benzyloxy]-4'-(trifluoromethoxy)biphenyl-3-yl}propenoic acid (compound No. 4).

(1) Preparation of 5-bromo-2-[4-(tert-butyl)benzyloxy]benzaldehyde

The title compound was obtained in the same manner as the Example 2 (1) using the following raw materials.
Raw materials: 4-(tert-butyl)benzyl bromide and 5-bromosalicylaldehyde.
Yield: 42.3% (pale yellow oil).
$^1$H-NMR (CDCl$_3$) δ: 1.36 (9H, s), 5.14 (2H, s), 6.97 (1H, d, J=8.7 Hz), 7.35 (2H, d, J=8.7 Hz), 7.43 (2H, d, J=8.7 Hz), 7.60 (1H, dd, J=2.7, 8.7 Hz), 7.94 (1H, d, J=2.7 Hz), 10.45 (1H, s).

(2) Preparation of 4-[4-(tert-butyl)benzyloxy]-4'-(trifluoromethoxy)biphenyl-3-carbaldehyde The title compound was obtained in the same manner as the Example 1 (2) using the following raw materials.

Raw materials: 5-bromo-2-[4-(tert-butyl)benzyloxy]benzaldehyde and 4-(trifluoromethoxy)phenylboronic acid.

Yield: 47.2% (pale yellow solid).

$^1$H-NMR (CDCl$_3$) δ: 1.34 (9H, s), 5.21 (2H, s), 7.16 (1H, d, J=9.0 Hz), 7.24-7.29 (2H, m), 7.37-7.47 (4H, m), 7.56-7.60 (2H, m), 7.73 (1H, dd, J=2.4, 9.0 Hz), 8.06 (1H, d, J=2.4 Hz), 10.59 (1H, s).

(3) Preparation of (E)-3-{4-[4-(tert-butyl)benzyloxy]-4'-(trifluoromethoxy)biphenyl-3-yl}propenoic acid (compound No. 4)

The title compound was obtained in the same manner as the Example 2 (3) using the following raw materials.

Raw materials: 4-[4-(tert-butyl)benzyloxy]-4'-(trifluoromethoxy)biphenyl-3-carbaldehyde and malonic acid.

Yield: 49.1% (white solid).

$^1$H-NMR (CDCl$_3$) δ: 1.35 (9H, s), 5.20 (2H, s), 6.63 (1H, d, J=16.2 Hz), 7.07 (1H, d, J=8.4 Hz), 7.23-7.57 (10H, m), 7.74 (1H, d, J=2.1 Hz), 8.20 (1H, d, J=16.2 Hz).

Example 5

Preparation of 3-{4-[4-(tert-butyl)benzyloxy]-4'-(trifluoromethoxy)biphenyl-3-yl}propanoic acid (compound No. 5)

The title compound was obtained in the same manner as the Example 3 using the following raw material.

Raw material: 3 {4-[4-(tert-butyl)benzyloxy]-4'-(trifluoromethoxy)biphenyl-3-yl}propenoic acid (compound No. 4).

Yield: 54.8% (white solid).

$^1$H-NMR (CDCl$_3$) δ: 1.34 (9H, s), 2.74 (2H, t, J=7.5 Hz), 3.06 (2H, t, J=7.5 Hz), 5.11 (2H, s), 6.97 (1H, d, J=8.1 Hz), 7.22-7.25 (2H, m), 7.35-7.44 (5H, m), 7.53 (2H, d, J=8.7 Hz).

Example 6

Preparation of N-{4-[4-(tert-butyl)benzyloxy]-4'-(trifluoromethoxy)biphenyl-3-yl}oxamic acid sodium salt (compound No. 6)

(1) 4-bromo-1-[4-(tert-butyl)benzyloxy]-2-nitrobenzene

The title compound was obtained in the same manner as the Example 2 (1) using the following raw materials.

Raw materials: 4-(tert-butyl)benzyl bromide and 4-bromo-2-nitrophenol.

Yield: 77.1% (white solid).

$^1$H-NMR (CDCl$_3$) δ: 1.32 (9H, s), 5.19 (2H, s), 7.02 (1H, d, J=8.7 Hz), 7.34-7.43 (4H, m), 7.58 (1H, dd, J=2.7, 8.7 Hz), 7.97 (1H, d, J=2.7 Hz).

(2) Preparation of 4-[4-(tert-butyl)benzyloxy]-3-nitro-4'-(trifluoromethoxy)biphenyl The title compound was obtained in the same manner as the Example 1 (2) using the following raw materials.

Raw materials: 4-bromo-1-[4 (tert-butyl)benzyloxy]-2-nitrobenzene and 4-(trifluoromethoxy)phenylboronic acid.

Yield: 74.6% (pale yellow solid).

$^1$H-NMR (CDCl$_3$) δ: 1.33 (9H, s), 5.26 (2H, s), 7.22 (1H, d, J=8.7 Hz), 7.28-7.58 (8H, m), 7.68 (1H, dd, J=2.4, 8.7 Hz), 8.05 (1H, d, J=2.4 Hz).

(3) Preparation of 3-amino-4-[4-(tert-butyl)benzyloxy]-4'-(trifluoromethoxy)biphenyl The title compound was obtained in the same manner as the Example 3 using the following raw material.

Raw material: 4-[4-(tert-butyl)benzyloxy]-3-nitro-4'-(trifluoromethoxy)biphenyl.

Yield: 83.5% (pale yellow solid).

$^1$H-NMR (CDCl$_3$) δ: 1.34 (9H, s), 3.93 (2H, brs), 5.09 (2H, s), 6.87-6.97 (3H, m), 7.22-7.57 (8H, m).

(4) Preparation of methyl N-{4-[4-(tert-butyl)benzyloxy]-4'-(trifluoromethoxy)biphenyl-3-yl}oxamate A solution of methyl chloroglyoxylate (184 µl, 2.0 mmol) in dichloromethane (1.5 ml) was added dropwise at a slow speed to a mixture of 3-amino-4-[4-(tert-butyl)benzyloxy]-4'-(trifluoromethoxy)biphenyl (415 mg, 1.0 mmol), sodium hydrogencarbonate (168 mg, 2.0 mmol), water (5 ml) and dichloromethane (7 ml), and the mixture was stirred at 0° C. for 2 hours. The reaction mixture was diluted with water, and extracted with ethyl acetate. The organic layer was washed with saturated brine, and dried over anhydrous sodium sulfate. The solvent was evaporated under reduced pressure to give the title compound (456 mg, 90.9%) as a white solid.

$^1$H-NMR (CDCl$_3$) δ: 1.34 (9H, s), 3.97 (3H, s), 5.20 (2H, s), 7.07 (1H, d, J=8.4 Hz), 7.22-7.62 (9H, m), 8.70 (1H, d, J=2.4 Hz), 9.62 (1H, brs).

(5) Preparation of methyl N-{4-[4-(tert-butyl)benzyloxy]-4'-(trifluoromethoxy)biphenyl-3-yl}oxamic acid sodium salt (compound No. 6)

A mixture of methyl N-{4-[4-(tert-butyl)benzyloxy]-4'-(trifluoromethoxy)biphenyl-3-yl}oxamate (436 mg, 0.869 mmol), methanol (2 ml), tetrahydrofuran (2 ml) and 2N aqueous sodium hydroxide (1.3 ml) was stirred at room temperature for 30 minutes. The precipitated solid was collected by filtration and washed with methanol to give the title compound (390 mg, 88.1%) as a white solid.

$^1$H-NMR (DMSO-d$_6$) δ: 1.29 (9H, s), 5.25 (2H, s), 7.26 (1H, s), 7.26 (1H, d, J=8.4 Hz), 7.34 (1H, dd, J=2.4, 8.4 Hz), 7.67 (1H, d, J=8.7 Hz), 8.68 (2H, d, J=2.4 Hz), 10.38 (1H, brs).

Example 7

Preparation of (E)-3-(4-benzyloxy-2'-nitrobiphenyl-3-yl)propenoic acid (compound No. 7)

(1) Preparation of 4-benzyloxy-2'-nitrobiphenyl-3-carbaldehyde

The title compound was obtained in the same manner as the Example 2 (1) using the following raw materials.

Raw materials: 2-benzyloxy-5-bromobenzaldehyde (compound of Example 2 (1)) and 2-nitrophenylboronic acid.

Yield: 29.1% (pale yellow solid).

$^1$H-NMR (CDCl$_3$) δ: 5.17 (2H, s), 6.99 (1H, d, J=8.7 Hz), 7.24 (1H, dd, J=8.7, 2.1 Hz), 7.30-7.51 (7H, m), 7.53-7.61 (2H, m), 7.82 (1H, dd, J=8.7, 1.2 Hz).

(2) Preparation of (E)-3-(4-benzyloxy-2'-nitrobiphenyl-3-yl)propenoic acid (compound No. 7).

The title compound was obtained in the same manner as the Example 2 (3) using the following raw materials.

Raw materials: 4-benzyloxy-2'-nitrobiphenyl-3-carbaldehyde and malonic acid.
Yield: 42.4% (yellow solid).
$^1$H-NMR (DMSO-d$_6$) δ: 5.27 (2H, s), 6.59 (1H, d, J=16.2 Hz), 7.26 (1H, d, J=8.4 Hz), 7.32-7.52 (6H, m), 7.59-7.64 (2H, m), 7.72-7.78 (2H, m), 7.86 (1H, d, J=16.2 Hz), 7.96-8.00 (1H, m), 12.36 (1H, s).

Example 8

Preparation of 3-[2'-amino-4-(benzyloxy)biphenyl-3-yl]propanoic acid (compound No. 8)

The title compound was obtained in the same manner as the Example 3 using the following raw material.
Raw material: (E)-3-(4-benzyloxy-2'-nitrobiphenyl-3-yl)propenoic acid (compound No. 7).
Yield: 39.1% (pink solid).
$^1$H-NMR (DMSO-d$_6$) δ: 2.56 (2H, t, J=7.8 Hz), 2.87 (2H, t, J=7.8 Hz), 4.71 (2H, brs), 5.17 (2H, s), 6.55-6.63 (1H, m), 6.73 (1H, d, J=8.4 Hz), 6.93-7.03 (2H, m), 7.10 (1H, d, J=8.4 Hz), 7.19-7.23 (2H, m), 7.31-7.36 (1H, m), 7.39-7.44 (2H, m), 7.48-7.50 (2H, m), 12.08 (1H, brs).

Example 9

Preparation of {4-[4-(tert-butyl)benzyloxy]-4'-(trifluoromethoxy)biphenyl-3-yl}acetic acid (compound No. 9)

(1) Preparation of 2-[4-(tert-butyl)benzyloxy]phenylacetic acid

A mixture of 4-(tert-butyl)benzyl bromide (2.240 g, 9.861 mmol), 2-hydroxyphenylacetic acid (1.00 g, 6.572 mmol), potassium carbonate (3.996 g, 28.918 mmol), chloroform (6 ml) and methanol (6 ml) was refluxed for 2 hours. The reaction mixture was cooled to room temperature, diluted with water, and extracted with ethyl acetate. The organic layer was washed with water and saturated brine, and dried over anhydrous sodium sulfate. The residue obtained by evaporation of the solvent under reduced pressure was purified by column chromatography on silica gel (n-hexane:ethyl acetate=4:1) to give the title compound (1.007 g, 51.4%) as a white solid.
$^1$H-NMR (CDCl$_3$) δ: 1.32 (9H, s), 3.73 (2H, s), 5.06 (2H, s), 6.92-6.97 (2H, m), 7.21-7.41 (6H, m).

(2) Preparation of 5-bromo-2-[4-(tert-butyl)benzyloxy]phenylacetic acid

The title compound was obtained in the same manner as the Example 1 (1) using the following raw material.
Raw material: 2-[4-(tert-butyl)benzyloxy]phenylacetic acid.
Yield: 49.9% (white solid).
$^1$H-NMR (CDCl$_3$) δ: 1.31 (9H, s), 3.68 (3H, s), 5.02 (2H, s), 6.81 (2H, d, J=9.6 Hz), 7.26-7.39 (6H, m).

(3) Preparation of {4-[4-(tert-butyl)benzyloxy]-4'-(trifluoromethoxy)biphenyl-3-yl}acetic acid (compound No. 9).

The title compound was obtained in the same manner as the Example 1 (2) using the following raw materials.
Raw materials: 5-bromo-2-[4-(tert-butyl)benzyloxy]phenylacetic acid and 4-(trifluoromethoxy)phenylboronic acid.

Yield: 19.9% (white solid).
$^1$H-NMR (DMSO-d$_6$) δ: 1.29 (9H, s), 3.64 (2H, s), 5.14 (2H, s), 7.13 (1H, d, J=8.7 Hz), 7.36-7.43 (6H, m), 7.5-4.7.57 (2H, m), 7.72 (2H, d, J=8.1 Hz), 12.28 (1H, brs).

Example 10

{4-[4-(tert-butyl)benzyloxy]-3',4'-(methylenedioxy)biphenyl-3-yl}acetic acid (compound No. 10)

The title compound was obtained in the same manner as the Example 1 (2) using the following raw materials.
Raw materials: 5-bromo-2-[4-(tert-butyl)benzyloxy]phenylacetic acid (compound of Example 9 (2)) and 3,4-(methylenedioxy)phenylboronic acid.
Yield: 30.3% (white solid).
$^1$H-NMR (DMSO-d$_6$) δ: 1.28 (9H, s), 3.62 (2H, s), 5.11 (2H, s), 6.04 (2H, s), 6.96 (2H, d, J=8.1 Hz), 7.05-7.09 (2H, m), 7.17 (2H, d, J=1.5 Hz), 7.35-7.48 (6H, m), 12.23 (1H, s).

Example 11

Preparation of [4-(3,5-dimethylbenzyloxy)-4'-(trifluoromethoxy)biphenyl-3-yl]acetic acid (compound No. 11)

(1) Preparation of 2-(3,5-dimethylbenzyloxy)phenylacetic acid

The title compound was obtained in the same manner as the Example 9 (1) using the following raw materials.
Raw materials: 2-hydroxyphenylacetic acid and 3,5-dimethylbenzyl bromide.
Yield: 33.9% (white solid).
$^1$H-NMR (CDCl$_3$) δ: 2.29 (6H, s), 3.72 (2H, s), 5.00 (2H, s), 6.91-6.96 (3H, m), 7.00 (2H, s), 7.19-7.23 (1H, m), 7.24-7.28 (1H, m).

(2) Preparation of 5-bromo-2-(3,5-dimethylbenzyloxy)phenylacetic acid

The title compound was obtained in the same manner as the Example 1 (1) using the following raw material.
Raw material: 2-(3,5-dimethylbenzyloxy)phenylacetic acid.
Yield: 38.5% (white solid).
$^1$H-NMR (CDCl$_3$) δ: 2.29 (6H, s), 3.72 (2H, s), 5.00 (2H, s), 6.91-6.96 (3H, m), 7.00 (2H, s), 7.19-7.23 (1H, m), 7.24-7.28 (1H, m).

(3) Preparation of [4-(3,5-dimethylbenzyloxy)-4'-(trifluoromethoxy)biphenyl-3-yl]acetic acid (compound No. 11).

The title compound was obtained in the same manner as the Example 1 (2) using the following raw materials.
Raw materials: 5-bromo-2-(3,5-dimethylbenzyloxy)phenylacetic acid and 4 (trifluoromethoxy)phenylboronic acid.

Yield: 7.2% (white solid).

$^1$H-NMR (CDCl$_3$) δ: 2.30 (6H, s), 3.78 (2H, s), 5.05 (2H, s), 6.93-7.02 (4H, m), 7.23-7.27 (2H, m), 7.40-7.45 (2H, m), 7.53 (2H, d, J=8.7 Hz).

Example 12

Preparation of (Z)-3-{4-[4-(tert-butyl)phenoxy]-4'-(trifluoromethoxy)biphenyl-3-yl}propenoic acid (compound No. 12)

(1) Preparation of 4-fluoro-4'-(trifluoromethoxy)biphenyl-3-carbaldehyde

The title compound was obtained in the same manner as the Example 1 (2) using the following raw materials.

Raw materials: 5-bromo-2-fluorobenzaldehyde and 4-(trifluoromethoxy)phenylboronic acid.

Yield: 91.6% (pale yellow oil).

$^1$H-NMR (CDCl$_3$) δ: 7.24-7.33 (3H, m), 7.55-7.61 (2H, m), 7.76-7.82 (1H, m), 8.05 (1H, dd, J=2.4, 6.3 Hz), 10.42 (1H, s).

(2) Preparation of 4-[4-(tert-butyl)phenoxy]-4'-(trifluoromethoxy)biphenyl-3-carbaldehyde A mixture of 4-fluoro-4'-(trifluoromethoxy)biphenyl-3-carbaldehyde (750 mg, 2.639 mmol), 4-(tert-butyl)phenol (436 mg, 2.903 mmol), potassium carbonate (547 mg, 3.958 mmol) and dimethylacetamide (4 ml) was stirred at 160° C. for 1 hour. The reaction mixture was cooled to room temperature, diluted with water, and extracted with ethyl acetate. The organic layer was washed with water and saturated brine, and dried over anhydrous sodium sulfate. The residue obtained by evaporation of the solvent under reduced pressure was purified by column chromatography on silica gel (n-hexane:ethyl acetate=15:1) to give the title compound (598 mg, 54.7%) as a pale yellow solid.

$^1$H-NMR (CDCl$_3$) δ: 1.35 (9H, s), 1.27 (1H, d, J=8.7 Hz), 6.98 (2H, d, J=8.7 Hz), 7.28 (2H, d, J=8.4 Hz), 7.43 (2H, d, J=8.7 Hz), 7.59 (2H, d, J=8.4 Hz), 7.68 (1H, dd, J=2.7, 8.7 Hz), 8.12 (1H, d, J=2.7 Hz), 10.58 (1H, t, J=8.1 Hz).

(3) Preparation of methyl (Z)-3-{4-[4-(tert-butyl)phenoxy]-4'-(trifluoromethoxy)biphenyl-3-yl}propenoate A solution of potassium bis(trimethylsilyl)amide (414 mg, 1.973 mmol) in tetrahydrofuran (3 ml) was added dropwise at a slow speed to a mixture of bis(2,2,2-trifluoroethyl) (methoxycarbonylmethyl)phosphonate (627 mg, 1.973 mmol), 18-crown-6 (2.048 g, 7.750 mmol) and tetrahydrofuran (20 ml) at −78° C. under argon atmosphere. A solution of 4-fluoro-4'-(trifluoromethoxy)biphenyl-3-carbaldehyde (584 mg, 1.409 mmol) in tetrahydrofuran (3 ml) was added dropwise at a slow speed to the mixture at −78° C. under argon atmosphere, and the mixture was stirred at −78° C. for 30 minutes. Saturated aqueous ammonium chloride was added to the reaction mixture. The residue obtained by evaporation of the solvent under reduced pressure was diluted with ethyl acetate, washed with water, and dried over anhydrous sodium sulfate. The residue obtained by evaporation of the solvent under reduced pressure was purified by column chromatography on silica gel (n-hexane:ethyl acetate=15:1) to give the title compound (597 mg, 90.1%) as a pale yellow oil.

$^1$H-NMR (CDCl$_3$) δ: 1.32 (9H, s), 3.71 (3H, s), 6.04 (1H, d, J=12.6 Hz), 6.90-6.98 (3H, m), 7.20-7.31 (3H, m), 7.36 (2H, d, J=9.6 Hz), 7.44 (1H, dd, J=2.4, 8.4 Hz), 7.59 (2H, d, J=8.7 Hz), 7.95 (1H, d, J=2.4 Hz).

(4) Preparation of (Z)-3-{4-[4 (tert-butyl)phenoxy]-4'-(trifluoromethoxy)biphenyl-3-yl}propenoic acid (compound No. 12).

A mixture of methyl (Z)-3-{4-[4-(tert-butyl)phenoxy]-4'-(trifluoromethoxy)biphenyl-3-yl}propenoate (590 mg, 1.293 mmol), methanol (1 ml), tetrahydrofuran (4 ml) and 2N aqueous sodium hydroxide (1.94 ml) was stirred at 60° C. for 1 hour. The reaction mixture was cooled to room temperature, acidified by addition of 2N hydrochloric acid, and extracted with ethyl acetate. The organic layer was washed with saturated brine, and dried over anhydrous sodium sulfate. The solvent was evaporated under reduced pressure to give the title compound (550 mg, 93.2%) as a pale yellow oil.

$^1$H-NMR (CDCl$_3$) δ: 1.32 (9H, s), 3.49 (2H, s), 6.06 (1H, d, J=12.6 Hz), 6.91 (1H, d, J=8.4 Hz), 6.95 (2H, d, J=8.7 Hz), 7.20-7.24 (2H, m), 7.30-7.36 (3H, m), 7.43 (1H, dd, J=2.1, 8.4 Hz), 7.50-7.54 (2H, m), 7.90 (1H, d, J=2.1 Hz).

Example 13

Preparation of 3-{4-[4-(tert-butyl)phenoxy]-4'-(trifluoromethoxy)biphenyl-3-yl}propanoic acid (compound No. 13)

The title compound was obtained in the same manner as the Example 3 using the following raw material.

Raw material: (Z)-3-{4-[4-(tert-butyl)phenoxy]-4'-(trifluoromethoxy)biphenyl-3-yl}propenoic acid (compound No. 12).

Yield: 75.4% (colorless oil).

$^1$H-NMR (CDCl$_3$) δ: 1.33 (9H, s), 2.76 (2H, t, J=7.5 Hz), 3.06 (2H, t, J=7.5 Hz), 6.89 (1H, d, J=6.9 Hz), 6.93 (2H, d, J=8.7 Hz), 7.24-7.39 (5H, m), 7.46 (1H, d, J=2.1 Hz), 7.55 (2H, d, J=8.7 Hz).

Example 14

Preparation of (Z)-3-[4-(4-carboxyphenoxy)-4'-(trifluoromethoxy)biphenyl-3-yl]propenoic acid (compound No. 14)

(1) Preparation of methyl 4-[3-formyl-4'-(trifluoromethoxy)biphenyl-3-yl]oxybenzoate The title compound was obtained in the same manner as the Example 12 (2) using the following raw materials.

Raw materials: 4-fluoro-4'-(trifluoromethoxy)biphenyl-3-carbaldehyde (compound of Example 12 (1)) and methyl 4-hydroxybenzoate.

Yield: 40.5% (pale yellow solid).

$^1$H-NMR (CDCl$_3$) δ: 3.93 (3H, s), 7.09 (1H, d, J=8.7 Hz), 7.12 (2H, d, J=8.4 Hz), 7.32 (2H, d, J=8.4 Hz), 7.62 (2H, d, J=8.4 Hz), 7.77 (1H, dd, J=2.4, 8.7 Hz), 8.10 (2H, d, J=8.4 Hz), 8.16 (1H, d, J=2.4 Hz), 10.47 (1H, s).

(2) Preparation of methyl (Z)-3-{4-[4-(methoxycarbonyl)phenoxy]-4'-(trifluoromethoxy)biphenyl-3-yl}propenoate The title compound was obtained in the same manner as the Example 12 (3) using the following raw materials.

Raw materials: methyl 4-[3-formyl-4'-(trifluoromethoxy)biphenyl-3-yl]oxybenzoate and bis(2,2,2-trifluoroethyl)(methoxycarbonylmethyl)phosphonate.

Yield: 84.3% (pale yellow oil).

$^1$H-NMR (CDCl$_3$) δ: 3.69 (3H, s), 3.90 (3H, s), 5.01 (1H, d, J=12.3 Hz), 6.99 (2H, d, J=9.3 Hz), 7.06 (1H, d, J=8.7 Hz), 7.09 (1H, d, J=12.3 Hz), 7.29 (2H, d, J=8.4 Hz), 7.54 (1H, dd, J=2.4, 8.7 Hz), 7.61 (2H, d, J=8.4 Hz), 7.92 (1H, d, J=2.4 Hz), 8.00 (2H, d, J=9.3 Hz).

(3) Preparation of (Z)-3-[4-(4-carboxyphenoxy)-4'-(trifluoromethoxy)biphenyl-3-yl]propenoic acid (compound No. 14)

The title compound was obtained in the same manner as the Example 12 (4) using the following raw material.

Raw material: methyl (Z)-3-{4-[4-(methoxycarbonyl)phenoxy]-4'-(trifluoromethoxy)biphenyl-3-yl}propenoate.

Yield: 58.5% (white solid).

$^1$H-NMR (DMSO-d$_6$) δ: 6.05 (1H, d, J=12.6 Hz), 6.97-7.06 (3H, m), 7.15 (1H, d, J=9.0 Hz), 7.45-7.50 (2H, m), 7.71 (1H, dd, J=2.1, 9.0 Hz), 7.78 (2H, d, J=8.7 Hz), 7.92-7.97 (3H, m), 12.69 (1H, brs).

Example 15

Preparation of 3-[4-(4-carboxyphenoxy)-4'-(trifluoromethoxy)biphenyl-3-yl]propanoic acid (compound No. 15)

The title compound was obtained in the same manner as the Example 3 using the following raw material.

Raw material: (Z)-3-[4 (4-carboxyphenoxy)-4'-(trifluoromethoxy)biphenyl-3-yl]propenoic acid (compound No. 14).

Yield: 100% (white solid).

$^1$H-NMR (DMSO-d$_6$) δ: 2.57 (2H, t, J=7.5 Hz), 2.85 (2H, t, J=7.5 Hz), 7.03 (2H, d, J=8.7 Hz), 7.10 (1H, d, J=8.4 Hz), 7.46 (2H, d, J=8.7 Hz), 7.60 (1H, dd, J=2.4, 8.4 Hz), 7.72 (1H, d, J=2.4 Hz), 7.81 (2H, d, J=8.7 Hz), 7.96 (2H, d, J=8.7 Hz).

Example 16

Preparation of (E)-3-{4-[4-(trifluoromethoxy)phenoxy]-4'-(trifluoromethoxy)biphenyl-3-yl}propenoic acid (compound No. 16)

(1) Preparation of 5-bromo-2-[(trifluoromethoxy)phenoxy]benzaldehyde

A mixture of 5-bromo-2-fluorobenzaldehyde (1.07 g, 5.280 mmol), 4-(trifluoromethoxy)phenol (940 mg, 5.280 mmol), potassium carbonate (1.46 g, 10.560 mmol), copper (II) oxide (420 mg, 5.280 mmol) and pyridine (10 ml) was stirred at 180° C. for 6 hours. The reaction mixture was cooled to room temperature and filtered through celite. The filtrate was diluted with water, extracted with water and saturated brine, and dried over anhydrous sodium sulfate. The residue obtained by evaporation of the solvent under reduced pressure was purified by column chromatography on silica gel (n-hexane:ethyl acetate=6:1) to give the title compound (1.58 g, 83.1%) as a brown oil.

$^1$H-NMR (CDCl$_3$) δ: 6.18 (1H, d, J=8.7 Hz), 7.09 (2H, d, J=8.7 Hz), 7.25-7.28 (2H, m), 7.61-7.65 (1H, m), 8.05 (1H, d, J=2.4 Hz), 10.41 (1H, s).

(2) Preparation of 4-[4-(trifluoromethoxy)phenoxy]-4'-(trifluoromethoxy)biphenyl-3-carbaldehyde The title compound was obtained in the same manner as the Example 1 (2) using the following raw materials.

Raw materials: 5-bromo-2-[(trifluoromethoxy)phenoxy]benzaldehyde and 4 (trifluoromethoxy)phenylboronic acid.

Yield: 94.3% (clear yellow oil).

$^1$H-NMR (CDCl$_3$) δ: 7.00 (1H, d, J=8.4 Hz), 7.12-7.15 (2H, m), 7.26-7.32 (4H, m), 7.59-7.62 (2H, m), 7.73 (1H, dd, J=8.4, 2.4 Hz), 8.15 (1H, d, J=2.4 Hz), 10.54 (1H, s).

(3) Preparation of (E)-3-{4-[4-(trifluoromethoxy)phenoxy]-4'-(trifluoromethoxy)biphenyl-3-yl}propenoic acid (compound No. 16)

The title compound was obtained in the same manner as the Example 2 (3) using the following raw materials.

Raw materials: 4-[4-(trifluoromethoxy)phenoxy]-4'-(trifluoromethoxy)biphenyl-3-carbaldehyde and malonic acid.

Yield: 64.5% (white solid).

$^1$H-NMR (CDCl$_3$) δ: 6.64 (1H, d, J=16.2 Hz), 6.96 (1H, d, J=8.7 Hz), 7.05-7.08 (2H, m), 7.23-7.33 (4H, m), 7.53 (1H, dd, J=8.7, 2.4 Hz), 7.57-7.60 (2H, m), 7.82 (1H, d, J=2.4 Hz), 8.12 (1H, d, J=16.2 Hz).

Example 17

Preparation of 3-{4-[4-(trifluoromethoxy)phenoxy]-4'-(trifluoromethoxy)biphenyl-3-yl}propanoic acid (compound No. 17)

The title compound was obtained in the same manner as the Example 3 using the following raw material.

Raw material: (E)-3-{4-[4-(trifluoromethoxy)phenoxy]-4'-(trifluoromethoxy)biphenyl-3-yl}propenoic acid (compound No. 16).

Yield: 87.8% (colorless oil).

$^1$H-NMR (CDCl$_3$) δ: 2.74 (2H, t, J=7.5 Hz), 3.03 (2H, t, J=7.5 Hz), 6.92 (1H, d, J=8.7 Hz), 6.98-7.02 (2H, m), 7.20 (2H, d, J=8.1 Hz), 7.26-7.29 (2H, m), 7.38 (1H, dd, J=8.7, 2.1 Hz), 7.48 (1H, d, J=2.1 Hz), 7.53-7.58 (2H, m).

Example 18

Preparation of N-{4-[4-(tert-butyl)benzyloxy]-4'-(trifluoromethoxy)biphenyl-3-yl}-N-methyloxamic acid (compound No. 18)

(1) Preparation of methyl N-{4-[4-(tert-butyl)benzyloxy]-4'-(trifluoromethoxy)biphenyl-3-yl}-N-methyloxamate A mixture of methyl N-{4-[4-(tert-butyl)benzyloxy]-4'-(trifluoromethoxy)biphenyl-3-yl}oxamate (compound of Example 6 (4); 3.0 g, 5.982 mmol), methyl iodide (9.387 g, 66.180 mmol), potassium carbonate (2.480 g, 17.946 mmol), 18-crown-6 (158 mg, 0.598 mmol) and acetonitrile (50 ml) was stirred at 85° C. for 3 hours. The reaction mixture was cooled to room temperature, diluted with water, and extracted with ethyl acetate. The organic layer was washed with saturated brine, and dried over anhydrous sodium sulfate. The residue obtained by evaporation of the solvent under reduced pressure was purified by column chromatography on silica gel (n-hexane:ethyl acetate=5:1) to give the title compound (3.066 g, 99.4%) as a colorless oil.

¹H-NMR (CDCl₃) δ: 1.33 (9H, s), 3.12 (3H, s), 3.55 (3H, s), 5.15 (2H, s), 7.08 (1H, d, J=8.4 Hz), 7.24-7.29 (2H, m), 7.34-7.53 (8H, m).

(2) Preparation of N-{4-[4-(tert-butyl)benzyloxy]-4'-(trifluoromethoxy)biphenyl-3-yl}-N-methyloxamic acid (compound No. 18)

The title compound was obtained in the same manner as the Example 12 (4) using the following raw material.
Raw material: methyl N-{4-[4-(tert-butyl)benzyloxy]-4'-(trifluoromethoxy)biphenyl-3-yl}-N-methyloxamate.
Yield: 90.1% (white solid).
¹H-NMR (DMSO-d₆) δ: 1.29 (9H, s), 3.18 (3H, s), 5.13-5.26 (2H, m), 7.28 (2H, d, J=8.7 Hz), 7.39-7.46 (6H, m), 7.62 (1H, d, J=2.1 Hz), 7.69 (1H, dd, J=2.1, 8.7 Hz), 7.73 (2H, d, J=9.0 Hz).

Example 19

Preparation of (E)-3-[4-(4-chlorobenzyloxy)-4'-(trifluoromethoxy)biphenyl-3-yl]propenoic acid (compound No. 19).

(1) Preparation of 4-hydroxy-4'-(trifluoromethoxy)biphenyl-3-carbaldehyde

The title compound was obtained in the same manner as the Example 1 (2) using the following raw materials.
Raw materials: 5-bromosalicylaldehyde and 4-(trifluoromethoxy)phenylboronic acid.
Yield: 78.1% (yellow solid).
¹H-NMR (CDCl₃) δ: 7.09 (1H, d, J=8.1 Hz), 7.30 (2H, d, J=7.8 Hz), 7.54-7.59 (2H, m), 7.72-7.76 (2H, m), 9.98 (1H, s), 11.03 (1H, s).

(2) Preparation of 4-(4-chlorobenzyloxy)-4'-(trifluoromethoxy)biphenyl-3-carbaldehyde The title compound was obtained in the same manner as the Example 2 (1) using the following raw materials.
Raw materials: 4-hydroxy-4'-(trifluoromethoxy)biphenyl-3-carbaldehyde and 4-chlorobenzyl chloride.
Yield: 73.1% (white solid).
¹H-NMR (CDCl₃) δ: 5.22 (2H, s), 7.11 (1H, d, J=8.7 Hz), 7.26-7.29 (2H, m), 7.39-7.41 (4H, m), 7.56-7.59 (2H, m), 7.74 (1H, dd, J=8.7, 2.4 Hz), 8.07 (1H, d, J=2.4 Hz), 10.58 (1H, s).

(3) Preparation of (E)-3-[4-(4-chlorobenzyloxy)-4'-(trifluoromethoxy)biphenyl-3-yl]propenoic acid (compound No. 19)

The title compound was obtained in the same manner as the Example 2 (3) using the following raw materials.
Raw materials: 4-(4-chlorobenzyloxy)-4'-(trifluoromethoxy)biphenyl-3-carbaldehyde and malonic acid.
Yield: 84.2% (white solid).
¹H-NMR (CDCl₃) δ: 5.20 (2H, s), 6.62 (1H, d, J=16.2 Hz), 7.01 (1H, d, J=8.4 Hz), 7.29 (2H, d, J=8.7 Hz), 7.38-7.39 (4H, m), 7.50-7.57 (3H, m), 7.74 (1H, d, J=2.4 Hz), 8.18 (1H, d, J=16.2 Hz).

Example 20

Preparation of 3-[4-(4-chlorobenzyloxy)-4'-(trifluoromethoxy)biphenyl-3-yl]propanoic acid (compound No. 20)

The title compound was obtained in the same manner as the Example 3 using the following raw material.
Raw material: (E)-3-[4-(4-chlorobenzyloxy)-4'-(trifluoromethoxy)biphenyl-3-yl]propenoic acid (compound No. 19).
Yield: 50.0% (white solid).
¹H-NMR (CDCl₃) δ: 2.72 (2H, t, J=7.2 Hz), 3.05 (2H, t, J=7.2 Hz), 5.10 (2H, s), 6.93 (1H, d, J=8.4 Hz), 7.22-7.26 (2H, m), 7.35-7.40 (6H, m), 7.51-7.54 (2H, m).

Example 21

Preparation of (E)-3-[4-(4-fluorobenzyloxy)-4'-(trifluoromethoxy)biphenyl-3-yl]propenoic acid (compound No. 21)

(1) Preparation of 4-(4-fluorobenzyloxy)-4'-(trifluoromethoxy)biphenyl-3-carbaldehyde The title compound was obtained in the same manner as the Example 2 (1) using the following raw materials.
Raw materials: 4-hydroxy-4'-(trifluoromethoxy)biphenyl-3-carbaldehyde (compound of Example 19 (1)) and 4-fluorobenzyl chloride.
Yield: 96.8% (brown solid).
¹H-NMR (CDCl₃) δ: 5.21 (2H, s), 7.09-7.15 (3H, m), 7.26-7.30 (2H, m), 7.42-7.47 (2H, m), 7.56-7.59 (2H, m), 7.75 (1H, dd, J=8.7, 2.4 Hz), 8.07 (1H, d, J=2.4 Hz), 10.57 (1H, s).

(2) Preparation of (E)-3-[4-(4-fluorobenzyloxy)-4'-(trifluoromethoxy)biphenyl-3-yl]propenoic acid (compound No. 21)

The title compound was obtained in the same manner as the Example 2 (3) using the following raw materials.
Raw materials: 4-(4-fluorobenzyloxy)-4'-(trifluoromethoxy)biphenyl-3-carbaldehyde and malonic acid.
Yield: 62.5% (white solid).
¹H-NMR (CDCl₃) δ: 5.19 (2H, s), 6.61 (1H, d, J=16.2 Hz), 7.03 (1H, d, J=8.7 Hz), 7.07-7.15 (2H, m), 7.29 (2H, d, J=8.4 Hz), 7.41-7.46 (2H, m), 7.51-7.57 (3H, m), 7.74 (1H, d, J=2.1 Hz), 8.18 (1H, d, J=16.2 Hz).

Example 22

Preparation of 3-[4-(4-fluorobenzyloxy)-4'-(trifluoromethoxy)biphenyl-3-yl]propanoic acid (compound No. 22)

The title compound was obtained in the same manner as the Example 3 using the following raw material.
Raw material: (E)-3-[4-(4-fluorobenzyloxy)-4'-(trifluoromethoxy)biphenyl-3-yl]propenoic acid (compound No. 21).
Yield: 55.9% (white solid).
¹H-NMR (CDCl₃) δ: 2.72 (2H, t, J=7.5 Hz), 3.05 (2H, t, J=7.5 Hz), 5.10 (2H, s), 6.96 (1H, d, J=8.4 Hz), 7.01 (2H, t, J=8.7 Hz), 7.25 (2H, d, J=8.1 Hz), 7.36-7.44 (4H, m), 7.51-7.54 (2H, m).

Example 23

Preparation of (E)-3-{4'-(trifluoromethoxy)-4-[2-(trifluoromethyl)benzyloxy]biphenyl-3-yl}propenoic acid (compound No. 23)

(1) Preparation of 4'-(trifluoromethoxy)-4-[2-(trifluoromethyl)benzyloxy]biphenyl-3-carbaldehyde The title compound was obtained in the same manner as the Example 2 (1) using the following raw materials.
Raw materials: 4-hydroxy-4'-(trifluoromethoxy)biphenyl-3-carbaldehyde (compound of Example 19 (1)) and 2-(trifluoromethyl)benzyl chloride.
Yield: 72.9% (pale pink solid).
$^1$H-NMR (CDCl$_3$) δ: 5.45 (2H, s), 7.11 (1H, d, J=8.7 Hz), 7.29 (2H, d, J=8.7 Hz), 7.49 (1H, t, J=7.2 Hz), 7.56-7.65 (3H, m), 7.73-7.77 (3H, m), 8.09 (1H, d, J=2.4 Hz), 10.62 (1H, s).

(2) Preparation of (E)-3-{4'-(trifluoromethoxy)-4-[2-(trifluoromethyl)benzyloxy]biphenyl-3-yl}propenoic acid (compound No. 23)

The title compound was obtained in the same manner as the Example 2 (3) using the following raw materials.
Raw materials: 4'-(trifluoromethoxy)-4-[2-(trifluoromethyl)benzyloxy]biphenyl-3-carbaldehyde and malonic acid.
Yield: 89.7% (white solid).
$^1$H-NMR (CDCl$_3$) δ: 5.43 (2H, s), 6.63 (1H, d, J=16.2 Hz), 6.98 (1H, d, J=8.4 Hz), 7.29 (2H, d, J=8.1 Hz), 7.44-7.63 (5H, m), 7.71-7.77 (3H, m), 8.25 (1H, d, J=16.2 Hz).

Example 24

Preparation of 3-{4'-(trifluoromethoxy)-4-[2-(trifluoromethyl)benzyloxy]biphenyl-3-yl}propanoic acid (compound No. 24)

The title compound was obtained in the same manner as the Example 3 using the following raw material.
Raw material: (E)-3-{4'-(trifluoromethoxy)-4-[2-(trifluoromethyl)benzyloxy]biphenyl-3-yl}propenoic acid (compound No. 23).
Yield: 79.1% (white solid).
$^1$H-NMR (CDCl$_3$) δ: 2.76 (2H, t, J=7.5 Hz), 3.10 (2H, t, J=7.5 Hz), 5.34 (2H, s), 6.92 (1H, d, J=8.4 Hz), 7.25 (2H, t, J=7.8 Hz), 7.37 (1H, dd, J=8.4, 2.4 Hz), 7.41 (1H, d, J=2.4 Hz), 7.44 (1H, d, J=7.8 Hz), 7.50-7.61 (3H, m), 7.70-7.75 (2H, m).

Example 25

Preparation of (E)-3-{4'-(trifluoromethoxy)-4-[4-(trifluoromethyl)benzyloxy]biphenyl-3-yl}propenoic acid (compound No. 25)

(1) Preparation of 4'-(trifluoromethoxy)-4-[4-(trifluoromethyl)benzyloxy]biphenyl-3-carbaldehyde The title compound was obtained in the same manner as the Example 2 (1) using the following raw materials.
Raw materials: 4-hydroxy-4'-(trifluoromethoxy)biphenyl-3-carbaldehyde (compound of Example 19 (1)) and 4-(trifluoromethyl)benzyl chloride.
Yield: 100.0% (clear brown oil).
$^1$H-NMR (CDCl$_3$) δ: 5.32 (2H, s), 7.11 (1H, d, J=8.7 Hz), 7.29 (2H, d, J=8.7 Hz), 7.65-7.61 (4H, m), 7.70 (2H, d, J=8.4 Hz), 7.75 (1H, dd, J=8.7, 2.7 Hz), 8.09 (1H, d, J=2.7 Hz).

(2) Preparation of (E)-3-{4'-(trifluoromethoxy)-4-[4-(trifluoromethyl)benzyloxy]biphenyl-3-yl}propenoic acid (compound No. 25)

The title compound was obtained in the same manner as the Example 2 (3) using the following raw materials.
Raw materials: 4'-(trifluoromethoxy)-4-[4 (trifluoromethyl)benzyloxy]biphenyl-3-carbaldehyde and malonic acid.
Yield: 53.4% (white solid).
$^1$H-NMR (CDCl$_3$) δ: 5.29 (2H, s), 6.63 (1H, d, J=16.2 Hz), 7.00 (1H, d, J=8.7 Hz), 7.29 (2H, d, J=8.1 Hz), 7.51-7.59 (5H, m), 7.69 (2H, d, J=8.7 Hz), 7.76 (1H, d, J=2.1 Hz), 8.21 (1H, d, J=16.2 Hz).

Example 26

Preparation of 3-{4'-(trifluoromethoxy)-4-[4-(trifluoromethyl)benzyloxy]biphenyl-3-yl}propanoic acid (compound No. 26).

The title compound was obtained in the same manner as the Example 3 using the following raw material.
Raw material: (E)-3-{4'-(trifluoromethoxy)-4-[4-(trifluoromethyl)benzyloxy]biphenyl-3-yl}propenoic acid (compound No. 25).
Yield: 67.3% (white solid).
$^1$H-NMR (CDCl$_3$) δ: 2.74 (2H, t, J=7.5 Hz), 3.08 (2H, t, J=7.5 Hz), 5.19 (2H, s), 6.92 (1H, d, J=8.1 Hz), 7.23-7.26 (2H, m), 7.35-7.41 (2H, m), 7.50-7.57 (4H, m), 7.66 (2H, d, J=7.8 Hz).

Example 27

Preparation of (E)-3-[4-(4-fluorobenzyloxy)-4'-(trifluoromethoxy)biphenyl-3-yl]propenoic acid (compound No. 27)

(1) Preparation of 4-(2-methoxybenzyloxy)-4'-(trifluoromethoxy)biphenyl-3-carbaldehyde The title compound was obtained in the same manner as the Example 2 (1) using the following raw materials.
Raw materials: 4-hydroxy-4'-(trifluoromethoxy)biphenyl-3-carbaldehyde (compound of Example 19 (1)) and 2-methoxybenzyl chloride.
Yield: 77.0% (white solid).
$^1$H-NMR (CDCl$_3$) δ: 3.89 (3H, s), 5.29 (2H, s), 6.95 (1H, d, J=8.4 Hz), 6.98-7.03 (1H, m), 7.19 (1H, d, J=8.4 Hz), 7.26-7.29 (2H, m), 7.32-7.38 (1H, m), 7.45-7.48 (1H, m), 7.56-7.61 (2H, m), 7.74 (1H, dd, J=8.4 Hz, J=2.4 Hz), 8.06 (1H, d, J=2.4 Hz).

(2) Preparation of (E)-3-[4-(2-methoxybenzyloxy)-4'-(trifluoromethoxy)biphenyl-3-yl]propenoic acid (compound No. 27)

The title compound was obtained in the same manner as the Example 2 (3) using the following raw materials.
Raw materials: 4-(2-methoxybenzyloxy)-4'-(trifluoromethoxy)biphenyl-3-carbaldehyde and malonic acid.
Yield: 65.4% (white solid).
$^1$H-NMR (CDCl$_3$) δ: 3.90 (3H, s), 5.28 (2H, s), 6.65 (1H, d, J=16.2 Hz), 6.94 (1H, d, J=8.1 Hz), 6.97-7.02 (1H, m), 7.09

(1H, d, J=8.7 Hz), 7.26-7.36 (3H, m), 7.44 (1H, dd, J=8.1, 1.5 Hz), 7.50-7.57 (3H, m), 7.72 (1H, d, J=2.1 Hz), 8.21 (1H, d, J=16.2 Hz).

Example 28

3-[4-(2-methoxybenzyloxy)-4'-(trifluoromethoxy) biphenyl-3-yl]propanoic acid (compound No. 28)

The title compound was obtained in the same manner as the Example 3 using the following raw material.
Raw material: (E)-3-[4-(2-methoxybenzyloxy)-4'-(trifluoromethoxy)biphenyl-3-yl]propenoic acid (compound No. 27).
Yield: 74.8% (white solid). $^1$H-NMR (CDCl$_3$) δ: 2.76 (2H, t, J=7.2 Hz), 3.06 (2H, t, J=7.2 Hz), 3.87 (3H, s), 5.17 (2H, s), 6.91-7.03 (3H, m), 7.23-7.57 (8H, m).

Example 29

Preparation of (Z)-3-[4-benzyloxy-4'-(trifluoromethoxy)biphenyl-3-yl]propenoic acid (compound No. 29)

(1) Preparation of methyl (Z)-3-[4-benzyloxy-4'-(trifluoromethoxy)biphenyl-3-yl]propenoate The title compound was obtained in the same manner as the Example 12 (3) using the following raw materials.
Raw materials: 4-benzyloxy-4'-(trifluoromethoxy)biphenyl-3-carbaldehyde (compound of Example 2 (2)) and bis(2,2,2-trifluoroethyl) (methoxycarbonylmethyl)phosphonate.
Yield: 66.1% (colorless oil).
$^1$H-NMR (CDCl$_3$) δ: 3.68 (3H, s), 5.14 (2H, s), 7.01 (1H, d, J=8.7 Hz), 7.24-7.50 (9H, m), 7.54-7.59 (3H, m), 7.91 (1H, d, J=2.1 Hz).

(2) Preparation of (Z)-3-[4-benzyloxy-4'-(trifluoromethoxy)biphenyl-3-yl]propenoic acid (compound No. 29).

The title compound was obtained in the same manner as the Example 12 (4) using the following raw material.
Raw material: methyl (Z)-3-[4-benzyloxy-4'-(trifluoromethoxy)biphenyl-3-yl]propenoate.
Yield: 55.3% (white solid).
$^1$H-NMR (CDCl$_3$) δ: 5.14 (2H, s), 6.04 (1H, d, J=12.9 Hz), 7.01 (1H, d, J=8.7 Hz), 7.19 (2H, d, J=8.1 Hz), 7.32-7.51 (9H, m), 7.86 (1H, d, J=2.4 Hz).

Example 30

Preparation of (Z)-3-{4-[4-(tert-butyl)benzyloxy]-4'-(trifluoromethoxy)biphenyl-3-yl}propenoic acid (compound No. 30).

(1) Preparation of methyl (Z)-3-{4-[4-(tert-butyl) benzyloxy]-4'-(trifluoromethoxy)biphenyl-3-yl}propenoate The title compound was obtained in the same manner as the Example 12 (3) using the following raw materials.
Raw materials: 4-[4-(tert-butyl)benzyloxy]-4'-(trifluoromethoxy)biphenyl-3-carbaldehyde (compound of Example 4 (2)) and bis(2,2,2-trifluoroethyl) (methoxycarbonylmethyl)phosphonate.
Yield: 64.2% (white solid).
$^1$H-NMR (CDCl$_3$) δ: 1.36 (9H, s), 3.69 (3H, s), 5.11 (2H, s), 7.02 (1H, d, J=8.4 Hz), 7.23-7.45 (7H, m), 7.49 (1H, dd, J=2.4, 8.4 Hz), 7.54-7.60 (2H, m), 7.92 (1H, d, J=2.4 Hz).

(2) Preparation of (Z)-3-{4-[4-(tert-butyl)benzyloxy]-4'-(trifluoromethoxy)biphenyl-3-yl}propenoic acid (compound No. 30)

The title compound was obtained in the same manner as the Example 12 (4) using the following raw material.
Raw material: methyl (Z)-3-{4-[4-(tert-butyl)benzyloxy]-4'-(trifluoromethoxy)biphenyl-3-yl}propenoate.
Yield: 83.4% (white solid).
$^1$H-NMR (CDCl$_3$) δ: 1.33 (9H, s), 5.10 (2H, s), 6.02 (1H, d, J=12.3 Hz), 7.01 (1H, d, J=8.7 Hz), 7.17 (2H, d, J=8.7 Hz), 7.34-7.50 (8H, m), 7.87 (1H, d, J=2.4 Hz).

Example 31

Preparation of 3-{4-[4-(tert-butyl)benzyloxy]-3'-carboxybiphenyl-3-yl}propanoic acid (compound No. 31)

(1) Preparation of ethyl (E)-3-{5-bromo-2-[4-(tert-butyl)benzyloxy]phenyl}propenoate A solution of triethyl phosphonoacetate (1.356 g, 6.048 mmol) in tetrahydrofuran (45 ml) was added dropwise at a slow speed to sodium hydride (264 mg, 6.048 mmol) at room temperature under argon atmosphere, and the mixture was stirred at room temperature for 30 minutes. A solution of 2-[4-(tert-butyl)benzyloxy]-5-bromobenzaldehyde (compound of Example 4 (1); 1.5 g, 4.319 mmol) in tetrahydrofuran (25 ml) was added dropwise at a slow speed to the mixture at 0° C. under argon atmosphere, and the mixture was stirred at room temperature overnight. A small portion of saturated aqueous ammonium chloride was added to the reaction mixture. The residue obtained by evaporation of tetrahydrofuran under reduced pressure was extracted with ethyl acetate. The organic layer was washed with water, and dried over anhydrous sodium sulfate. The residue obtained by evaporation of the solvent under reduced pressure was purified by column chromatography on silica gel (n-hexane:ethyl acetate=10:1) to give the title compound (1.59 g, 88.2%) as a colorless oil.
$^1$H-NMR (CDCl$_3$) δ: 1.24-1.43 (12H, m), 4.25 (2H, q, J=7.2 Hz), 5.10 (2H, s), 6.49 (1H, d, J=16.2 Hz), 6.84 (1H, d, J=8.7 Hz), 7.32-7.43 (5H, m), 7.63 (1H, d, J=2.7 Hz), 7.98 (1H, d, J=16.2 Hz).

(2) Preparation of ethyl (E)-3-{4-[4-(tert-butyl)benzyloxy]-3'-carboxybiphenyl-3-yl}propenoate The title compound was obtained in the same manner as the Example 1 (2) using the following raw materials.
Raw materials: ethyl (E)-3-{5-bromo-2-[4-(tert-butyl) benzyloxy]phenyl}propenoate and 3-carboxyphenylboronic acid.
Yield: 49.3% (white solid).
$^1$H-NMR (CDCl$_3$) δ: 1.28-1.37 (12H, m), 4.27 (2H, q, J=7.2 Hz), 5.20 (2H, s), 6.63 (1H, d, J=16.2 Hz), 7.07 (1H, d, J=9.0 Hz), 7.36-7.45 (4H, m), 7.52-7.60 (2H, m), 7.78-7.82 (2H, m), 8.06-8.11 (1H, m), 8.14 (1H, d, J=16.2 Hz), 8.31 (1H, t, J=1.8 Hz).

(3) Preparation of ethyl (E)-3-{4-[4-(tert-butyl)benzyloxy]-3'-carboxybiphenyl-3-yl}propanoate The title compound was obtained in the same manner as the Example 3 using the following raw material.

Raw material: ethyl (E)-3-{4-[4-(tert-butyl)benzyloxy]-3'-carboxybiphenyl-3-yl}propenoate.

Yield: 86.5% (white solid).

$^1$H-NMR (CDCl$_3$) δ: 1.21-1.34 (12H, m), 2.70 (2H, d, J=7.5 Hz), 3.09 (2H, d, J=7.5 Hz), 4.13 (2H, q, J=7.2 Hz), 5.13 (2H, s), 7.10 (1H, d, J=8.4 Hz), 7.37-7.54 (7H, m), 7.76-7.81 (1H, m), 8.02-8.07 (1H, m), 8.30 (1H, t, J=1.8 Hz).

(4) Preparation of 3-{4-[4-(tert-butyl)benzyloxy]-3'-carboxybiphenyl-3-yl}propanoic acid (compound No. 31).

The title compound was obtained in the same manner as the Example 12 (4) using the following raw material.

Raw material: ethyl (E)-3-{4-[4-(tert-butyl)benzyloxy]-3'-carboxybiphenyl-3-yl}propanoate.

Yield: 59.1% (white solid).

$^1$H-NMR (CDCl$_3$) δ: 1.29 (9H, s), 2.58 (2H, d, J=7.8 Hz), 2.91 (2H, d, J=7.8 Hz), 5.16 (2H, s), 7.15 (1H, d, J=9.0 Hz), 7.38-7.57 (7H, m), 7.83-7.89 (1H, m), 8.13 (1H, t, J=1.5 Hz), 12.58 (1H, brs).

Example 32

Preparation of 3-[4-(2,4-dichlorobenzyloxy)-4'-(trifluoromethoxy)biphenyl-3-yl]propanoic acid (compound No. 32)

(1) Preparation of 4-(2,4-dichlorobenzyloxy)-4'-(trifluoromethoxy)biphenyl-3-carbaldehyde The title compound was obtained in the same manner as the Example 2 (1) using the following raw materials.

Raw materials: 4-hydroxy-4'-(trifluoromethoxy)biphenyl-3-carbaldehyde (compound of Example 19 (1)) and 2,4-dichlorobenzyl chloride.

Yield: 78% (white solid).

$^1$H-NMR (CDCl$_3$) δ: 5.30 (2H, s), 7.13 (1H, d, J=8.7 Hz), 7.25-7.35 (3H, m), 7.47 (1H, d, J=2.1 Hz), 7.52 (1H, d, J=8.1 Hz), 7.55-7.61 (2H, m), 7.75 (1H, dd, J=2.7, 8.7 Hz), 8.08 (1H, d, J=2.7 Hz), 10.59 (1H, s).

(2) Preparation of (E)-3-[4-(2,4-dichlorobenzyloxy)-4'-(trifluoromethoxy)biphenyl-3-yl]propenoic acid The title compound was obtained in the same manner as the Example 2 (3) using the following raw materials.

Raw materials: 4-(2,4-dichlorobenzyloxy)-4'-(trifluoromethoxy)biphenyl-3-carbaldehyde and malonic acid.

Yield: 75% (white solid).

$^1$H-NMR (CDCl$_3$) δ: 5.28 (2H, s), 6.61 (1H, d, J=15.9 Hz), 7.00 (1H, d, J=8.4 Hz), 7.25-7.36 (3H, m), 7.46-7.58 (5H, m), 7.75 (1H, d, J=2.4 Hz), 8.21 (1H, d, J=15.9 Hz).

(3) Preparation of 3-[4-(2,4-dichlorobenzyloxy)-4'-(trifluoromethoxy)biphenyl-3-yl]propanoic acid (compound No. 32)

The title compound was obtained in the same manner as the Example 3 using the following raw materials.

Raw material: (E)-3-[4 (2,4-dichlorobenzyloxy)-4'-(trifluoromethoxy)biphenyl-3-yl]propenoic acid.

Yield: 30% (white solid).

$^1$H-NMR (CDCl$_3$) δ: 2.74 (2H, t, J=7.5 Hz), 3.08 (2H, t, J=7.5 Hz), 5.18 (2H, s), 6.94 (1H, d, J=8.4 Hz), 7.23-7.32 (3H, m), 7.36-7.45 (3H, m), 7.48-7.56 (3H, m).

Example 33

Preparation of 3-[4-(3-methylbenzyloxy)-4'-(trifluoromethoxy)biphenyl-3-yl]propanoic acid (compound No. 33)

(1) Preparation of 4-(3-methylbenzyloxy)-4'-(trifluoromethoxy)biphenyl-3-carbaldehyde The title compound was obtained in the same manner as the Example 2 (1) using the following raw materials.

Raw materials: 4-hydroxy-4'-(trifluoromethoxy)biphenyl-3-carbaldehyde (compound of Example 19 (1)) and 3-methylbenzyl bromide.

Yield: 50% (white solid).

$^1$H-NMR (CDCl$_3$) δ: δ 2.39 (3H, s), 5.21 (2H, s), 7.14 (1H, d, J=8.5 Hz), 7.18 (1H, d, J=7.0 Hz), 7.23-7.33 (5H, m), 7.55-7.60 (2H, m), 7.73 (1H, dd, J=8.5, 2.5 Hz), 8.06 (1H, d, J=2.5 Hz), 10.60 (1H, s).

(2) Preparation of (E)-3-[4-(3-methylbenzyloxy)-4'-(trifluoromethoxy)biphenyl-3-yl]propenoic acid The title compound was obtained in the same manner as the Example 2 (3) using the following raw materials.

Raw materials: 4-(3-methylbenzyloxy)-4'-(trifluoromethoxy)biphenyl-3-carbaldehyde and malonic acid.

Yield: 92% (white solid).

$^1$H-NMR (DMSO-d$_6$) δ: 2.33 (3H, s), 5.23 (2H, s), 6.74 (1H, d, J=16.0 Hz), 7.17 (1H, d, J=7.0 Hz), 7.25-7.34 (4H, m), 7.41-7.48 (2H, m), 7.72 (1H, dd, J=8.5, 2.0 Hz), 7.82-7.87 (2H, m), 7.91 (1H, d, J=16.0 Hz), 8.04 (1H, d, J=2.0 Hz), 12.37 (1H, s).

(3) Preparation of 3-[4-(3-methylbenzyloxy)-4'-(trifluoromethoxy)biphenyl-3-yl]propanoic acid (compound No. 33)

The title compound was obtained in the same manner as the Example 3 using the following raw materials.

Raw material: (E)-3-[4-(3-methylbenzyloxy)-4'-(trifluoromethoxy)biphenyl-3-yl]propenoic acid.

Yield: 66% (white solid).

$^1$H-NMR (DMSO-d$_6$) δ: 2.33 (3H, s), 2.57 (2H, t, J=8.0 Hz), 2.90 (2H, t, J=8.0 Hz), 5.15 (2H, s), 7.10-7.15 (2H, m), 7.25-7.32 (3H, m), 7.41 (2H, d, J=9.0 Hz), 7.47-7.51 (2H, m), 7.72 (2H, d, J=9.0 Hz), 12.13 (1H, s).

Example 34

Preparation of 3-[4-(4-phenylbenzyloxy)-4'-(trifluoromethoxy)biphenyl-3-yl]propanoic acid (compound No. 34)

(1) Preparation of 4-(4-phenylbenzyloxy)-4'-(trifluoromethoxy)biphenyl-3-carbaldehyde The title compound was obtained in the same manner as the Example 2 (1) using the following raw materials.

Raw materials: 4-hydroxy-4'-(trifluoromethoxy)biphenyl-3-carbaldehyde (compound of Example 19 (1)) and 4-phenylbenzyl bromide.

Yield: 99% (white solid).

$^1$H-NMR (DMSO-d$_6$) δ: 5.29 (2H, s), 7.17 (1H, d, J=8.5 Hz), 7.28 (2H, d, J=8.5 Hz), 7.34-7.39 (2H, m), 7.43-7.48

(2H, m), 7.52-7.66 (7H, m), 7.75 (1H, dd, J=8.5, 2.5 Hz), 8.08 (1H, d, J=2.5 Hz), 10.62 (1H, s).

(2) Preparation of (E)-3-[4 (4-phenylbenzyloxy)-4'-(trifluoromethoxy)biphenyl-3-yl]propenoic acid The title compound was obtained in the same manner as the Example 2 (3) using the following raw materials.
Raw materials: 4-(4-phenylbenzyloxy)-4'-(trifluoromethoxy)biphenyl-3-carbaldehyde and malonic acid.
Yield: 81% (white solid).
$^1$H-NMR (DMSO-$d_6$) δ: 5.33 (2H, s), 6.76 (1H, d, J=16.0 Hz), 7.29-7.50 (6H, m), 7.58 (2H, d, J=8.5 Hz), 7.68-7.74 (5H, m), 7.85 (2H, d, J=8.5 Hz), 7.95 (1H, d, J=16.0 Hz), 8.06 (1H, d, J=2.0 Hz), 12.37 (1H, s).

(3) Preparation of 3-[4-(4-phenylbenzyloxy)-4'-(trifluoromethoxy)biphenyl-3-yl]propanoic acid (compound No. 34)

The title compound was obtained in the same manner as the Example 3 using the following raw materials.
Raw material: (E)-3-[4-(4-phenylbenzyloxy)-4'-(trifluoromethoxy)biphenyl-3-yl]propenoic acid.
Yield: 20% (white solid).
$^1$H-NMR (DMSO-$d_6$) δ: 2.59 (2H, t, J=8.0 Hz), 2.93 (2H, t, J=8.0 Hz), 5.25 (2H, s), 7.16 (1H, d, J=9.5 Hz), 7.34-7.52 (7H, m), 7.57 (2H, d, J=8.5 Hz), 7.67-7.74 (6H, m), 12.13 (1H, s).

Example 35

Preparation of 3-[4-(4-butylbenzyloxy)-4'-(trifluoromethoxy)biphenyl-3-yl]propanoic acid (compound No. 35)

(1) Preparation of 4-butylbenzyl chloride

Methanesulfonyl chloride (3.069 g, 26.791 mmol) was added to a solution of 4-butylbenzyl alcohol (4.000 g, 24.355 mmol) in dichloromethane (120 mL) at 0° C. under argon atmosphere. Then triethylamine (2.711 g, 26.791 mmol) was added dropwise at a slow speed to this mixture at 0° C., and the mixture was stirred overnight at room temperature. The solvent was evaporated under reduced pressure and the residue was diluted with ethyl acetate. The organic layer was washed with saturated brine, and dried over anhydrous sodium sulfate. The residue obtained by evaporation of the solvent under reduced pressure was purified by column chromatography on silica gel (n-hexane) to give the title compound (3.64 g, 82%) as a colorless oil.
$^1$H-NMR (CDCl$_3$) δ: 0.92 (3H, t, J=7.5 Hz), 1.35 (2H, sext, J=7.5 Hz), 1.52-1.64 (2H, m), 2.60 (2H, t, J=7.5 Hz), 4.57 (2H, s), 7.15-7.18 (2H, m), 7.25-7.30 (2H, m).

(2) Preparation of 4-(4-butylbenzyloxy)-4'-(trifluoromethoxy)biphenyl-3-carbaldehyde The title compound was obtained in the same manner as the Example 2 (1) using the following raw materials.
Raw materials: 4-hydroxy-4'-(trifluoromethoxy)biphenyl-3-carbaldehyde (compound of Example 19 (1)) and 4-butylbenzyl chloride.
Yield: 43% (white solid).
$^1$H-NMR (DMSO-$d_6$) δ: 0.89 (3H, t, J=7.0 Hz), 1.30 (2H, sext, J=7.0 Hz), 1.55 (2H, quint, J=7.0 Hz), 2.58 (2H, t, J=7.0 Hz), 5.31 (2H, s), 7.23 (2H, d, J=8.0 Hz), 7.44 (5H, d, J=8.0 Hz), 7.79 (2H, d, J=8.0 Hz), 7.95-8.00 (2H, m), 10.45 (1H, s).

(3) Preparation of (E)-3-[4-(4-butylbenzyloxy)-4'-(trifluoromethoxy)biphenyl-3-yl]propenoic acid The title compound was obtained in the same manner as the Example 2 (3) using the following raw materials.
Raw materials: 4-(4-butylbenzyloxy)-4'-(trifluoromethoxy)biphenyl-3-carbaldehyde and malonic acid.
Yield: 58% (white solid).
$^1$H-NMR (DMSO-$d_6$) δ: 0.89 (3H, t, J=7.5 Hz), 1.31 (2H, sext, J=7.5 Hz), 1.51-1.61 (2H, m), 2.59 (2H, t, J=7.5 Hz), 5.23 (2H, s), 6.72 (1H, d, J=16.0 Hz), 7.23-7.29 (3H, m), 7.37-7.43 (4H, m), 7.72 (1H, dd, J=9.0, 2.0 Hz), 7.82-7.86 (2H, m), 7.90 (1H, d, J=16.0 Hz), 8.04 (1H, d, J=2.0 Hz), 12.34 (1H, s).

(4) Preparation of 3-[4-(4-butylbenzyloxy)-4'-(trifluoromethoxy)biphenyl-3-yl]propanoic acid (compound No. 35)

The title compound was obtained in the same manner as the Example 3 using the following raw materials.
Raw material: (E)-3-[4-(4-butylbenzyloxy)-4'-(trifluoromethoxy)biphenyl-3-yl]propenoic acid.
Yield: 33% (white solid).
$^1$H-NMR (DMSO-$d_6$) δ: 0.89 (3H, t, J=7.5 Hz), 1.31 (2H, sext, J=7.5 Hz), 1.55 (2H, quint, J=7.5 Hz), 2.56 (2H, t, J=7.5 Hz), 2.58 (2H, t, J=7.5 Hz), 2.89 (2H, t, J=7.5 Hz), 5.15 (2H, s), 7.13 (1H, d, J=9.0 Hz), 7.21-7.23 (2H, m), 7.36-7.42 (4H, m), 7.47-7.50 (2H, m), 7.69-7.73 (2H, m), 12.12 (1H, s).

Example 36

Preparation of (E)-3-{4-[4-(tert-butyl)benzyloxy]biphenyl-3-yl}propenoic acid (compound No. 36)

(1) Preparation of (E)-3-{5-bromo-2-[4-(tert-butyl)benzyloxy]phenyl}propenoic acid The title compound was obtained in the same manner as the Example 2 (3) using the following raw materials.
Raw materials: 5-bromo-2-[4-(tert-butyl)benzyloxy]benzaldehyde (compound of Example 4 (1)) and malonic acid.
Yield: 84% (white solid).
$^1$H-NMR (DMSO-$d_6$) δ: 1.28 (9H, s), 5.17 (2H, s), 6.61 (1H, d, J=16.1 Hz), 7.13-7.17 (1H, m), 7.36-7.44 (4H, m), 7.52-7.55 (1H, m), 7.77 (1H, d, J=16.1 Hz), 7.90 (1H, s), 12.43 (1H, s).

(2) Preparation of (E)-3-{4-[4-(tert-butyl)benzyloxy]biphenyl-3-yl}propenoic acid (compound No. 36).

The title compound was obtained in the same manner as the Example 1 (2) using the following raw materials.
Raw materials: (E)-3-{5-bromo-2-[4-(tert-butyl)benzyloxy]phenyl}propenoic acid and phenylboronic acid.
Yield: 58% (pale yellow solid).
$^1$H-NMR (CDCl$_3$) δ: 1.34 (9H, s), 5.19 (2H, s), 6.63 (1H, d, J=16.1 Hz), 7.06 (1H, d, J=8.8 Hz), 7.33-7.46 (7H, m), 7.54-7.58 (3H, m), 7.78 (1H, d, J=2.4 Hz), 8.22 (1H, d, J=16.1 Hz).

Example 37

Preparation of 3-{4-[4-(tert-butyl)benzyloxy]biphenyl-3-yl}propanoic acid (compound No. 37)

The title compound was obtained in the same manner as the Example 3 using the following raw materials.

Raw material: (E)-3-{5-bromo-2-[4-(tert-butyl)benzyloxy]phenyl}propenoic acid (compound of compound No. 36).
Yield: 33% (white solid).
$^1$H-NMR (CDCl$_3$) δ: 1.33 (9H, s), 2.74 (2H, t, J=7.6 Hz), 3.07 (2H, t, J=7.6 Hz), 5.11 (2H, s), 6.98 (1H, d, J=8.1 Hz), 7.29-7.44 (9H, m), 7.52-7.55 (2H, m).

Example 38

Preparation of (E)-3-{4-[4-(tert-butyl)benzyloxy]-4'-fluorobiphenyl-3-yl}propenoic acid (compound No. 38)

The title compound was obtained in the same manner as the Example 1 (2) using the following raw materials.
Raw materials: (E)-3-{5-bromo-2-[4 (tert-butyl)benzyloxy]phenyl}propenoic acid (compound of Example 36 (1)) and 4-fluorophenylboronic acid.
Yield: 52% (pale yellow solid).
$^1$H-NMR (CDCl$_3$) δ: 1.34 (9H, s), 5.20 (2H, s), 6.63 (1H, d, J=16.1 Hz), 7.04-7.15 (2H, m), 7.37-7.53 (8H, m), 7.72 (1H, d, J=2.2 Hz), 8.20 (1H, d, J=16.1 Hz).

Example 39

Preparation of 3-{4-[4-(tert-butyl)benzyloxy]-4'-fluorobiphenyl-3-yl}propanoic acid (compound No. 39)

The title compound was obtained in the same manner as the Example 3 using the following raw material.
Raw material: (E)-3-{4-[4-(tert-butyl)benzyloxy]-4'-fluorobiphenyl-3-yl}propenoic acid (compound No. 38).
Yield: 22% (white solid).
$^1$H-NMR (CDCl$_3$) δ: 1.34 (9H, s), 2.74 (2H, t, J=7.6 Hz), 3.06 (2H, t, J=7.6 Hz), 5.10 (2H, s), 6.97 (1H, d, J=8.2 Hz), 7.08 (2H, t, J=8.6 Hz), 7.33-7.49 (8H, m).

Example 40

Preparation of (E)-3-{4-[4-(tert-butyl)benzyloxy]-4'-(trifluoromethyl)biphenyl-3-yl}propenoic acid (compound No. 40)

The title compound was obtained in the same manner as the Example 1 (2) using the following raw materials.
Raw materials: (E)-3-{5-bromo-2-[4 (tert-butyl)benzyloxy]phenyl}propenoic acid (compound of Example 36 (1)) and 4-(trifluoromethyl)phenylboronic acid.
Yield: 49% (pale orange solid).
$^1$H-NMR (CDCl$_3$) δ: 1.34 (9H, s), 5.21 (2H, s), 6.64 (1H, d, J=16.0 Hz), 7.09 (1H, d, J=8.6 Hz), 7.37-7.46 (4H, m), 7.57 (1H, dd, J=2.2, 8.6 Hz), 7.63-7.71 (4H, m), 7.77 (1H, d, J=2.2 Hz), 8.21 (1H, d, J=16.0 Hz).

Example 41

Preparation of 3-{4-[4-(tert-butyl)benzyloxy]-4'-(trifluoromethyl)biphenyl-3-yl}propanoic acid (compound No. 41)

The title compound was obtained in the same manner as the Example 3 using the following raw material.
Raw material: (E)-3-{4-[4-(tert-butyl)benzyloxy]-4'-(trifluoromethyl)biphenyl-3-yl}propenoic acid (compound No. 40).

Yield: 79% (white solid).
$^1$H-NMR (CDCl$_3$) δ: 1.34 (9H, m), 2.75 (2H, t, J=7.6 Hz), 3.07 (2H, t, J=7.6 Hz), 5.12 (2H, s), 7.01 (1H, d, J=8.2 Hz), 7.35-7.44 (6H, m), 7.60-7.67 (4H, m).

Example 42

Preparation of (E)-3-{4-[4-(tert-butyl)benzyloxy]-4'-methoxybiphenyl-3-yl}propenoic acid (compound No. 42).

The title compound was obtained in the same manner as the Example 1 (2) using the following raw materials.
Raw materials: (E)-3-{5-bromo-2-[4-(tert-butyl)benzyloxy]phenyl}propenoic acid (compound of Example 36 (1)) and 4-methoxyphenylboronic acid.
Yield: 43% (pale yellow solid).
$^1$H-NMR (CDCl$_3$) δ: 1.34 (9H, s), 3.85 (3H, s), 5.18 (2H, s), 6.62 (1H, d, J=16.1 Hz), 6.96-7.05 (3H, m), 7.37-7.53 (7H, m), 7.73 (1H, d, J=2.2 Hz), 8.22 (1H, d, J=16.1 Hz).

Example 43

Preparation of 3-{4-[4-(tert-butyl)benzyloxy]-4'-methoxybiphenyl-3-yl}propanoic acid (compound No. 43)

The title compound was obtained in the same manner as the Example 3 using the following raw material.
Raw material: (E)-3-{4-[4-(tert-butyl)benzyloxy]-4'-methoxybiphenyl-3-yl}propenoic acid (compound No. 42).
Yield: 74% (white solid).
$^1$H-NMR (DMSO-d$_6$) δ: 1.29 (9H, s), 2.51 (2H, t, J=7.6 Hz), 2.89 (2H, t, J=7.6 Hz), 3.78 (3H, s), 5.13 (2H, s), 6.96-6.99 (2H, m), 7.06-7.09 (1H, d, J=8.2 Hz), 7.38-7.45 (6H, m), 7.51-7.54 (2H, m), 12.10 (1H, bs).

Example 44

Preparation of (E)-3-{4'-(tert-butyl)-4-[4-(tert-butyl)benzyloxy]biphenyl-3-yl}propenoic acid (compound No. 44)

The title compound was obtained in the same manner as the Example 1 (2) using the following raw materials.
Raw materials: (E)-3-{5-bromo-2-[4-(tert-butyl)benzyloxy]phenyl}propenoic acid (compound of Example 36 (1)) and 4-(tert-butyl)phenylboronic acid.
Yield: 58% (pale orange solid).
$^1$H-NMR (CDCl$_3$) δ: 1.34 (9H, s), 1.36 (9H, s), 5.18 (2H, s), 6.62 (1H, d, J=16.1 Hz), 7.05 (1H, d, J=8.6 Hz), 7.37-7.51 (8H, m), 7.58 (1H, dd, J=2.0, 8.6 Hz), 7.77 (1H, d, J=2.0 Hz), 8.21 (1H, d, J=16.1 Hz).

Example 45

Preparation of 3-{4'-(tert-butyl)-4-[4-(tert-butyl)benzyloxy]biphenyl-3-yl}propanoic acid (compound No. 45)

The title compound was obtained in the same manner as the Example 3 using the following raw material.
Raw material: (E)-3-{4'-(tert-butyl)-4-[4-(tert-butyl)benzyloxy]biphenyl-3-yl}propenoic acid (compound No. 44).

Yield: 50% (white solid).

$^1$H-NMR (CDCl$_3$) δ: 1.34 (9H, s), 1.35 (9H, s), 2.72-2.77 (2H, m), 3.04-3.09 (2H, m), 5.10 (2H, s), 6.97 (1H, d, J=8.4 Hz), 7.36-7.49 (10H, m).

Example 46

Preparation of (E)-3-{4-[4 (tert-butyl)benzyloxy]-4'-methylbiphenyl-3-yl}propenoic acid (compound No. 46)

The title compound was obtained in the same manner as the Example 1 (2) using the following raw materials.

Raw materials: (E)-3-{5-bromo-2-[4-(tert-butyl)benzyloxy]phenyl}propenoic acid (compound of Example 36 (1)) and 4-methylphenylboronic acid.

Yield: 51% (yellow solid).

$^1$H-NMR (CDCl$_3$) δ: 1.34 (9H, s), 2.39 (3H, s), 5.18 (2H, s), 6.62 (1H, d, J=16.1 Hz), 7.04 (1H, d, J=8.6 Hz), 7.23-7.26 (2H, m), 7.37-7.46 (6H, m), 7.54 (1H, dd, J=2.2, 8.6 Hz), 7.76 (1H, d, J=2.2 Hz), 8.21 (1H, d, J=16.1 Hz).

Example 47

Preparation of 3-{4-[4-(tert-butyl)benzyloxy]-4'-methylbiphenyl-3-yl}propanoic acid (compound No. 47)

The title compound was obtained in the same manner as the Example 3 using the following raw material.

Raw material: (E)-3-{4-[4-(tert-butyl)benzyloxy]-4'-methylbiphenyl-3-yl}propenoic acid (compound No. 46).

Yield: 95% (white solid).

$^1$H-NMR (CDCl$_3$) δ: 1.34 (9H, s), 2.37 (3H, s), 2.72-2.77 (2H, m), 3.04-3.09 (2H, m), 5.10 (2H, s), 6.97 (1H, d, J=8.2 Hz), 7.19-7.26 (2H, m), 7.36-7.45 (8H, m).

Example 48

Preparation of 3-{4'-butyl-4-[4-(tert-butyl)benzyloxy]biphenyl-3-yl}propanoic acid (compound No. 48)

(1) Preparation of (E)-3-{4'-butyl-4-[4-(tert-butyl) benzyloxy]biphenyl-3-yl}propenoic acid The title compound was obtained in the same manner as the Example 1 (2) using the following raw materials.

Raw materials: (E)-3-{5-bromo-2-[4-(tert-butyl)benzyloxy]phenyl}propenoic acid (compound of Example 36 (1)) and 4-butylphenylboronic acid.

Yield: 49% (pale yellow solid).

$^1$H-NMR (CDCl$_3$) δ: 0.95 (3H, t, J=7.3 Hz), 1.30-1.42 (11H, m), 1.63 (2H, quint, J=7.8 Hz), 2.65 (2H, t, J=7.8 Hz), 5.18 (2H, s), 6.62 (1H, d, J=16.1 Hz), 7.04 (1H, d, J=8.8 Hz), 7.23-7.26 (3H, m), 7.37-7.47 (5H, m), 7.55 (1H, dd, J=2.4, 8.8 Hz), 7.76 (1H, d, J=2.4 Hz), 8.21 (1H, d, J=16.1 Hz).

(2) Preparation of 3-{4'-butyl-4-[4-(tert-butyl)benzyloxy]biphenyl-3-yl}propanoic acid (compound No. 48).

The title compound was obtained in the same manner as the Example 3 using the following raw material.

Raw material: (E)-3-{4'-butyl-4-[4-(tert-butyl)benzyloxy] biphenyl-3-yl}propenoic acid.

Yield: 49% (white solid).

$^1$H-NMR (CDCl$_3$) δ: 0.94 (3H, t, J=7.3 Hz), 1.31-1.41 (11H, m), 1.62 (2H, quint, J=7.6 Hz), 2.63 (2H, t, J=7.7 Hz), 2.74 (2H, t, J=7.7 Hz), 3.06 (2H, t, J=7.6 Hz), 5.10 (2H, s), 6.97 (1H, d, J=8.2 Hz), 7.20-7.25 (2H, m), 7.35-7.46 (8H, m).

Example 49

Preparation of (E)-3-{4-[4-(tert-butyl)benzyloxy]-4'-(methylsulfanyl)biphenyl-3-yl}propenoic acid (compound No. 49)

The title compound was obtained in the same manner as the Example 1 (2) using the following raw materials.

Raw materials: (E)-3-{5-bromo-2-[4-(tert-butyl)benzyloxy]phenyl}propenoic acid (compound of Example 36 (1)) and 4-(methylsulfanyl)phenylboronic acid.

Yield: 38% (pale yellow solid).

$^1$H-NMR (CDCl$_3$) δ: 1.34 (9H, s), 2.52 (3H, s), 5.19 (2H, s), 6.63 (1H, d, J=16.1 Hz), 7.05 (1H, d, J=8.8 Hz), 7.31-7.49 (8H, m), 7.53 (1H, dd, J=2.4, 8.8 Hz), 7.75 (1H, d, J=2.4 Hz), 8.21 (1H, d, J=16.1 Hz).

Example 50

Preparation of (E)-3-(4-benzyloxybiphenyl-3-yl) propenoic acid (compound No. 50)

(1) Preparation of (E)-3-(5-bromo-2-benzyloxyphenyl)propenoic acid

The title compound was obtained in the same manner as the Example 2 (3) using the following raw materials.

Raw materials: 2-benzyloxy-5-bromobenzaldehyde (compound of Example 2 (1)) and malonic acid.

Yield: 44% (white solid).

$^1$H-NMR (DMSO-d$_6$) δ: 5.21 (2H, s), 6.61 (1H, d, J=16.0 Hz), 7.15 (1H, d, J=8.5 Hz), 7.32-7.47 (5H, m), 7.54 (1H, dd, J=8.5, 2.5 Hz), 7.77 (1H, d, J=16.0 Hz), 7.91 (1H, d, J=2.5 Hz), 12.42 (1H, s).

(2) Preparation of (E)-3-(4-benzyloxybiphenyl-3-yl) propenoic acid (compound No. 50)

The title compound was obtained in the same manner as the Example 1 (2) using the following raw materials.

Raw materials: (E)-3-(5-bromo-2-benzyloxyphenyl)propenoic acid and phenylboronic acid.

Yield: 31% (yellow solid).

$^1$H-NMR (DMSO-d$_6$) δ: 5.27 (2H, s), 6.71 (1H, d, J=16.0 Hz), 7.27 (1H, d, J=8.5 Hz), 7.30-7.50 (8H, m), 7.68-7.72 (2H, m), 7.76-7.78 (1H, m), 7.91 (1H, d, J=16.0 Hz), 7.99-8.02 (1H, m), 12.33 (1H, s).

Example 51

Preparation of 3-(4-benzyloxybiphenyl-3-yl)propanoic acid (compound No. 51)

(1) Preparation of ethyl (E)-3-(5-bromo-2-hydroxyphenyl)propenoate

The title compound was obtained in the same manner as the Example 31 (1) using the following raw materials.

Raw materials: 5-bromosalicylaldehyde and triethyl phosphonoacetate.

Yield: 47% (pale yellow solid).

¹H-NMR (CDCl₃) δ: 1.35 (3H, t, J=7.0 Hz), 4.30 (2H, q, J=7.0 Hz), 6.64 (1H, d, J=16.0 Hz), 6.78 (1H, d, J=8.5 Hz), 7.31 (1H, dd, J=8.5, 2.5 Hz), 7.36 (1H, brs), 7.58 (1H, d, J=2.5 Hz), 7.98 (1H, d, J=16.0 Hz).

(2) Preparation of ethyl (E)-3-(4-hydroxybiphenyl-3-yl)propenoate

The title compound was obtained in the same manner as the Example 1 (2) using the following raw materials.

Raw materials: ethyl (E)-3-(5-bromo-2-hydroxyphenyl)propenoate and phenylboronic acid.

Yield: 44% (white solid).

¹H-NMR (CDCl₃) δ: 1.36 (3H, t, J=7.0 Hz), 4.31 (2H, q, J=7.0 Hz), 6.45 (1H, s), 6.71 (1H, d, J=16.0 Hz), 6.93 (1H, d, J=8.0 Hz), 7.31-7.35 (1H, m), 7.39-7.44 (2H, m), 7.47 (1H, dd, J=8.0, 2.5 Hz), 7.52-7.55 (2H, m), 7.69 (1H, d, J=2.5 Hz), 8.08 (1H, d, J=16.0 Hz).

(3) Preparation of ethyl 3-(4-hydroxybiphenyl-3-yl)propanoate

The title compound was obtained in the same manner as the Example 3 using the following raw material.

Raw material: ethyl (E)-3-(4-hydroxybiphenyl-3-yl)propenoate.

Yield: 99% (colorless oil).

¹H-NMR (DMSO-d₆) δ: 1.14 (3H, t, J=7.0 Hz), 2.60 (2H, t, J=7.5 Hz), 2.84 (2H, t, J=7.5 Hz), 4.04 (2H, q, J=7.0 Hz), 6.87 (1H, d, J=8.5 Hz), 7.26 (1H, tt, J=7.0, 2.0 Hz), 7.32 (1H, dd, J=8.5, 2.0 Hz), 7.37 (1H, d, J=2.0 Hz), 7.39-7.42 (2H, m), 7.53-7.57 (2H, m), 9.57 (1H, s).

(4) Preparation of ethyl 3-(4-benzyloxybiphenyl-3-yl)propanoate

The title compound was obtained in the same manner as the Example 2 (1) using the following raw materials.

Raw materials: ethyl 3 (4-hydroxybiphenyl-3-yl)propanoate and benzyl bromide.

Yield: 99% (white solid). ¹H-NMR (DMSO-d₆) δ: 1.13 (3H, t, J=7.0 Hz), 2.64 (2H, t, J=7.5 Hz), 2.94 (2H, t, J=7.5 Hz), 4.03 (2H, q, J=7.0 Hz), 5.19 (2H, s), 7.12 (1H, d, J=9.0 Hz), 7.27-7.48 (10H, m), 7.60 (2H, d, J=7.5 Hz).

(5) Preparation of 3-(4-benzyloxybiphenyl-3-yl)propanoic acid (compound No. 51)

The title compound was obtained in the same manner as the Example 12 (4) using the following raw material.

Raw material: ethyl 3-(4-benzyloxybiphenyl-3-yl)propanoate.

Yield: 81% (white solid).

¹H-NMR (DMSO-d₆) δ: 2.58 (2H, t, J=7.5 Hz), 2.91 (2H, t, J=7.5 Hz), 5.19 (2H, s), 7.11 (1H, d, J=8.0 Hz), 7.27-7.48 (10H, m), 7.60 (2H, d, J=8.0 Hz), 12.12 (1H, s).

Example 52

Preparation of (E)-3-[4-benzyloxy-4'-(tert-butyl)biphenyl-3-yl]propenoic acid (compound No. 52)

The title compound was obtained in the same manner as the Example 2 (1) using the following raw materials.

Raw materials: (E)-3-(5-bromo-2-benzyloxyphenyl)propenoic acid (compound of Example 50 (1)) and 4-(tert-butyl)phenylboronic acid.

Yield: 40% (yellow solid).

¹H-NMR (DMSO-d₆) δ: 1.30 (9H, s), 5.24 (2H, s), 6.64 (1H, d, J=16.0 Hz), 7.22 (1H, d, J=9.0 Hz), 7.34-7.49 (7H, m), 7.59-7.61 (3H, m), 7.80 (1H, d, J=16.0 Hz), 7.89-7.90 (1H, m).

Example 53

Preparation of 3-[4-benzyloxy-4'-(tert-butyl)biphenyl-3-yl]propanoic acid (compound No. 53)

The title compound was obtained in the same manner as the Example 3 using the following raw material.

Raw material: (E)-3-[4-benzyloxy-4'-(tert-butyl)biphenyl-3-yl]propenoic acid (compound No. 52).

Yield: 18% (white solid).

¹H-NMR (DMSO-d₆) δ: 1.30 (9H, s), 2.56 (2H, t, J=7.5 Hz), 2.90 (2H, t, J=7.5 Hz), 5.22 (2H, s), 7.09 (1H, d, J=9.0 Hz), 7.40-7.46 (6H, m), 7.52 (2H, d, J=9.0 Hz), 7.62 (2H, d, J=9.0 Hz), 12.14 (1H, s).

Example 54

Preparation of (E)-3-{4-[4-(tert-butyl)benzyloxy]-4'-chlorobiphenyl-3-yl}propenoic acid (compound No. 54)

The title compound was obtained in the same manner as the Example 1 (2) using the following raw materials.

Raw materials: (E)-3-{5-bromo-2-[4-(tert-butyl)benzyloxy]phenyl}propenoic acid (compound of Example 36 (1)) and 4-chlorophenylboronic acid.

Yield: 29% (pale yellow solid).

¹H-NMR (CDCl₃) δ: 1.34 (9H, s), 5.19 (2H, s), 6.63 (1H, d, J=16.1 Hz), 7.05 (1H, d, J=8.6 Hz), 7.36-7.49 (8H, m), 7.51 (1H, dd, J=2.2, 8.6 Hz), 7.73 (1H, d, J=2.2 Hz), 8.20 (1H, d, J=16.1 Hz).

Example 55

Preparation of 3-{4-[4-(tert-butyl)benzyloxy]-4'-chlorobiphenyl-3-yl}propanoic acid (compound No. 55)

The title compound was obtained in the same manner as the Example 3 using the following raw material.

Raw material: (E)-3-{4-[4-(tert-butyl)benzyloxy]-4'-chlorobiphenyl-3-yl}propenoic acid (compound No. 54).

Yield: 90% (white solid).

¹H-NMR (CDCl₃) δ: 1.34 (9H, s), 2.74 (2H, t, J=7.5 Hz), 3.06 (2H, t, J=7.5 Hz), 5.11 (2H, s), 6.97 (1H, d, J=8.2 Hz), 7.34-7.47 (10H, m).

Example 56

Preparation of (E)-3-{4'-(tert-butyl)-4-[4-(trifluoromethoxy)benzyloxy]biphenyl-3-yl}propenoic acid (compound No. 56)

(1) Preparation of 5-bromo-2-[4-(trifluoromethoxy)benzyloxy]benzaldehyde

The title compound was obtained in the same manner as the Example 2 (1) using the following raw materials.

Raw materials: 4-(trifluoromethoxy)benzyl bromide and 5-bromosalicylaldehyde.

Yield: 66% (white solid).

$^1$H-NMR (DMSO-d$_6$) δ: 5.34 (2H, s), 7.32 (1H, d, J=9.0 Hz), 7.39-7.42 (2H, m), 7.66 (2H, d, J=8.5 Hz), 7.78 (1H, d, J=2.5 Hz), 7.84 (1H, dd, J=9.0, 2.5 Hz), 10.33 (1H, s).

(2) Preparation of (E)-3-{5-bromo-2-[4-(trifluoromethoxy)benzyloxy]phenyl}propenoic acid The title compound was obtained in the same manner as the Example 2 (3) using the following raw materials.

Raw materials: 5-bromo-2-[4-(trifluoromethoxy)benzyloxy]benzaldehyde and malonic acid.

Yield: 92% (white solid).

$^1$H-NMR (DMSO-d$_6$) δ: 5.26 (2H, s), 6.61 (1H, d, J=16.0 Hz), 7.14 (1H, d, J=9.0 Hz), 7.40-7.43 (2H, m), 7.55 (1H, dd, J=9.0, 2.5 Hz), 7.57-7.60 (2H, m), 7.77 (1H, d, J=16.0 Hz), 7.92 (1H, d, J=2.5 Hz), 12.43 (1H, s).

(3) Preparation of (E)-3-{4'-(tert-butyl)-4-[4-(trifluoromethoxy)benzyloxy]biphenyl-3-yl}propenoic acid (compound No. 56)

The title compound was obtained in the same manner as the Example 1 (2) using the following raw materials.

Raw materials: (E)-3-{5-bromo-2-[4-(trifluoromethoxy)benzyloxy]phenyl}propenoic acid and 4-(tert-butyl)phenylboronic acid.

Yield: 35% (white solid).

$^1$H-NMR (DMSO-d$_6$) δ: 1.31 (9H, s), 5.31 (2H, s), 6.69 (1H, d, J=16.0 Hz), 7.24 (1H, d, J=8.5 Hz), 7.42-7.46 (4H, m), 7.61-7.64 (4H, m), 7.67 (1H, dd, J=8.5, 2.0 Hz), 7.91 (1H, d, J=16.0 Hz), 7.97 (1H, d, J=2.0 Hz), 12.36 (1H, s).

Example 57

Preparation of 3-{4'-(tert-butyl)-4-[4-(trifluoromethoxy)benzyloxy]biphenyl-3-yl}propanoic acid (compound No. 57)

The title compound was obtained in the same manner as the Example 3 using the following raw material.

Raw material: (E)-3-{4'-(tert-butyl)-4-[4-(trifluoromethoxy)benzyloxy]biphenyl-3-yl}propenoic acid (compound No. 56).

Yield: 47% (white solid).

$^1$H-NMR (DMSO-d$_6$) δ: 1.30 (9H, s), 2.56 (2H, t, J=7.5 Hz), 2.90 (2H, t, J=7.5 Hz), 5.22 (2H, s), 7.09 (1H, d, J=9.0 Hz), 7.40-7.46 (6H, m), 7.52 (2H, d, J=9.0 Hz), 7.62 (2H, d, J=9.0 Hz), 12.14 (1H, s).

Example 58

Preparation of 3-{4-[4-(trifluoromethoxy)benzyloxy]biphenyl-3-yl}propanoic acid (compound No. 58)

(1) Preparation of (E)-3-{4-[4-(trifluoromethoxy)benzyloxy]biphenyl-3-yl}propenoic acid The title compound was obtained in the same manner as the Example 1 (2) using the following raw materials.

Raw materials: (E)-3-{5-bromo-2-[4-(trifluoromethoxy)benzyloxy]phenyl}propenoic acid (compound of Example 56 (2)) and phenylboronic acid.

Yield: 46% (white solid).

$^1$H-NMR (CDCl$_3$) δ: 5.21 (2H, s), 6.62 (1H, d, J=16.0 Hz), 7.02 (1H, d, J=8.5 Hz), 7.27 (2H, d, J=8.0 Hz), 7.34 (1H, tt, J=8.0, 1.5 Hz), 7.42-7.50 (4H, m), 7.56 (2H, d, J=8.5 Hz), 7.57 (1H, dd, J=8.5, 2.5 Hz), 7.79 (1H, d, J=2.5 Hz), 8.20 (1H, d, J=16.0 Hz).

(2) Preparation of 3-{4-[4-(trifluoromethoxy)benzyloxy]biphenyl-3-yl}propanoic acid (compound No. 58).

The title compound was obtained in the same manner as the Example 3 using the following raw material.

Raw material: (E)-3-{4-[4-(trifluoromethoxy)benzyloxy]biphenyl-3-yl}propenoic acid.

Yield: 83% (white solid).

$^1$H-NMR (CDCl$_3$) δ: 2.73 (2H, t, J=7.5 Hz), 3.07 (2H, t, J=7.5 Hz), 5.13 (2H, s), 6.95 (1H, d, J=8.0 Hz), 7.23-7.25 (2H, m), 7.27-7.33 (1H, m), 7.38-7.55 (8H, m).

Example 59

Preparation of N-benzyl-N-{4-[4-(tert-butyl)benzyloxy]-4'-(trifluoromethoxy)biphenyl-3-yl}oxamic acid (compound No. 59).

(1) Preparation of 3-benzylamino-4-[4-(tert-butyl)benzyloxy]-4'-(trifluoromethoxy)biphenyl The title compound was obtained in the same manner as the Example 2 (1) using the following raw materials.

Raw materials: 3-amino-4-[4-(tert-butyl)benzyloxy]-4'-(trifluoromethoxy)biphenyl (compound of Example 6 (3)) and benzyl bromide.

Yield: 93% (yellow oil).

$^1$H-NMR (CDCl$_3$) δ: 1.41 (9H, s), 4.65-4.72 (2H, m), 4.96 (1H, brs), 5.25 (2H, s), 7.02-7.06 (1H, m), 7.15-7.25 (4H, m), 7.26-7.40 (2H, m), 7.56-7.61 (4H, m), 7.64-7.67 (4H, m), 7.89-7.91 (1H, m).

(2) Preparation of methyl N-benzyl-N-{4-[4-(tert-butyl)benzyloxy]-4'-(trifluoromethoxy)biphenyl-3-yl}oxamate The title compound was obtained in the same manner as the Example 6 (4) using the following raw materials.

Raw materials: 3-benzylamino-4-[4-(tert-butyl)benzyloxy]-4'-(trifluoromethoxy)biphenyl and methyl chloroglyoxylate.

Yield: 31% (white solid).

$^1$H-NMR (CDCl$_3$) δ: 1.35 (9H, s), 3.53 (3H, s), 4.44 (1H, d, J=14.4 Hz), 5.10 (2H, s), 5.43 (1H, d, J=14.4 Hz), 7.01-7.05 (2H, m), 7.19-7.26 (7H, m), 7.30-7.36 (4H, m), 7.41-7.45 (3H, m).

(3) Preparation of N-benzyl-N-{4-[4-(tert-butyl)benzyloxy]-4'-(trifluoromethoxy)biphenyl-3-yl}oxamic acid (compound No. 59)

A mixture of methyl N-benzyl-N-{4-[4-(tert-butyl)benzyloxy]-4'-(trifluoromethoxy)biphenyl-3-yl}oxamate (115 mg, 0.194 mmol), methanol (11.0 ml), 2N aqueous sodium hydroxide (0.2 ml) and tetrahydrofuran (11.0 ml) was stirred at room temperature for 1 hour. The reaction mixture was adjusted to pH 5-6 by addition of 2N hydrochloric acid, and extracted with ethyl acetate. The organic layer was washed with saturated brine, and dried over anhydrous sodium sulfate. The residue obtained by evaporation of the solvent under reduced pressure was purified by column chromatography on silica gel (ethyl acetate methanol=4:1) to give the title compound (75 mg, 67%) as a white solid.

This compound was obtained as a mixture of the rotational isomers.

Major isomer: $^1$H-NMR (DMSO-$d_6$) δ: 1.30 (9H, s), 4.19-4.25 (1H, m), 5.21 (2H, s), 5.38-5.44 (1H, m), 7.13-7.26 (6H, m), 7.35-7.53 (10H, m).

Minor isomer: $^1$H-NMR (DMSO-$d_6$) δ: 1.30 (9H, s), 4.90-5.21 (2H, m), 5.15 (2H, s), 7.13-7.26 (6H, m), 7.35-7.53 (10H, m).

Example 60

Preparation of 3-[4-(4-nitrobenzyloxy)-4'-(trifluoromethoxy)biphenyl-3-yl]propanoic acid (compound No. 60)

(1) Preparation of ethyl 3-[4-(4-nitrobenzyloxy)-4'-(trifluoromethoxy)biphenyl-3-yl]propanoate The title compound was obtained in the same manner as the Example 2 (1) using the following raw materials.

Raw materials: ethyl (E)-3-[4-hydroxy-4'-(trifluoromethoxy)biphenyl-3-yl]propanoate (compound of Example 51 (3)) and 4-nitrobenzyl bromide.

Yield: 66% (white solid).

$^1$H-NMR (CDCl$_3$) δ: 1.22 (3H, t, J=7.0 Hz), 2.69 (2H, t, J=7.5 Hz), 3.09 (2H, t, J=7.5 Hz), 4.13 (2H, q, J=7.0 Hz), 5.25 (2H, s), 6.91 (1H, d, J=8.5 Hz), 7.26 (2H, d, J=8.0 Hz), 7.37 (1H, dd, J=8.5, 2.5 Hz), 7.42 (1H, d, J=2.5 Hz), 7.52-7.55 (2H, m), 7.64 (2H, d, J=8.5 Hz), 8.26-8.29 (2H, m).

(2) Preparation of 3-[4-(4-nitorobenzyloxy)-4'-(trifluoromethoxy)biphenyl-3-yl]propanoic acid (compound No. 60)

The title compound was obtained in the same manner as the Example 12 (4) using the following raw material.

Raw material: ethyl 3-[4-(4-nitrobenzyloxy) 4'-(trifluoromethoxy)biphenyl-3-yl]propanoate.

Yield: 42% (white solid).

$^1$H-NMR (DMSO-$d_6$) δ: 2.60 (2H, t, J=7.5 Hz), 2.95 (2H, t, J=7.5 Hz), 5.38 (2H, s), 7.11 (1H, d, J=8.5 Hz), 7.42 (2H, d, J=9.0 Hz), 7.50 (H, dd, J=8.5, 2.0 Hz), 7.54 (1H, d, J=2.0 Hz), 7.71-7.77 (4H, m), 8.27-8.29 (2H, m), 12.14 (1H, s).

Example 61

Preparation of (E)-3-{4-[4-(tert-butyl)benzyloxy]-4'-(trifluoromethoxy)biphenyl-3-yl}propenoic acid (compound No. 61)

The title compound was obtained in the same manner as the Example 1 (2) using the following raw materials.

Raw materials: (E)-3-{5-bromo-2-[4-(tert-butyl)benzyloxy]phenyl}propenoic acid (compound of Example 36 (1)) and 2-methoxyphenylboronic acid.

Yield: 54% (pale yellow solid).

$^1$H-NMR (CDCl$_3$) δ: 1.34 (9H, s), 3.82 (3H, s), 5.18 (2H, s), 6.58 (1H, d, J=16.1 Hz), 6.97-7.04 (3H, m), 7.28-7.32 (2H, m), 7.38-7.45 (4H, m), 7.51 (1H, dd, J=2.0, 8.4 Hz), 7.74 (1H, d, J=2.0 Hz), 8.21 (1H, d, J=16.1 Hz).

Example 62

Preparation of 3-{4-[4-(tert-butyl)benzyloxy]-2'-methoxybiphenyl-3-yl}propanoic acid (compound No. 62)

The title compound was obtained in the same manner as the Example 3 using the following raw material.

Raw material: (E)-3-{4-[4-(tert-butyl)benzyloxy]-2'-methoxybiphenyl-3-yl}propanoic acid (compound No. 61).

Yield: 92% (white solid).

$^1$H-NMR (CDCl$_3$) δ: 1.33 (9H, m), 2.74 (2H, t, J=7.8 Hz), 3.05 (2H, t, J=7.8 Hz), 3.80 (3H, s), 5.10 (2H, s), 6.94-7.03 (3H, m), 7.24-7.30 (2H, m), 7.34-7.44 (6H, m).

Example 63

Preparation of (E)-3-{4'-trifluoromethoxy-4-[4-(trifluoromethyl)benzyloxy]biphenyl-3-yl}propenoic acid (compound No. 63)

(1) Preparation of 4'-trifluoromethoxy-4-[3-(trifluoromethyl)benzyloxy]biphenyl-3-carbaldehyde The title compound was obtained in the same manner as the Example 2 (1) using the following raw materials.

Raw materials: 4-hydroxy-4'-(trifluoromethyl)biphenyl-3-carbaldehyde (compound of Example 19 (1)) and 3-trifluoromethylbenzyl bromide.

Yield: 71% (white solid).

$^1$H-NMR (CDCl$_3$) δ: 5.29 (2H, s), 7.13 (1H, d, J=9.0 Hz), 7.29 (2H, d, J=8.5 Hz), 7.56-7.60 (2H, m), 7.63-7.73 (4H, m), 7.76 (1H, dd, J=9.0, 2.5 Hz), 8.09 (1H, d, J=2.5 Hz), 10.59 (1H, s).

(2) Preparation of (E)-3-{4'-trifluoromethoxy-4-[4-(trifluoromethyl)benzyloxy]biphenyl-3-yl}propenoic acid (compound No. 63)

The title compound was obtained in the same manner as the Example 2 (3) using the following raw materials.

Raw materials: 4'-trifluoromethoxy-4-[3-(trifluoromethyl)benzyloxy]biphenyl-3-carbaldehyde and malonic acid.

Yield: 82% (white solid).

$^1$H-NMR (CDCl$_3$) δ: 5.27 (2H, s), 6.62 (1H, d, J=16.0 Hz), 7.02 (1H, d, J=9.0 Hz), 7.29 (2H, d, J=8.0 Hz), 7.52-7.71 (7H, m), 7.76 (1H, d, J=2.5 Hz), 8.20 (1H, d, J=16.0 Hz).

Example 64

Preparation of 3-{4'-trifluoromethoxy-4-[4-(trifluoromethyl)benzyloxy]biphenyl-3-yl}propanoic acid (compound No. 64)

The title compound was obtained in the same manner as the Example 3 using the following raw material.

Raw material: (E)-3-{4'-trifluoromethoxy-4-[(trifluoromethyl)benzyloxy]biphenyl-3-yl}propenoic acid (compound No. 63).

Yield: 33% (white solid).

$^1$H-NMR (CDCl$_3$) δ: 2.74 (2H, t, J=7.5 Hz), 3.07 (2H, t, J=7.5 Hz), 5.18 (2H, s), 6.95 (1H, d, J=8.0 Hz), 7.23-7.25

(2H, m), 7.38 (1H, dd, J=8.0, 2.0 Hz), 7.41 (1H, d, J=2.0 Hz), 7.50-7.54 (3H, m), 7.59-7.65 (2H, m), 7.71 (1H, s).

Example 65

Preparation of 3-[4-(3,5-dimethylbenzyloxy) 4'-(trifluoromethoxy)biphenyl-3-yl]propanoic acid (compound No. 65)

(1) Preparation of 4'-trifluoromethoxy-4-(3,5-dimethylbenzyloxy)biphenyl- 3-carbaldehyde.の製造

The title compound was obtained in the same manner as the Example 2 (1) using the following raw materials.
Raw materials: 4-hydroxy-4'-(trifluoromethoxy)biphenyl-3-carbaldehyde (compound of Example 19 (1)) and 3,5-dimethylbenzyl bromide.
Yield: 51% (white solid).
$^1$H-NMR (CDCl$_3$) δ: 2.35 (6H, s), 5.17 (2H, s), 7.00 (1H, s), 7.06 (2H, s), 7.14 (1H, d, J=9.0 Hz), 7.25-7.29 (2H, m), 7.55-7.60 (2H, m), 7.73 (1H, dd, J=9.0, 2.5 Hz), 8.07 (1H, d, J=2.5 Hz), 10.60 (1H, s).

(2) Preparation of (E)-3-[4-(3,5-dimethylbenzyloxy)-4'-(trifluoromethoxy)biphenyl-3-yl]propenoic acid The title compound was obtained in the same manner as the Example 2 (3) using the following raw materials.
Raw materials: 4'-trifluoromethoxy-4-(3,5-dimethylbenzyloxy)biphenyl-3-carbaldehyde and malonic acid.
Yield: 64% (white solid).
$^1$H-NMR (CDCl$_3$) δ: 2.34 (6H, s), 5.16 (2H, s), 6.66 (1H, d, J=16.0 Hz), 6.98 (1H, s), 7.04 (1H, d, J=8.5 Hz), 7.06 (2H, s), 7.26-7.29 (2H, m), 7.51 (1H, dd, J=8.5, 2.5 Hz), 7.53-7.56 (2H, m), 7.73 (1H, d, J=2.5 Hz), 8.19 (1H, d, J=16.0 Hz).

(3) Preparation of 3-[4-(3,5-dimethylbenzyloxy)-4'-(trifluoromethoxy)biphenyl-3-yl]propanoic acid (compound No. 65).

The title compound was obtained in the same manner as the Example 3 using the following raw material.
Raw material: (E)-3-[4-(3,5-dimethylbenzyloxy)-4'-(trifluoromethoxy)biphenyl-3-yl]propenoic acid.
Yield: 59% (white solid).
$^1$H-NMR (CDCl$_3$) δ: 2.33 (6H, s), 2.74 (2H, t, J=7.5 Hz), 3.06 (2H, t, J=7.5 Hz), 5.06 (2H, s), 6.96 (1H, s), 6.96 (1H, d, J=8.5 Hz), 7.05 (2H, s), 7.22-7.25 (2H, m), 7.36 (1H, dd, J=8.5, 2.5 Hz), 7.39 (1H, d, J=2.5 Hz), 7.51-7.54 (2H, m).

Example 66

Preparation of 3-[4-(4-methoxybenzyloxy)-4'-(trifluoromethoxy)biphenyl-3-yl]propanoic acid (compound No. 66)

(1) Preparation of 4-(4-methoxybenzyloxy)-4'-(trifluoromethoxy)biphenyl-3-carbaldehyde The title compound was obtained in the same manner as the Example 2 (1) using the following raw materials.
Raw materials: 4-hydroxy-4'-(trifluoromethoxy)biphenyl-3-carbaldehyde (compound of Example 19 (1)) and 4-methoxybenzyl bromide.
Yield: 84% (white solid).
$^1$H-NMR (CDCl$_3$) δ: 3.83 (3H, s), 5.17 (2H, s), 6.93-6.96 (2H,m), 7.16 (1H, d, J=8.5 Hz), 7.26-7.29 (2H, m), 7.37-7.40 (2H, m), 7.56-7.60 (2H, m), 7.73 (1H, dd, J=8.5, 2.5 Hz), 8.06 (1H, d, J=2.5 Hz), 10.55 (1H, s).

(2) Preparation of (E)-3-[4-(4-methoxybenzyloxy)-4'-(trifluoromethoxy)biphenyl-3-yl]propenoic acid The title compound was obtained in the same manner as the Example 2 (3) using the following raw materials.
Raw materials: 4-(4-methoxybenzyloxy)-4'-(trifluoromethoxy)biphenyl-3-carbaldehyde and malonic acid.
Yield: 78% (white solid).
$^1$H-NMR (CDCl$_3$) δ: 3.83 (3H, s), 5.15 (2H, s), 6.62 (1H, d, J=16.0 Hz), 6.93-6.96 (2H, m), 7.06 (1H, d, J=9.0 Hz), 7.26-7.29 (2H, m), 7.38 (2H, d, J=8.5 Hz), 7.52 (1H, dd, J=9.0, 2.0 Hz), 7.55 (2H, d, J=8.5 Hz), 7.72 (1H, d, J=2.0 Hz), 8.16 (1H, d, J=16.0 Hz).

(3) Preparation of 3-[4-(4-methoxybenzyloxy)-4'-(trifluoromethoxy)biphenyl-3-yl]propanoic acid (compound No. 66)

The title compound was obtained in the same manner as the Example 3 using the following raw material.
Raw material: (E)-3-[4-(4-methoxybenzyloxy)-4'-(trifluoromethoxy)biphenyl-3-yl]propenoic acid.
Yield: 62% (white solid).
$^1$H-NMR (CDCl$_3$) δ: 2.72 (2H, t, J=7.5 Hz), 3.03 (2H, t, J=7.5 Hz), 3.82 (3H, s), 5.06 (2H, s), 6.91-6.95 (2H, m), 6.98 (1H, d, J=8.5 Hz), 7.23-7.26 (2H, m), 7.34-7.38 (4H, m), 7.51-7.54 (2H, m).

Example 67

Preparation of 3-[4-(4-methylbenzyloxy)-4'-(trifluoromethoxy)biphenyl-3-yl]propanoic acid (compound No. 67)

(1) Preparation of 4-(4-methylbenzyloxy)-4'-(trifluoromethoxy)biphenyl-3-carbaldehyde The title compound was obtained in the same manner as the Example 2 (1) using the following raw materials.
Raw materials: 4-hydroxy-4'-(trifluoromethoxy)biphenyl-3-carbaldehyde (compound of Example 19 (1)) and 4-methylbenzyl bromide.
Yield: 65% (white solid).
$^1$H-NMR (CDCl$_3$) δ: 2.38 (3H, s), 5.20 (2H, s), 7.14 (1H, d, J=8.5 Hz), 7.23 (2H, d, J=8.0 Hz), 7.27 (2H, d, J=8.5 Hz), 7.35 (2H, d, J=8.0 Hz), 7.55-7.59 (2H, m), 7.73 (1H, dd, J=8.5, 2.5 Hz), 8.06 (1H, d, J=2.5 Hz), 10.58 (1H, s).

(2) Preparation of (E)-3-[4-(4-methylbenzyloxy)-4'-(trifluoromethoxy)biphenyl-3-yl]propenoic acid The title compound was obtained in the same manner as the Example 2 (3) using the following raw materials.
Raw materials: 4-(4-methylbenzyloxy)-4'-(trifluoromethoxy)biphenyl-3-carbaldehyde and malonic acid.
Yield: 82% (white solid).
$^1$H-NMR (CDCl$_3$) δ: 2.37 (3H, s), 5.19 (2H, s), 6.64 (1H, d, J=16.0 Hz), 7.05 (1H, d, J=8.5 Hz), 7.22 (2H, d, J=8.0 Hz), 7.28 (2H, d, J=8.0 Hz), 7.34 (2H, d, J=8.0 Hz), 7.51 (1H, dd, J=8.5, 2.5 Hz), 7.52-7.56 (2H, m), 7.72 (1H, d, J=2.5 Hz), 8.17 (1H, d, J=16.0 Hz).

(3) Preparation of 3-[4-(4-methylbenzyloxy)-4'-(trifluoromethoxy)biphenyl-3-yl]propanoic acid (compound No. 67)

The title compound was obtained in the same manner as the Example 3 using the following raw material.
Raw material: (E)-3-[4-(4-methylbenzyloxy)-4'-(trifluoromethoxy)biphenyl-3-yl]propenoic acid.
Yield: 39% (white solid).
$^1$H-NMR (CDCl$_3$) δ: 2.36 (3H, s), 2.73 (2H, t, J=7.5 Hz), 3.04 (2H, t, J=7.5 Hz), 5.09 (2H, s), 6.97 (1H, d, J=8.0 Hz), 7.19-7.25 (4H, m), 7.33 (2H, d, J=8.5 Hz), 7.36 (1H, dd, J=8.0, 2.5 Hz), 7.39 (1H, d, J=2.5 Hz), 7.50-7.53 (2H, m).

Example 68

Preparation of 3-{4'-trifluoromethoxy-4-[4-(trifluoromethoxy)benzyloxy]biphenyl-3-yl}propanoic acid (compound No. 68)

(1) Preparation of 4'-trifluoromethoxy-4-[4-(trifluoromethoxy)benzyloxy]biphenyl-3-carbaldehyde The title compound was obtained in the same manner as the Example 2 (1) using the following raw materials.
Raw materials: 4-hydroxy-4'-(trifluoromethoxy)biphenyl-3-carbaldehyde (compound of Example 19 (1)) and 4-(trifluoromethoxy)benzyl bromide.
Yield: 99% (white solid).
$^1$H-NMR (CDCl$_3$) δ: 5.24 (2H, s), 7.13 (1H, d, J=8.5 Hz), 7.28 (4H, d, J=9.0 Hz), 7.47-7.52 (2H, m), 7.57-7.59 (2H, m), 7.75 (1H, dd, J=8.5, 2.5 Hz), 8.08 (1H, d, J=2.5 Hz), 10.58 (1H, s).

(2) Preparation of (E)-3-{4'-trifluoromethoxy-4-[4-(trifluoromethoxy)benzyloxy]biphenyl-3-yl}propenoic acid The title compound was obtained in the same manner as the Example 2 (3) using the following raw materials.
Raw materials: 4'-trifluoromethoxy-4-[4-(trifluoromethoxy)benzyloxy]biphenyl-3-carbaldehyde and malonic acid.
Yield: 81% (white solid).
$^1$H-NMR (CDCl$_3$) δ: 5.22 (2H, s), 6.62 (1H, d, J=16.0 Hz), 7.03 (1H, d, J=8.5 Hz), 7.27-7.30 (4H, m), 7.47-7.58 (5H, m), 7.75 (1H, d, J=2.5 Hz), 8.20 (1H, d, J=16.0 Hz).

(3) Preparation of 3-{4'-trifluoromethoxy-4-[4 (trifluoromethoxy)benzyloxy]biphenyl-3-yl}propanoic acid (compound No. 68)

The title compound was obtained in the same manner as the Example 3 using the following raw material.
Raw material: (E)-3-{4'-trifluoromethoxy-4-[4-(trifluoromethoxy)benzyloxy]biphenyl-3-yl}propenoic acid.
Yield: 36% (white solid).
$^1$H-NMR (CDCl$_3$) δ: 2.73 (2H, t, J=7.5 Hz), 3.06 (2H, t, J=7.5 Hz), 5.13 (2H, s), 6.95 (1H, d, J=8.5 Hz), 7.23-7.26 (4H, m), 7.37 (1H, dd, J=8.5, 2.5 Hz), 7.41 (1H, d, J=2.5 Hz), 7.45-7.48 (2H, m), 7.50-7.55 (2H, m).

Example 69

Preparation of 5-{2-{4-[4-(tert-butyl)benzyloxy]-4'-(trifluoromethoxy)biphenyl-3-yl}ethyl}-1H-tetrazole (compound No. 69)

(1) Preparation of 3-{4-[4-(tert-butyl)benzyloxy]-4'-(trifluoromethoxy)biphenyl-3-yl}acrylonitrile A mixture of lithium hydroxide (101 mg, 2.40 mmol), diethyl cyanomethylphosphonate (390 mg, 2.20 mmol) and tetrahydrofuran (20 ml) was stirred at 70° C. for 30 minutes under argon atmosphere. After the reaction mixture was cooled to room temperature, 4-[4-(tert-butyl)benzyloxy]-4'-(trifluoromethoxy)biphenyl-3-carbaldehyde (compound of Example 4 (2); 857 mg, 2.00 mmol) was added, and the mixture was stirred at room temperature for 4 hours. 1N Hydrochloric acid was added to the reaction mixture and the mixture was extracted with ethyl acetate. The organic layer was washed with saturated brine and dried over anhydrous sodium sulfate. The residue obtained by evaporation of the solvent under reduced pressure was purified by column chromatography on silica gel (n-hexane:ethyl acetate=10:1) to give the title compound (631 mg, 70.0%) as a colorless oil.
This compound was obtained as a mixture of the rotational isomers.
Major isomer (E form): $^1$H-NMR (CDCl$_3$) δ: 1.35 (9H, s), 5.14 (2H, s), 6.13 (1H, d, J=16.8 Hz), 7.07-7.76 (12H, m).
Minor isomer (Z form): $^1$H-NMR (CDCl$_3$) δ: 1.34 (9H, s), 5.12 (2H, s), 5.46 (1H, d, J=12.0 Hz), 7.06-7.75 (11H, m), 8.34 (1H, d, J=2.4 Hz).

(2) Preparation of 3-{4-hydroxy-4'-(trifluoromethoxy)biphenyl-3-yl}propionitrile The title compound was obtained in the same manner as the Example 3 using the following raw material.
Raw material: 3-{4-[4-(tert-butyl)benzyloxy]-4'-(trifluoromethoxy)biphenyl-3-yl}acrylonitrile.
Yield: 46% (white solid).
$^1$H-NMR (CDCl$_3$) δ: 2.72 (2H, t, J=7.5 Hz), 3.03 (2H, t, J=7.5 Hz), 5.23 (1H, s), 6.82 (1H, d, J=8.1 Hz), 7.22-7.28 (2H, m), 7.32 (1H, dd, J=2.1, 8.1 Hz), 7.36 (1H, d, J=2.1 Hz), 7.50-7.55 (2H, m).

(3) Preparation of 3-{4-[4-(tert-butyl)benzyloxy]-4'-(trifluoromethoxy)biphenyl-3-yl}propionitrile The title compound was obtained in the same manner as the Example 2 (1) using the following raw materials.
Raw materials: 3-{4-hydroxy-4'-(trifluoromethoxy)biphenyl-3-yl}propionitrile and 4-(tert-butyl)benzyl bromide.
Yield: 98% (colorless oil).
$^1$H-NMR (CDCl$_3$) δ: 1.35 (9H, s), 2.68 (2H, t, J=7.2 Hz), 3.06 (2H, t, J=7.2 Hz), 5.10 (2H, s), 7.03 (1H, d, J=8.4 Hz), 7.24-7.28 (2H, m), 7.33-7.38 (2H, m), 7.39-7.46 (4H, m), 7.52-7.57 (2H, m).

(4) Preparation of 5-{2-{4-[4-(tert-butyl)benzyloxy]-4'-(trifluoromethoxy)biphenyl-3-yl}ethyl}-1H-tetrazole (compound No. 69)

A mixture of 3-{4-[4-(tert-butyl)benzyloxy]-4'-(trifluoromethoxy)biphenyl-3-yl}propionitrile (227 mg, 0.5 mmol), sodium azide (98 mg, 1.5 mmol), triethylamine hydrochloride (103 mg, 0.75 mol) and 1-methyl-2-pyrrolidone (5 mL) was stirred at 150° C. for 4 hours under argon atmosphere.

The reaction mixture was cooled to room temperature, diluted with water and extracted with ethyl acetate. The organic layer was washed with saturated brine and dried over anhydrous sodium sulfate. The residue obtained by evaporation of the solvent under reduced pressure was purified by column chromatography on silica gel (n-hexane:ethyl acetate=1:1) to give the title compound (45 mg, 18%) as a white solid.
$^1$H-NMR (DMSO-d$_6$) δ: 1.29 (9H, s), 3.10-3.27 (4H, m), 5.16 (2H, s), 7.15 (1H, d, J=8.7 Hz), 7.39-7.45 (6H, m), 7.44 (1H, d, J=2.4 Hz), 7.50 (1H, dd, J=2.4, 8.7 Hz), 7.65-7.70 (2H, m).

Example 70

Preparation of (E)-3-{4-[4 (tert-butyl)benzyloxy]-3'-(trifluoromethoxy)biphenyl-3-yl}propenoic acid (compound No. 70)

The title compound was obtained in the same manner as the Example 1 (2) using the following raw materials.
Raw materials: (E)-3-{5-bromo-2-[4-(tert-butyl)benzyloxy]phenyl}propenoic acid (compound of Example 36 (1)) and 3-(trifluoromethoxy)phenylboronic acid.
Yield: 28% (white solid).
$^1$H-NMR (CDCl$_3$) δ: 1.34 (9H, s), 5.20 (2H, s), 6.64 (1H, d, J=15.9 Hz), 7.07 (1H, d, J=8.7 Hz), 7.17-7.24 (1H, m), 7.26-7.50 (7H, m), 7.54 (1H, dd, J=2.4, 8.7 Hz), 7.75 (1H, d, J=2.4 Hz), 8.20 (1H, d, J=15.9 Hz).

Example 71

Preparation of 3-{4-[4-(tert-butyl)benzyloxy]-3'-(trifluoromethoxy)biphenyl-3-yl}propanoic acid (compound No. 71)

The title compound was obtained in the same manner as the Example 3 using the following raw material.
Raw material: (E)-3-{4-[4-(tert-butyl)benzyloxy]-3'-(trifluoromethoxy)biphenyl-3-yl}propenoic acid (compound No. 70).
Yield: 92% (colorless oil).
$^1$H-NMR (CDCl$_3$) δ: 1.34 (9H, s), 2.75 (2H, t, J=7.5 Hz), 3.07 (2H, t, J=7.5 Hz), 5.12 (2H, s), 6.99 (1H, d, J=8.4 Hz), 7.11-7.16 (1H, m), 7.34-7.48 (9H, m).

Example 72

Preparation of (E)-3-{4-[4 (tert-butyl)benzyloxy]-2'-(trifluoromethoxy)biphenyl-3-yl}propenoic acid (compound No. 72)

The title compound was obtained in the same manner as the Example 1 (2) using the following raw materials.
Raw materials: (E)-3-{5-bromo-2-[4-(tert-butyl)benzyloxy]phenyl}propenoic acid (compound of Example 36 (1)) and 2-(trifluoromethoxy)phenylboronic acid.
Yield: 24% (pale yellow solid).
$^1$H-NMR (CDCl$_3$) δ: 1.34 (9H, s), 5.19 (2H, s), 6.58 (1H, d, J=16.2 Hz), 7.06 (1H, d, J=8.7 Hz), 7.33-7.48 (9H, m), 7.66 (1H, d, J=2.1 Hz), 8.19 (1H, d, J=16.2 Hz).

Example 73

Preparation of 3-{4-[4-(tert-butyl)benzyloxy]-2'-(trifluoromethoxy)biphenyl-3-yl}propanoic acid (compound No. 73)

The title compound was obtained in the same manner as the Example 3 using the following raw material.
Raw material: (E)-3-{4-[4-(tert-butyl)benzyloxy]-2'-(trifluoromethoxy)biphenyl-3-yl}propenoic acid (compound No. 72).
Yield: 71% (colorless oil).
$^1$H-NMR (CDCl$_3$) δ: 1.34 (9H, s), 2.73 (2H, t, J=7.5 Hz), 3.05 (2H, t, J=7.5 Hz), 5.11 (2H, s), 6.98 (1H, d, J=9.3 Hz), 7.27-7.45 (10H, m).

Example 74

Preparation of 3-{4'-(tert-butyl)-4-[2-(trifluoromethoxy)benzyloxy]biphenyl-3-yl}propanoic acid (compound No. 74)

(1) Preparation of 4'-(tert-butyl)-4-hydroxybiphenyl-3-carbaldehyde

The title compound was obtained in the same manner as the Example 1 (2) using the following raw materials.
Raw materials: 5-bromosalicylaldehyde and 4-(tert-butyl)phenylboronic acid.
Yield: 64% (white solid).
$^1$H-NMR (CDCl$_3$) δ: 1.37 (9H, s), 7.06 (1H, d, J=8.7 Hz), 7.45-7.52 (4H, m), 7.74-7.79 (2H, m), 9.97 (1H, s), 10.98 (1H, s).

(2) Preparation of ethyl (E)-3-[4'-(tert-butyl)-4-hydroxybiphenyl-3-yl]propenoate The title compound was obtained in the same manner as the Example 31 (1) using the following raw materials.
Raw materials: 4'-(tert-butyl)-4-hydroxybiphenyl-3-carbaldehyde and triethyl phosphonoacetate.
Yield: 70% (pale yellow solid).
$^1$H-NMR (CDCl$_3$) δ: 1.36 (9H, s), 1.36 (3H, t, J=7.2 Hz), 4.30 (2H, q, J=7.2 Hz), 6.26 (1H, s), 6.69 (1H, d, J=16.2 Hz), 6.90 (1H, d, J=8.1 Hz), 7.42-7.50 (5H, m), 7.68 (1H, d, J=2.1 Hz), 8.06 (1H, d, J=16.2 Hz).

(3) Preparation of ethyl 3-[4-hydroxy-4'-(tert-butyl)biphenyl-3-yl]propanoate

The title compound was obtained in the same manner as the Example 3 using the following raw material.
Raw material: ethyl (E)-3-[4'-(tert-butyl)-4-hydroxybiphenyl-3-yl]propenoate.
Yield: 96% (white solid).
$^1$H-NMR (CDCl$_3$) δ: 1.24 (3H, t, J=7.2 Hz), 1.35 (9H, s), 2.75 (2H, t, J=5.7 Hz), 2.95 (2H, t, J=5.7 Hz), 4.15 (2H, q, J=7.2 Hz), 6.94 (1H, d, J=8.4 Hz), 7.29-7.37 (3H, m), 7.40-7.49 (4H, m).

(4) Preparation of ethyl 3-{4'-(tert-butyl)-4-[2-(trifluoromethoxy)benzyloxy]biphenyl-3-yl}propanoate The title compound was obtained in the same manner as the Example 2 (1) using the following raw materials.
Raw materials: ethyl 3-[4'-(tert-butyl)-4-hydroxybiphenyl-3-yl]propanoate and 2-(trifluoromethoxy)benzyl bromide.
Yield: 99% (colorless oil).
$^1$H-NMR (CDCl$_3$) δ: 1.22 (3H, t, J=7.2 Hz), 1.36 (9H, s), 2.68 (2H, t, J=7.5 Hz), 3.07 (2H, t, J=7.5 Hz), 4.12 (2H, q, J=7.2 Hz), 5.22 (2H, s), 6.94 (1H, d, J=8.4 Hz), 7.30-7.50 (9H, m), 7.63-7.66 (1H, m).

(5) Preparation of 3-{4'-(tert-butyl)-4-[2-(trifluoromethoxy)benzyloxy]biphenyl-3-yl}propanoic acid (compound No. 74)

The title compound was obtained in the same manner as the Example 12 (4) using the following raw material.
Raw material: ethyl 3-{4'-(tert-butyl)-4-[2-(trifluoromethoxy)benzyloxy]biphenyl-3-yl}propanoate.
Yield: 99% (white solid).
$^1$H-NMR (DMSO-$d_6$) δ: 1.31 (9H, s), 2.49-2.56 (2H, m), 2.87 (2H, t, J=7.8 Hz), 5.21 (2H, s), 7.13 (1H, d, J=9.0 Hz), 7.42-7.53 (9H, m), 7.66-7.72 (1H, m), 12.06 (1H, brs).

Example 75

Preparation of 3-{4'-(tert-butyl)-4-[3-(trifluoromethoxy)benzyloxy]biphenyl-3-yl}propanoic acid (compound No. 75)

(1) Preparation of ethyl 3-{4'-(tert-butyl)-4-[3-(trifluoromethoxy)benzyloxy]biphenyl-3-yl}propanoate The title compound was obtained in the same manner as the Example 2 (1) using the following raw materials.
Raw materials: ethyl 3-[4'-(tert-butyl)-4-hydroxybiphenyl-3-yl]propanoate (compound of Example 74 (3)) and 3-(trifluoromethoxy)benzyl bromide.
Yield: 99% (colorless oil).
$^1$H-NMR (CDCl$_3$) δ: 1.22 (3H, t, J=7.2 Hz), 1.36 (9H, s), 2.67 (2H, t, J=7.5 Hz), 3.07 (2H, t, J=7.5 Hz), 4.12 (2H, q, J=7.2 Hz), 5.14 (2H, s), 6.92 (1H, d, J=8.7 Hz), 7.15-7.19 (1H, m), 7.33-7.50 (9H, m).

(2) Preparation of 3-{4'-(tert-butyl)-4-[3-(trifluoromethoxy)benzyloxy]biphenyl-3-yl}propanoic acid (compound No. 75)

The title compound was obtained in the same manner as the Example 12 (4) using the following raw material.
Raw material: ethyl 3-{4'-(tert-butyl)-4-[3-(trifluoromethoxy)benzyloxy]biphenyl-3-yl}propanoate.
Yield: 81% (white solid).
$^1$H-NMR (DMSO-$d_6$) δ: 1.31 (9H, s), 2.56 (2H, t, J=7.8 Hz), 2.92 (2H, t, J=7.8 Hz), 5.25 (2H, s), 7.09 (1H, d, J=8.7 Hz), 7.32-7.35 (1H, m), 7.42-7.58 (9H, m), 12.09 (1H, brs).

Example 76

Preparation of 3-[4'-(tert-butyl)-4-(4-chlorobenzyloxy)biphenyl-3-yl]propanoic acid (compound No. 76)

(1) Preparation of ethyl 3-[4'-(tert-butyl)-4-(4-chlorobenzyloxy)biphenyl-3-yl]propanoate The title compound was obtained in the same manner as the Example 2 (1) using the following raw materials.
Raw materials: ethyl 3-[4'-(tert-butyl)-4-hydroxybiphenyl-3-yl]propanoate (compound of Example 74 (3)) and 4-chlorobenzyl bromide.
Yield: 99% (white solid).
$^1$H-NMR (CDCl$_3$) δ: 1.22 (3H, t, J=7.2 Hz), 1.35 (9H, s), 2.66 (2H, t, J=7.5 Hz), 3.05 (2H, t, J=7.5 Hz), 4.12 (2H, q, J=7.2 Hz), 5.09 (2H, s), 6.91 (1H, d, J=8.1 Hz), 7.32-7.49 (10H, m).

(2) Preparation of 3-[4'-(tert-butyl)-4-(4-chlorobenzyloxy)biphenyl-3-yl]propanoic acid (compound No. 76).

The title compound was obtained in the same manner as the Example 12 (4) using the following raw material.
Raw material: ethyl 3-[4'-(tert-butyl)-4-(4-chlorobenzyloxy)biphenyl-3-yl]propanoate.
Yield: 66% (white solid).
$^1$H-NMR (DMSO-$d_6$) δ: 1.30 (9H, s), 2.56 (2H, t, J=7.8 Hz), 2.89 (2H, t, J=7.8 Hz), 5.18 (2H, s), 7.03-7.09 (1H, m), 7.40-7.53 (10H, m), 12.09 (1H, brs).

Example 77

Preparation of 3-{4'-(tert-butyl)-4-[4 (trifluoromethyl)benzyloxy]biphenyl-3-yl}propanoic acid (compound No. 77)

(1) Preparation of ethyl 3-{4'-(tert-butyl)-4-[4 (trifluoromethyl)benzyloxy]biphenyl-3-yl}propanoate The title compound was obtained in the same manner as the Example 2 (1) using the following raw materials.
Raw materials: ethyl 3-[4'-(tert-butyl)-4-hydroxybiphenyl-3-yl]propanoate (compound of Example 74 (3)) and 4-(trifluoromethyl)benzyl bromide.
Yield: 99% (white solid).
$^1$H-NMR (CDCl$_3$) δ: 1.22 (3H, t, J=7.2 Hz), 1.35 (9H, s), 2.68 (2H, t, J=7.5 Hz), 3.08 (2H, t, J=7.5 Hz), 4.12 (2H, q, J=7.2 Hz), 5.18 (2H, s), 6.91 (1H, d, J=8.1 Hz), 7.38-7.49 (6H, m), 7.56-7.58 (2H, m), 7.65-7.67 (2H, m).

(2) Preparation of 3-{4'-(tert-butyl)-4-[4-(trifluoromethyl)benzyloxy]biphenyl-3-yl}propanoic acid (compound No. 77)

The title compound was obtained in the same manner as the Example 12 (4) using the following raw material.
Raw material: ethyl 3-{4'-(tert-butyl)-4-[4-(trifluoromethyl)benzyloxy]biphenyl-3-yl}propanoate.
Yield: 78% (white solid).
$^1$H-NMR (DMSO-$d_6$) δ: 1.30 (9H, s), 2.58 (2H, t, J=7.8 Hz), 2.93 (2H, t, J=7.8 Hz), 5.30 (2H, s), 7.08 (1H, d, J=8.4 Hz), 7.41-7.47 (4H, m), 7.51-7.53 (2H, m), 7.69-7.72 (2H, m), 7.77-7.79 (2H, m), 12.10 (1H, brs).

Example 78

Preparation of 3-[4'-(tert-butyl)-4-(4-butylbenzyloxy)biphenyl-3-yl]propanoic acid (compound No. 78)

(1) Preparation of ethyl 3-[4'-(tert-butyl)-4-(4-butylbenzyloxy)biphenyl-3-yl]propanoate The title compound was obtained in the same manner as the Example 2 (1) using the following raw materials.
Raw materials: ethyl 3-[4'-(tert-butyl)-4-hydroxybiphenyl-3-yl]propanoate (compound of Example 74 (3)) and 4-butylbenzyl chloride.
Yield: 99% (yellow oil).
$^1$H-NMR (CDCl$_3$) δ: 0.93 (3H, t, J=7.2 Hz), 1.22 (3H, t, J=7.2 Hz), 1.32-1.39 (11H, m), 1.54-1.66 (2H, m), 2.59-2.70 (4H, m), 3.02-3.10 (2H, m), 4.10-4.17 (2H, m), 5.09 (2H, s), 6.96 (1H, d, J=8.1 Hz), 7.19-7.22 (2H, m), 7.34-7.49 (8H, m).

(2) Preparation of 3-[4'-(tert-butyl)-4-(4-butylbenzyloxy)biphenyl-3-yl]propanoic acid (compound No. 78).

The title compound was obtained in the same manner as the Example 12 (4) using the following raw material.
Raw material: ethyl 3-[4'-(tert-butyl)-4-(4-butylbenzyloxy)biphenyl-3-yl]propanoate.
Yield: 92% (white solid).
$^1$H-NMR (DMSO-$d_6$) δ: 0.90 (3H, t, J=7.2 Hz), 1.25-1.37 (11H, m), 1.51-1.61 (2H, m), 2.50-2.61 (4H, m), 2.89 (2H, t, J=7.8 Hz), 5.13 (2H, s), 7.09 (1H, d, J=9.0 Hz), 7.21-7.23 (2H, m), 7.36-7.45 (6H, m), 7.50-7.52 (2H, m), 12.09 (1H, brs).

Test Example 1

Human PAI-1 Inhibitory Activity

[Method]
In a 96-well multiplate (black), 1.5 μl of DMSO solution of the present application compound prepared to achieve 80-fold the test concentration (=the final concentration when fluorogenic substrate is added) was diluted with 52.5 μl of pH7.5 Tris buffer. To this solution, 6 μl of 80 nM recombinant human PAI-1 (Molecular Innovations, Inc.) solution prepared by Tris buffer was added, and incubated for 5 minutes at room temperature. Furthermore, 30 μl of 800 IU/ml two-chain tPA (Activity Standard; American diagnostics, inc.) prepared by Tris buffer was added, and the mixed solution was incubated for 15 minutes at room temperature. To this, 30 μl of 400 μM fluorogenic substrate (Pyr-Gly-Arg-MCA; Peptide Institute, Inc.) for tPA prepared by Tris buffer was added and reacted for 30 minutes at room temperature. Every 5 minutes from the reaction start, fluorescence (excitation wavelength=360 nm, emission wavelength=465 nm) was measured using SPECTRAFLUOR (TECAN G.M.B.H.) or GENios (TECAN G.M.B.H.), and increased intensity of fluorescence by 30 minute reaction were measured. Increments of fluorescence by 30 minutes reaction in the presence or absence (tPA alone) of PAI-1 in the control wells (DMSO) were calculated respectively, and their differences ([data in the absence of PAI-1]−[data in the presence of PAI-1]) being PAI-1 activity 100%, the inhibition rates of PAI-1 activity in the presence of the present application compound were obtained.
<Composition of pH7.5 Tris Buffer)
50 mM Tris
150 mM NaCl
10 μg/ml BSA
0.01% Tween80 (SIGMA-ALDRICH Corporation)
[Results]
In the following, inhibition rates of human PAI-1 activity are shown.

TABLE 4

| Compound Number | Inhibition Rate of Human PAI-1 Activity (%) Concentration of Present Application Compound | | | |
|---|---|---|---|---|
| | 25 μM | 10 μM | 5 μM | 2.5 μM |
| 1 | NT | 31 | 18 | NT |
| 2 | NT | 31 | 35 | NT |
| 3 | NT | 68 | 35 | NT |
| 4 | NT | 78 | 84 | 39 |
| 5 | NT | 95 | 87 | 36 |
| 6 | NT | 94 | 83 | 46 |
| 7 | NT | 21 | 14 | NT |
| 8 | NT | 5 | NT | NT |
| 9 | NT | 99 | 90 | 40 |
| 10 | >99 | 65 | 32 | NT |
| 11 | 99 | 84 | 41 | NT |
| 12 | NT | 94 | 92 | 43 |
| 13 | NT | 93 | 83 | 35 |
| 15 | NT | 3 | NT | NT |
| 16 | 94 | 47 | 23 | NT |
| 17 | 96 | 46 | 23 | NT |
| 18 | 97 | 67 | 37 | NT |
| 19 | 92 | 65 | 36 | NT |
| 20 | 77 | 13 | NT | NT |
| 22 | 53 | 10 | NT | NT |
| 24 | 70 | 11 | NT | NT |
| 26 | 80 | 13 | NT | NT |
| 28 | 47 | 7 | NT | NT |
| 29 | 64 | 11 | NT | NT |
| 30 | 93 | 97 | 96 | 72 |
| 31 | 25 | 9 | NT | NT |
| 32 | 92 | 29 | 5 | NT |
| 33 | 94 | 40 | 17 | NT |
| 34 | 88 | 56 | 21 | NT |
| 35 | >99 | 70 | 29 | NT |
| 36 | 89 | 49 | 21 | NT |
| 37 | 97 | 47 | 22 | NT |
| 38 | 96 | 53 | 23 | NT |
| 39 | 99 | 53 | 24 | NT |
| 40 | 95 | 57 | 28 | NT |
| 41 | 99 | 60 | 23 | NT |
| 42 | 84 | 47 | 23 | NT |
| 43 | 93 | 34 | 14 | NT |
| 44 | 94 | 56 | 25 | NT |
| 45 | >99 | 66 | 22 | NT |
| 46 | 91 | 56 | 25 | NT |
| 47 | 97 | 59 | 27 | NT |
| 48 | 94 | 66 | 29 | NT |
| 49 | 21 | 25 | 16 | NT |
| 50 | 31 | 15 | NT | NT |
| 51 | 20 | 9 | NT | NT |
| 52 | 91 | 47 | 22 | NT |
| 53 | 93 | 50 | 20 | NT |
| 54 | 97 | 66 | 30 | NT |
| 55 | 96 | 56 | 23 | NT |
| 56 | 94 | 69 | 32 | NT |
| 57 | 94 | 64 | 28 | NT |
| 58 | 74 | 32 | 19 | NT |
| 59 | 81 | 91 | 64 | NT |
| 60 | 75 | 40 | 22 | NT |
| 61 | 95 | 46 | 21 | NT |
| 62 | 91 | 47 | 22 | NT |
| 63 | 82 | 53 | 24 | NT |
| 64 | 97 | 53 | 22 | NT |
| 65 | 77 | 53 | 25 | NT |
| 66 | 25 | 35 | 15 | NT |
| 67 | 97 | 48 | 21 | NT |
| 68 | 99 | 62 | 29 | NT |
| 69 | >99 | 34 | NT | NT |
| 70 | 93 | 72 | 38 | NT |
| 71 | 95 | 74 | 49 | NT |
| 72 | 93 | 72 | 42 | NT |
| 73 | >99 | 80 | 52 | NT |
| 74 | 94 | 70 | 37 | NT |
| 75 | 95 | 74 | 40 | NT |
| 76 | 97 | 73 | 50 | NT |
| 77 | 95 | 71 | 47 | NT |
| 78 | 93 | 80 | 51 | 31 |

NT: Not Tested

Test Example 2

Human PAI-1 Inhibitory Activity

[Method]

Except using the pH7.4 HEPES buffer instead of pH7.5 Tris buffer, and the change of incubation time from 15 minutes to 10 minutes of the mixed solution added by two-chain tPA solution, tests were carried out similarly to the Test Example 1.

<Compotion of pH7.4 HEPES Buffer>

0.1 M HEPES 0.1 M NaCl mM EDTA 0.1% Polyethylene glycol 8,000 (Hampton Research Corporation)

2 mM Dimethyldecylphoshine oxide [Apo-10] (Fluka Corporation)

[Results]

In the following, inhibition rates of human PAI-1 activity are shown.

TABLE 5

| Compound Number | Inhibition Rate of Human PAI-1 Activity (%) Concentration of Present Application Compound | | | |
|---|---|---|---|---|
| | 3 μM | 1 μM | 0.3 μM | 0.1 μM |
| 5 | 90 | 34 | 13 | 2 |
| 9 | 98 | 25 | 6 | 0 |
| 13 | 99 | 36 | 8 | 5 |
| 35 | 92 | 25 | 5 | 0 |
| 59 | >99 | 68 | 19 | 1 |

From the above results, concentration of the present application compound that inhibits 50% of the human PAI-1 activity ($IC_{50}$) was obtained. The results are shown on the following table.

TABLE 6

| Compound Number | $IC_{50}$ (μM) |
|---|---|
| 5 | 1.27 |
| 9 | 1.30 |
| 13 | 1.17 |
| 35 | 1.41 |
| 59 | 0.66 |

Test Example 3

Rat PAI-1 Inhibitory Activity

[Method]

Similar tests were carried out using recombinant rat PAI-1 (Molecular Innovations, Inc.) instead of recombinant human PAI-1 in the Test Example 2.

[Results]

In the following, inhibition rates of rat PAI-1 activity are shown.

TABLE 7

| Compound Number | Inhibition Rate of Rat PAI-1 Activity (%) Concentration of Present Application Compound | | | |
|---|---|---|---|---|
| | 10 μM | 3 μM | 1 μM | 0.3 μM |
| 5 | 93 | 52 | 15 | 5 |
| 9 | 96 | 71 | 15 | 0 |
| 13 | >99 | 69 | 14 | 0 |
| 35 | 89 | 47 | 5 | 0 |
| 59 | >99 | >99 | 38 | 7 |

From the above results, concentration of the present application compound that inhibits 50% of the rat PAI-1 activity ($IC_{50}$) was obtained. The results are shown on the following table.

TABLE 8

| Compound Number | $IC_{50}$ (μM) |
|---|---|
| 5 | 2.80 |
| 9 | 2.07 |
| 13 | 2.17 |
| 35 | 3.31 |
| 59 | 1.11 |

Test Example 4

Human PAI-1 Inhibitory Activity

[Method]

100 μl of tPA solution where one-chain recombinant tPA (hereinafter reffered to as tPA; American diagnostica, inc.) diluted with Buffer A to achieve a concentration of 10 μg/ml was added to each well of 96-well plate (Nunc Maxisorp), incubated for one night at 4° C. to coated with tPA. Then, after suction of tPA solution from the 96-well plate, rinsed successively with Buffer A and Buffer B.

To Buffer B, solutions of the present application compound dissolved with DMSO (final DMSO concentration: 0.2%) and recombinant human PAI-1 (Molecular Innovations, Inc.) were added and blended so that the final concentrations would be 0.1 to 3.0 μM and 50 ng/ml respectively, and were incubated for 15 minutes on ice. These mixed solutions were added to rinsed 96-well plates at 100 μl/well, and incubated for 60 minutes at room temperature. To prepare calibration curve, PAI-1 solutions without the present application compound (solutions where the final concentrations being 100, 50, 25, 12.5, 6.25, 3.13, 1.56 ng/ml PAI-1) were added at 100 μl/well, and were incubated for 60 minutes at room temperature, as standard.

After incubation, the reaction mixture was suction removed, and rinsed each well with Wash Buffer. Next, anti-human PAI-1 monoclonal antibody (PROGEN Inc.) diluted with Buffer C to be 3.0 μg/ml was added to the 96-well plate at 100 μl/well, and incubated for 1 hour at room temperature. After rinsing each well with Wash Buffer, alkaline phosphatase-labeled goat anti-mouse IgG (H+L) (Jackson ImmunoResearch, Inc.) diluted with Buffer D to be 0.12 μg/ml was added at 100 μl/well, and incubated for 1 hour at room temperature. After rinsing each well with Wash Buffer, 1.0 mg/ml p-Nitrophenyl Phosphate (SIGMA) was added to the 96-well plate at 100 μl/well to start the reaction. After 30 to 60 minutes, 25 μl of 0.5 N NaOH was added to stop the reaction, and the absorbance was measured at 405 nm using a multiplate reader (GENios; TECAN G.M.B.H.).

Based on the calibration curve prepared from the standard wells, amounts of PAI-1 bound to tPA in the wells treated with the present application compound were calculated, and the PAI-1 inhibition rates by the present application compounds were obtained by the following equation.

[PAI-1 Inhibition Rate(%)]=[1−(amount of PAI-1 bound to tPA on the well treated with the present application compound)/(amount of PAI-1 bound to tPA on the well treated with PAI-1 solution without present application compound (solution with the final concentration of 50 ng/ml PAI-1)]× 100

<Composition of Buffer A>
0.1 M Tris-HCl
150 mM NaCl
pH 7.7
<Composition of Buffer B>
50 mM sodium phosphate
0.1 M NaCl
1 mM EDTA
pH 6.6
<Composition of Buffer C>
50 mM sodium phosphate
100 mM NaCl
pH 7.4
<Composition of Buffer D>
0.01 M Tris-HCl
0.25 M NaCl
pH 8.0
<Composition of Wash Buffer>
0.05% Tween 20
0.1% BSA in Buffer A
<Composition of p-Nitrophenyl Phosphate Solution>
1 M Diethanolamine
0.5 mM $MgCl_2$
p-Nitrophenyl phosphate
pH 9.8
[Results]

In the following, inhibition rates of human PAI-1 activities are shown.

TABLE 9

| Compound Number | Inhibition Rate of Human PAI-1 Activity (%) Concentration of Present Application Compound | | |
|---|---|---|---|
| | 3 μM | 1 μM | 0.3 μM |
| 5 | 67 | 23 | 9 |
| 13 | 41 | 14 | 7 |

Test Example 5

Anti-thrombotic Activity (Rat AV Shunt Model)

AV shunt model using 7-week old male Crlj:CD(SD) rat was prepared, and anti thrombotic activities when the present application compound was administered orally were examined.

[Method]

(1) Preparation of Administering Solution of Test Compound

Required amount of the test compound was weighed, suspended by adding 0.5% CMC (carboxymethylcellulose)-Na solution little by little, and prepared the solutions so that the final solutions being 2 mg/ml and 6 mg/ml using a graduated cylinder (10 mg/kg and 30 mg/kg solutions, respectively). 5 ml was prepared for 1 course.

(2) Administration

To 7-week old Crlj:CD(SD) male rats, vehicle (0.5% CMC-Na solution) 5 ml/kg or the administering solution of test compound 5 ml/kg (10 mg/kg or 30 mg/kg) was administered orally for 4 days. The administration on the 4th day was carried out about 1 hour before the following perfusion start.

(3) Preparation of AV Shunt Model and Measurement of Thrombus Weight

Put a 6.5 cm silk thread (Matsuda Ika Kogyou; No. 1-0) through in an 8 cm No. 7 polyethylene tube (Hibiki), connect No. 3 tubes (12.5 cm) to both ends via No. 5 tube (1.5 cm), and a catheter for shunt was prepared. On the connected part where the silk thread is through, parafilm was wrapped around to avoid blood leakage.

Rats were anesthetized with pentobarbital (50 mg/kg; intraperitoneally). Saline was filled in the above catheter, and both ends of the catheter were inserted in right carotid artery and left carotid artery, respectively, and blood was circulated. 30 minutes later, the catheter was pinched with forceps to stop blood flow, and tube parts where the silk thread is through were cut and removed. The silk thread was carefully removed from the tubes, remaining wet weight was weighed after removing the liquid phase by filter paper, and further subtraction of the weight of the silk thread, gives the thrombus weight.

(4) Statistical Treatment

For the thrombus weight in each group, an average value±standard error (S.E.) was calculated. For the significance test between the vehicle administered group and the present application compound administered group, Dunnett's multiple comparison was carried out (significance level 5%). For the test, the SAS System Release 8.2 (TS2M0) for Windows (Registered Trademark) (SAS Institute Inc.) and its coorperative system EXSAS Ver. 7.10 (Arm Systex Co. Ltd.) were employed.

[Results]

The results are shown in the following.

TABLE 10

| Study Compound | Dose (mg/kg/day) | Number of Examples | Thrombus Weight (mg) |
|---|---|---|---|
| Vehicle (0.5% CMC-Na) | — | 5 | 72.7 ± 2.7 |
| Compound Number 5 | 10 | 5 | 57.5 ± 5.0* |
| Compound Number 18 | 30 | 5 | 60.4 ± 3.8* |

*p < 0.05

INDUSTRIAL APPLICABILITY

The compounds of the present invention have inhibitory action against PAI-1. Therefore, the compounds of the present invention are useful as a medicament for preventive and/or therapeutic treatment of diseases caused by an expression of PAI-1 or an enhancement of PAI-1 activity.

What is claimed is:

1. A compound represented by the following general formula (I) or a salt thereof:

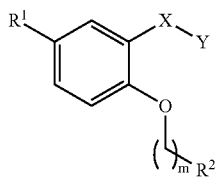

(I)

wherein $R^1$ represents a $C_{6-10}$ aryl group substituted with a group or groups selected from a halogen atom, a nitro group, a $C_{1-6}$ alkyl group, a halogenated $C_{1-6}$ alkyl group, a $C_{1-6}$ alkoxy group, a halogenated $C_{1-6}$ alkoxy group, a $C_{1-6}$ alkylenedioxy group, a $C_{1-6}$ alkylsulfanyl group, a carboxy group, and an amino group, $R^2$ represents a $C_{6-10}$ aryl group substituted with a group or groups selected from a halogen atom, a nitro group, a $C_{1-6}$ alkyl group, a halogenated $C_{1-6}$ alkyl group, a $C_{1-6}$ alkoxy group, a halogenated $C_{1-6}$ alkoxy group, a phenyl group, and a carboxy group, X represents —$CH_2$—, —$CH_2CH_2$—, —CH=CH— or —N($R^3$)—C(=O)— wherein the nitrogen atom binds to the benzene ring and the carbon atom binds to Y, and $R^3$ represents hydrogen atom, a $C_{1-4}$ alkyl group or a $C_{7-12}$ aralkyl group, Y represents a carboxy group or a 1H-tetrazol-5-yl group, and m represents 0 or 1.

2. The compound according to claim 1 or a salt thereof, wherein

X is —$CH_2$—, —$CH_2CH_2$— or —N($R^3$)—C(=O)— wherein the nitrogen atom binds to the benzene ring and the carbon atom binds to Y, Y is a carboxy group.

3. A medicament which comprises as an active ingredient a compound according to claim 1 or a pharmacologically acceptable salt thereof.

4. A PAI-1 inhibitor which comprises as an active ingredient a compound according to claim 1 or a salt thereof.

* * * * *